United States Patent
Plant et al.

(10) Patent No.: US 6,599,924 B1
(45) Date of Patent: Jul. 29, 2003

(54) 2-HETARYL-3,4-DIHYDRO-2H-PYRROLE DERIVATIVES

(75) Inventors: Andrew Plant, Leverkusen (DE); Bernd Alig, Königswinter (DE); Alan Graff, Leverkusen (DE); Udo Kraatz, Leverkusen (DE); Wolfgang Krämer, Burscheid (DE); Christoph Erdelen, Leichlingen (DE); Andreas Turberg, Haan (DE); Norbert Mencke, Leverkusen (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/807,136

(22) PCT Filed: Oct. 1, 1999

(86) PCT No.: PCT/EP99/07295

§ 371 (c)(1),
(2), (4) Date: Apr. 5, 2001

(87) PCT Pub. No.: WO00/21958

PCT Pub. Date: Apr. 20, 2000

(30) Foreign Application Priority Data

Oct. 14, 1998 (DE) .......................... 198 47 076

(51) Int. Cl.$^7$ .................. A61K 31/44; C07D 401/04; C07D 409/04

(52) U.S. Cl. .................. 514/343; 546/276.4; 546/14; 546/286; 546/288; 548/527; 548/205; 549/59; 549/491; 549/497; 514/428

(58) Field of Search .................. 546/276.4, 14, 546/286, 288; 514/393, 428; 548/527; 549/59, 491, 497

(56) References Cited

FOREIGN PATENT DOCUMENTS

| EP | 0421102 | 4/1991 |
|----|---------|--------|
| WO | 95/04719 | 2/1995 |
| WO | 98/22438 | 5/1998 |

*Primary Examiner*—Joseph K. McKane
*Assistant Examiner*—Golam M. M. Shameem
(74) *Attorney, Agent, or Firm*—Richard E. L. Henderson; Joseph C. Gil; John E. Mrozinski, Jr.

(57) ABSTRACT

The invention relates to novel 2-hetaryl-3,4-dihydro-2H-pyrrole derivatives of the formula (I)

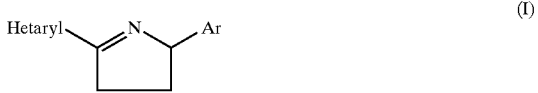

in which
Hetaryl represents substituted heterocyclyls and
Ar represents substituted phenyl,
to a plurality of processes for their preparation and to their use as pesticides.

13 Claims, No Drawings

2-HETARYL-3,4-DIHYDRO-2H-PYRROLE DERIVATIVES

This application is a 371 of PCT/EP99/07295 Oct. 1, 1999.

FIELD OF THE INVENTION

The invention relates to novel 2-hetaryl-3,4-dihydro-2H-pyrrole derivatives, to a plurality of processes for their preparation and to their use as pesticides.

BACKGROUND OF THE INVENTION

Hitherto, only substituted cyclic α,α'-diphenylimines have been disclosed: three 2,5-diphenyl-1-pyrrolines which are alkoxy-substituted in the 2-phenyl ring [5-(2,5-dimethoxyphenyl)-2-phenyl-3,4-dihydro-2H-pyrrole and 5-(4-methoxyphenyl)-2-phenyl-3,4-dihydro-2H-pyrrole from Chem. Ber. 96, 93 (1963) and the corresponding 4-propoxy compound from J. Prakt. Chem., series 4, 1, 57 (1955)] and 2,6-diphenyl-3,4,5,6-tetrahydropyridine, which is not further substituted [cf., for example, Bull. Soc. Chim. Fr. 1974, 258 and Chem. Ber. 116, 3931 (1983)].

WO 98/22438 describes novel substituted α,α'-diphenylimines and their suitability for use as pesticides. However, hitherto nothing has been disclosed about substituted α-hetaryl-α'-phenylimines and their suitability for use as pesticides.

SUMMARY OF THE INVENTION

2-Hetaryl-3,4-dihydro-2H-pyrrole derivatives of the formula (I)

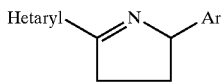
(I)

may be used as pesticides.

DETAILED DESCRIPTION

This invention accordingly provides novel 2-hetaryl-3,4-dihydro-2H-pyrrole derivatives of the formula (I)

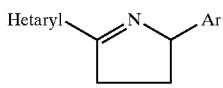
(I)

in which

Hetaryl represents unsaturated 5 to 10-membered mono- or bicyclic heterocycles, for example 5 or 6-membered monocycles having one or more heteroatoms from the group consisting of N, O and S, optionally mono- or polysubstituted by radicals from the list $H^1$, where $H^1$ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio, carbamoyl, thiocarbamoyl, alkoximino or —S(O)$_o$R$^3$, Ar represents the radical

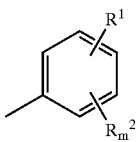

in which
m represents 0, 1, 2, 3 or 4,
$R^1$ represents halogen or represents one of the groupings below
(l) —X—A
(m) —B—Z—D
(n) —Y—E
$R^2$ represents hydrogen, halogen, cyano, nitro, alkyl, alkoxy, halogenoalkyl, halogenoalkoxy, alkoxyalkoxy or —S(O)$_o$R$^3$,
o represents 0, 1 or 2,
$R^3$ represents alkyl or halogenoalkyl,
X represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or dialkylsilylene,
A represents phenyl, naphthyl or tetrahydronaphthyl, each of which is optionally mono- or polysubstituted by radicals from the list $W^1$, or represents 5- to 10-membered heterocyclyl containing one or two aromatic rings and having one or more heteroatoms from the group consisting of nitrogen, oxygen and sulphur and being in each case optionally mono- or polysubstituted by radicals from the list $W^2$,
B represents p-phenylene which is optionally mono- or disubstituted by radicals from the list $W^1$,
Z represents oxygen or sulphur,
D represents hydrogen, alkyl, alkenyl, alkinyl, halogenoalkyl, halogenoalkenyl, in each case optionally halogen, alkyl , alkenyl-, halogenoalkenyl-, phenyl-, styryl-, halogenophenyl- or haloenostyryl-substituted cycloalkyl or cycloalkylalkyl, represents in each case optionally halogen- or alkyl-substituted cycloalkenyl or cycloalkenylalkyl, represents in each case optionally nitro-, halogen- alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms from the group consisting of nitrogen, oxygen and sulphur, represents —CO—R$^4$, —CO—NR$^5$R$^6$ or represents the grouping —(CH$_2$)$_p$—(CR$^7$R$^8$)$_q$—(CH$_2$)$_r$—G or
Z and D together represent optionally nitro-, halogen-, alkyl-, alkoxy halogenoalkyl- or halogenoalkoxy-substituted phenoxyalkyl,
Y represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or represents p-phenylene which is optionally mono- or disubstituted by radicals from the list $W^1$,
E represents hydrogen, alkyl, alkenyl, alkinyl, halogenoalkyl, halogenoalkenyl, in each case optionally halogen-, alkyl-, alkenyl-, halogenoalkenyl-, phenyl-, styryl-, halogenophenyl- or halogenostyryl-substituted cycloalkyl, represents in each case optionally halogen- or alkyl-substituted cycloalkenyl, represents phenyl which is optionally mono- to tetrasubstituted by radicals from the list $W^1$ or represents 5- or 6-membered hetaryl having one or two heteroatoms from the group consisting of nitrogen, oxygen and sulphur and being in each case optionally mono- to tetrasubstituted by radicals from the list $W^2$ or represents the grouping

$R^4$ represents alkyl, alkoxy, alkenyl, alkenyloxy, in each case optionally halogen-, alkyl-, alkenyl-, halogenoalkyl- or halogenoalkenyl-substituted cycloalkyl, cycloalkyloxy or cycloalkylalkyloxy or represents in each case optionally nitro-, halogen-, alkyl-, alkoxy-, halogenoalkyl- or halogenoalkoxy-substituted phenyl or naphthyl, $R^5$ represents hydrogen or alkyl, $R^6$ represents alkyl, halogenoalkyl, in each case optionally halogen-, alkyl-, alkenyl-, halogenoalkyl- or halogenoalkenyl-substituted cycloalkyl or cycloalkylalkyl or represents in each case optionally halogen-, alkyl-, alkoxy-, halogenoalkyl- or halogenoalkoxy-substituted phenyl or phenylalkyl, p, q and r independently of one another each represent 0, 1, 2 or 3, their sum being smaller than 6, $R^7$ and $R^8$ independently of one another each represent hydrogen or alkyl, G represents cyano, represents an optionally halogen-, alkyl- or halogenoalkyl- and, at the point of linkage, optionally $R^9$-substituted 5- or 6-membered heterocycle having 1 to 3 identical or different heteroatoms from the group consisting of nitrogen, oxygen and sulphur or one of the following groups

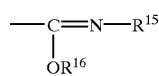

(a)

(b)

(c)

(d)

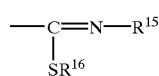

(e)

(f)

(g)

(h)

(i)

(j)

(k)

$R^9$ represents hydrogen, alkyl, alkenyl, halogenoalkyl, halogenoalkenyl, in each case optionally halogen-, alkyl- or halogenoalkyl-substituted cycloalkyl or cycloalkylalkyl or represents arylalkyl which is optionally mono- to pentasubstituted by radicals from the list $W^3$, $R^{10}$ represents hydrogen, alkyl, alkenyl, halogenoalkyl, halogenoalkenyl, in each case optionally halogen-, alkyl- or halogenoalkyl-substituted cycloalkyl or cycloalkylalkyl or represents arylalkyl which is optionally mono- to pentasubstituted by radicals from the list $W^3$, $R^{11}$ and $R^{12}$ independently of one another each represent hydrogen, alkyl, alkenyl, halogenoalkyl, halogenoalkenyl, alkoxy, in each case optionally halogen-, alkyl- or halogenoalkyl-substituted cycloalkyl or cycloalkylalkyl, represents aryl or arylalkyl, each of which is optionally mono- to pentasubstituted by radicals from the list $W^3$, represent —$OR^{10}$ or —$NR^9R^{10}$ or together represent an alkylene chain having 2 to 6 members in which optionally one methylene group is replaced by oxygen, $R^{13}$ represents —$OR^{10}$, —$NR^9R^{10}$ or —$N(R^9)$—$COOR^{10}$, $R^{14}$, $R^{15}$ and $R^{16}$ independently of one another each represent alkyl, $W^1$ represents hydrogen, halogen, cyano, formyl, nitro, alkyl, trialkylsilyl,, alkoxy, halogenoalkyl, halogenoalkoxy, halogenoalkenyloxy, alkylcarbonyl, alkoxycarbonyl, pentafluorothio or, —$S(O)_oR^3$, $W^2$ represents halogen, cyano, formyl, nitro, alkyl, trialkylsilyl, alkoxy, halogenoalkyl, halogenoalkoxy, alkylcarbonyl, alkoxycarbonyl, pentafluorothio, —$S(O)_oR^3$ or —$C(R^9)$=N—$R^{13}$, $W^3$ represents halogen, cyano, nitro, alkyl, alkoxy, halogenoalkyl, halogenoalkoxy, dialkylamino, —$S(O)_oR^3$, —$COOR^{17}$ or —$CONR^{18}R^{19}$, $R^{17}$ represents hydrogen, alkyl, halogenoalkyl, optionally halogen-, alkyl- or halogenoalkyl-substituted cycloalkyl or represents phenyl which is optionally mono- to pentasubstituted by radicals from the list $W^4$, $R^{18}$ and $R^{19}$ independently of one another each represent hydrogen, alkyl alkenyl, halogenoalkyl, halogenoalkenyl, alkoxy, in each case optionally halogen-, alkyl- or halogenoalkyl-substituted cycloalkyl or cycloalkylalkyl or represent aryl or arylalkyl, each of which is optionally mono- to pentasubstituted by radicals from the list $W^4$, represent —$OR^{14}$ or —$NR^{15}R^{16}$ or together represent an alkylene chain having 2 to 6 members in which optionally one methylene group is replaced by oxygen, and $W^4$ represents halogen, cyano, nitro, alkyl, alkoxy, halogenoalkyl, halogenoalkoxy, dialkylamino, alkoxycarbonyl, dialkylaminocarbonyl or —$S(O)_o R^3$.

Depending, inter alia, on the type of substituents, the compounds of the formula (I) can be present as geometrical and/or optical isomers or isomer mixtures, of varying composition, which, if appropriate, can be separated in a customary manner. The present invention provides both the pure isomers and the isomer mixtures, their preparation and use and compositions comprising them. Hereinbelow, for the sake of simplicity, only compounds of the formula (I) are referred to however, although this includes the pure compounds and, if appropriate, also mixtures having varying proportions of isomeric compounds.

Furthermore, it has been found that the novel compounds of the formula (I) can be obtained by one of the processes described below:

A) cyclic imines of the formula (I)

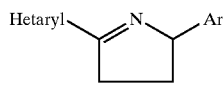
(I)

in which
Hetaryl and Ar are as described above
can be prepared by reacting aminoketone derivatives of the formula (II)

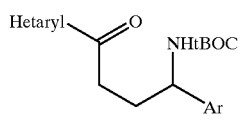
(II)

in which
Hetaryl and Ar are as defined above
with an acid, followed by cyclocondensation, if appropriate in the presence of an acid binder;

B) cyclic imines of the formula (I) can also be prepared by reacting O-methylsulphonyl oximes of the formula (III)

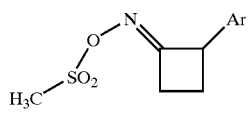
(III)

in which
Ar is as defined above,
with hetaryl Grignard reagents of the formula (IV)

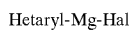
Hetaryl-Mg-Hal (IV)

in which
Hetaryl is as defined above and
Hal represents bromine or iodine,
in the presence of a diluent;

C) cyclic imines of the formula (I-b)

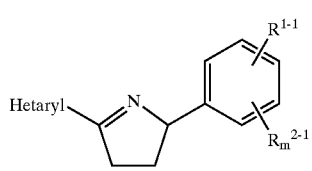
(I-b)

in which
Hetaryl is as defined above,
m is as defined above,
$R^{1-1}$ represents A or one of the groupings below
(m) —B—Z—D

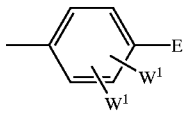
(n-a)

where
A, B, D, E, $W^1$ and Z are as defined above and
$R^{2-1}$ represents hydrogen, fluorine, cyano, nitro, alkyl, alkoxy, halogenoalkyl, halogenoalkoxy, alkoxyalkoxy or —$SR^3$, where
$R^3$ is as defined above
can be prepared by coupling compounds of the formula (V)

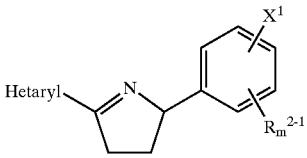
(V)

in which
Hetaryl is as defined above,
$R^{2-1}$ and m are as defined above and
$X^1$ represents bromine, iodine, —OH or —$OSO_2CF_3$ α) with boronic acids of the formula (VI)

$R^{1-1}B(OH)_2$ (VI), in which
$R^{1-1}$ is as defined above,
in the presence of a catalyst and in the presence of an acid binder and in the presence of a solvent; or β) in the case that $X^1$ is OH, coupling with compounds of the formula

$R^{1-1}Ab$ in which $R^{1-1}$ is as defined above
and Ab represents a leaving group, such as Cl, Br, —$OSO_2CF_3$ or

if appropriate in the presence of a catalyst and in the presence of an acid binder and in the presence of a solvent;

D) cyclic imines of the formula (I-c)

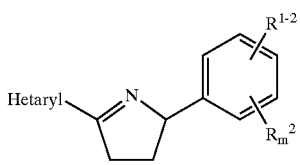

(I-c)

in which
Hetaryl is as defined above,
$R^2$ and m are as defined above,
$R^{1-2}$ represents one of the following groupings
(m-b) —B—Z—$D^1$
(n-b) —$Y^1$—$E^1$
in which
B and Z are as defined above,
$Y^1$ represents oxygen or sulphur and
$D^1$ and $E^1$ represent the grouping —$(CH_2)_p$—$(CR^7R^8)_q$—$(CH_2)_r$—G in which
$R^7$, $R^8$, G, p, q and r are as defined above
can be prepared by condensing cyclic imines of the formula (I-d)

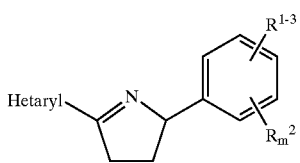

(I-d)

in which
Hetaryl is as defined above,
$R^2$ and m are as defined above and
$R^{1-3}$ represents one of the following groupings
(m-c) —B—Z—H
(n-c) —$Y^1$—H
in which
B, $Y^1$ and Z are as defined above,
with compounds of the formula (VII)

Ab—$(CH_2)_p$—$(CR^7R^8)_q$—$(CH_2)_r$—G    (VII), in which
$R^7$, $R^8$, G, p, q and r are as defined above and
Ab represents a leaving group;
E) cyclic imines of the formula (I-e)

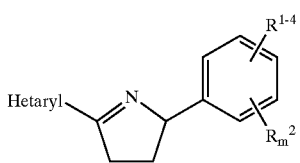

(I-e)

in which
Hetaryl is as defined above,
$R^2$ and m are as defined above and
$R^{14}$ represents a grouping containing the radical G, from the description of the compounds of the formula (I) according to the invention, where G represents one of the abovementioned groupings (e) to (k),
can be prepared by generally customary and known derivatizations of the corresponding keto derivatives, carboxylic acid derivatives or nitrites, i.e. compounds of the formula (I) in which G represents cyano or one of the groupings (a) to (d).

F) Cyclic imines of the formula (I-f)

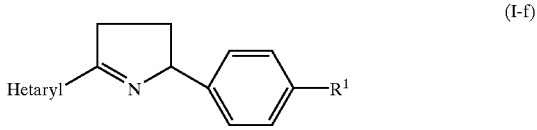

(I-f)

in which $R^1$ is as defined above can also be prepared by, in a first step,
α) reacting hetaryl methyl ketones of the formula (F-I)

(F-I)

in which
Hetaryl is as defined above
with dimethylmethyleneammonium chloride of the formula (F-II)

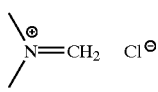

(F-II)

to give compounds of the formula (F-III)

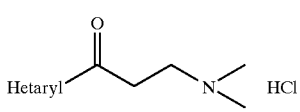

(F-III)

in which
Hetaryl is as defined above and reacting these, in a second step,
β) with benzyl cyanides of the formula (F-IV)

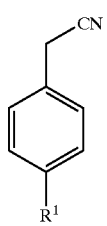

(F-IV)

in which $R^1$ is as defined above, to give compounds of the formula (F-V)

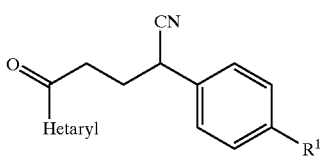
(F-V)

in which hetaryl is as defined above which, in the next step,

δ) are derivatized with aqueous sodium hydroxide solution/$H_2O_2$ to give compounds of the formula (F-VI)

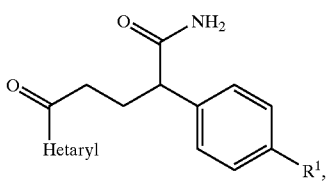
(F-VI)

in which $R^1$ and Hetaryl are as defined above, and cyclizing these, in a final step, γ) by reaction with PIFA (1,1-bis(trifluoroacetoxy) iodobenzene) of the formula (F-VII) or other known compounds having a comparable action, such as NaOBr or iodosobenzene

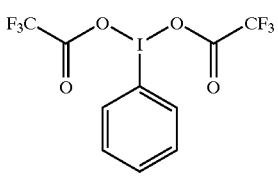
(F-VII)

to give cyclic imines of the formula (I-f) [see, for example, P. Radlich, L. R. Brown, Synthesis (1974) 290; R. Granados M. Alvarez, F. Lopez-Calahorra, M. Salas, Synthesis (1983), 329];

G) cyclic imines of the formula (I)

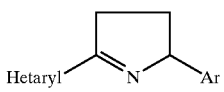
(I)

in which Ar and Hetaryl are as defined above can also be prepared by reacting, in a first step, α) arylbutyrolactams of the formula (X)

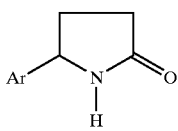
(X)

with hetarylcarbonyl chlorides, if appropriate in the presence of a base, to give compounds of the formula G (I)

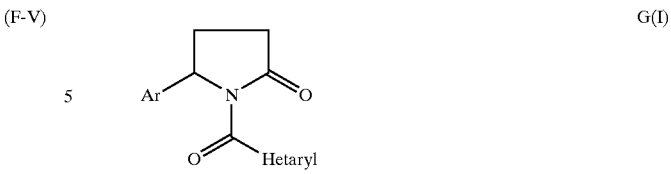
G(I)

and reacting these in a second step,

β) with methoxyqarbonylhetaryl, if appropriate in the presence of a base,

COOMe
|
Hetaryl to give compounds of the formula G (II)

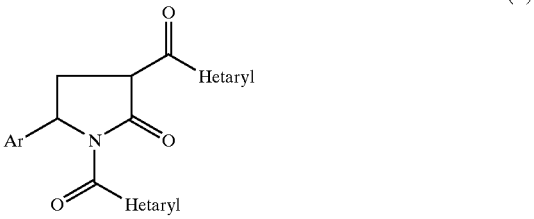
G(II)

which, in a final step,

δ) are reacted with HHal/glacial acid, where Hal represents Cl, Br and I, in particular Cl and Br, to give compounds of the formula (I)

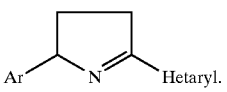

It is possible to vary step α) of process G. In this case, the amino function of the arylbutyrolactam (X) is, instead of a hetarylcarbonyl function, protected with a dialkylaminomethyl function or a vinyl function.

The dialkylaminomethyl function is then generated by reacting the lactams (X) with dialkylamine and formaldehyde, the vinylation can be carried out using, for example, acetylene (see, for example, textbooks of heterocyclochemistry). Step β) and δ) remain unchanged (see, for example, Jr. Org. Chem. 1998, 63, p. 1109 ff., J. Org. Chem. 1982, 47, p. 4165 ff and Oppi Briefs, 1995, 27, p. 510 ff.).

Furthermore, it has been found that the novel compounds of the formula (I) are tolerated well by plants and have very good activity as pesticides, in particular against arthropods in agriculture, but also against parasites in the keeping of useful animals and pets.

Formula (I) provides a general definition of the compounds according to the invention. Preferred substituents or ranges of the radicals listed in the formulae mentioned above and below are illustrated below.

Hetaryl preferably represents optionally mono- or polysubstituted unsaturated 5- or 6-membered heterocycles, for example thienyl, furanyl, thiazolyl, pyridyl, imidazolyl and triazolyl, which contain one or more heteroatoms from the group consisting of N, O and S and whose substituents can be selected, for example, from the group consisting of H, alkyl, alkoxy, halogen, cyano, halogenoalkyl, halogenoalkoxy, $S(O)_o$ $R^3$, carbamoyl, thiocarbamoyl, alkoximino and halogenoalkylthio.

Ar preferably represents the radical

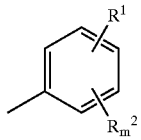

m preferably represents 0, 1, 2, 3.

$R^1$ preferably represents a substituent in the meta- or para-position from the group consisting of hydrogen, halogen or one of the groupings below
(l) —X—A
(m) —B—Z—D
(n) —Y—E.

$R^2$ preferably represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —$S(O)_oR^3$.

o preferably represents 0, 1 or 2.

$R^3$ preferably represents optionally fluorine- or chlorine-substituted $C_1$–$C_6$-alkyl.

X preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$-$C_4$-alkylsilylene.

A preferable represents phenyl, naphthyl or tetrahydronaphthyl, each of which is optionally mono- to tetrasubstituted by radicals from the list $W^1$, or represents 5- to 10-membered heterocycles which contain 1 or 2 aromatic rings, are optionally mono- to tetrasubstituted by radicals from the list $W^2$ and have 1 to 4 heteroatoms, which include 0 to 4 nitrogen atoms, 0 to 2 oxygen atoms and 0 to 2 sulphur atoms, (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl).

B preferably represents p-phenylene which is optionally mono- or disubstituted by radicals from the list $W^1$.

Z preferably represents oxygen or sulphur.

D preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, in each case optionally halogen-, $C_1$–$C_4$-alkyl-, $C_2$–$C_4$-alkenyl-, $C_2$–$C_4$-halocenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, represents in each case optionally halogen- or $C_1$–$C_4$-alkyl-substituted $C_5$–$C_8$-cycloalkenyl or $C_5$–$C_8$-cycloalkenyl-$C_1$–$C_4$-alkyl, represents in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or 5- to 6-ring-membered hetaryl-$C_1$–$C_6$-alkyl having 1 or 2 heteroatoms from the group consisting of nitrogen, oxygen and sulphur (in particular furylmethyl, thienylmethyl, pyrrolylmethyl, oxazolylmethyl, isoxazolylmethyl, thiazolylmethyl or pyridylmethyl), represents —CO—$R^4$, —CO—$NR^5R^6$ or represents the grouping

Z and D also preferably together represent in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl.

Y preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halocenoalkenyl, optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, represents optionally halogen- or $C_1$–$C_4$-alkyl-substituted $C_5$–$C_8$-cycloalkenyl, represents phenyl which is optionally mono- to tetrasubstituted by radicals from the list $W^1$ or represents 5- to 6-membered hetaryl which is in each case optionally mono- to tetrasubstituted by radicals from the list $W^2$ and has 1 or 2 heteroatoms from the group consisting of nitrogen, oxygen and sulphur (in particular furyl, thienyl, pyrrolyl, oxazolyl, isoxazolyl, thiazolyl or pyridyl) or represents the grouping

$R^4$ preferably represents $C_1$–$C_{12}$-alkyl, $C_1$–$C_{12}$-alkoxy, $C_2$–$C_{12}$-alkenyl, $C_2$–$C_{12}$-alkenyloxy, in each case optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy or represents phenyl or naphthyl, each of which is optionally mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

$R^5$ preferably represents hydrogen or $C_1$–$C_{12}$-alkyl.

$R^6$ preferably represents $C_1$–$C_{12}$-alkyl, $C_1$–$C_{12}$-halogenoalkyl, in each case optionally halogen-, $C_1$–$C_4$-alkyl-, $C_2$–$C_4$-alkenyl, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl -or represents phenyl or phenyl-$C_1$–$C_6$-alkyl, each of which is optionally mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

p, q and r preferably independently of one another represent 0, 1, 2 or 3, their sum being smaller than 6.

$R^7$ and $R^8$ independently of one another preferably represent hydrogen or $C_1$–$C_4$-alkyl.

G preferably represents cyano, represents a 5- or 6-membered heterocycle which is optionally mono- to trisubstituted by halogen, $C_1$–$C_4$-alkyl or $C_1$–$C_4$-halogenoalkyl and optionally substituted at the point of linkage by the radical $R^9$ and has 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) or one of the following groupings:

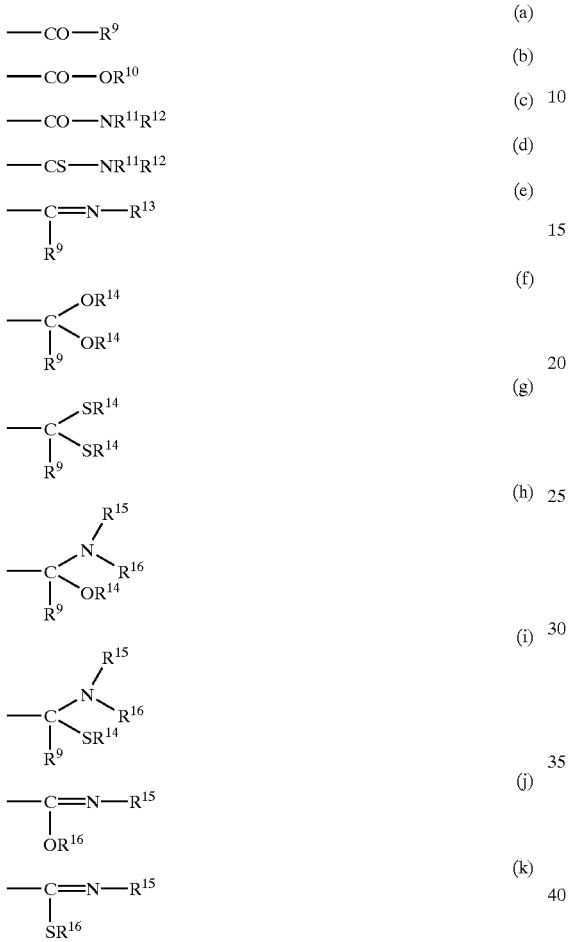

$R^9$ preferably represents hydrogen, $C_1$–$C_6$-alkyl, $C_2$–$C_6$-alkenyl, $C_1$–$C_4$-halogenoalkyl, $C_2$–$C_6$-halogenoalkenyl, optionally halogen-, $C_1$–$C_4$-alkyl- or $C_1$–$C_4$-halogenoalkyl-substituted $C_3$–$C_6$-cycloalkyl or represents phenyl which is optionally mono- to pentasubstituted by $C_1$–$C_4$-alkylcarbonylamino, $C_1$–$C_4$-alkylcarbonyl-$C_1$–$C_4$-alkylamino and/or by radicals from the list $W^3$.

$R^{10}$ preferably represents hydrogen, $C_1$–$C_4$-alkyl, $C_2$–$C_6$-alkenyl, $C_1$–$C_4$-halogenoalkyl, $C_2$–$C_6$-halogenoalkenyl, in each case optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represents $C_6$–$C_{10}$-aryl-$C_1$–$C_4$-alkyl (in particular phenyl-$C_1$–$C_4$-alkyl or naphthyl-$C_1$–$C_4$-alkyl) which is optionally mono- to tetra-substituted by radicals from the list $W^3$.

$R^{11}$ and $R^{12}$ independently of one another preferably represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, in each case optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl, represent phenyl or phenyl-$C_1$–$C_4$-alkyl, each of which is optionally mono- to pentasubstited by radicals from the list $W^3$, represent —$OR^{10}$ or —$NR^9R^{10}$ or together represent an alkylene chain having 4 to 6 members in which optionally one methylene group is replaced by oxygen.

$R^{13}$ preferably represents —$OR^{10}$, —$NR^9R^{10}$ or —$N(R^9)$—$COOR^{10}$.

$R^{14}$, $R^{15}$ and $R^{16}$ independently of one another preferably represent $C_1$–$C_6$-alkyl.

$W^1$ preferably represents hydrogen, halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_2$–$C_6$-halogenoalkenyloxy, $C_1$–$C_6$-alkylcarbonyl, $C_1$–$C_{16}$-alkoxycarbonyl, pentafluorothio or —$S(O)_oR^3$.

$W^2$ preferably represents halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenalkoxy, $C_1$–$C_6$-alkylcarbonyl, $C_1$–$C_{16}$-alkoxycarbonyl, pentafluorothio, —$S(O)_oR^3$ or —$C(R^9)$=$N$—$R^{13}$.

$W^3$ preferably represents halogen, cyano, nitro, $C_1$–$C_4$-alkyl, $C_1$–$C_4$-alkoxy, $C_1$–$C_4$-halogenoalkyl, $C_1$–$C_4$-halogenoalkoxy, di-$C_1$–$C_4$-alkylamino, —$S(O)_oR^3$, —$COOR^{17}$ or —$CONR^{18}R^{19}$.

$R^{17}$ preferably represents hydrogen, $C_1$–$C_4$-alkyl, $C_1$–$C_4$-halogenoalkyl, optionally halogen-, $C_1$–$C_4$-alkyl- or $C_1$–$C_4$-halogenoalkyl-substituted $C_3$–$C_7$-cycloalkyl or represents phenyl which is optionally mono- to pentasubstituted by radicals from the list $W^4$.

$R^{18}$ and $R^{19}$ independently of one another preferably represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, in each case optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represent phenyl or phenyl-$C_1$–$C_4$-alkyl, each of which is optionally mono- to pentasubstituted by radicals from the list $W^4$, represent —$OR^{14}$ or —$NR^{15}R^{16}$ or together represent an alkylene chain having 4 to 6 members in which optionally one methylene group is replaced by oxygen.

$W^4$ preferably represents halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, di-$C_1$–$C_4$-alkylamino, $C_1$–$C_6$-alkoxycarbonyl, di-$C_1$–$C_6$-alkylaminocarbonyl or —$S(O)_oR^3$.

In the preferred ranges, halogen represents, for example, Cl, F. Br and iodine, in particular F, Cl and Br.

Hetaryl particularly preferably represents five- or six-membered monocyclic unsaturated heterocyclyls, for example thienyl, furanyl, thiazolyl, imidazolyl, pyridyl and triazolyl, which contain one to three heteroatoms from the group consisting of N, O or S and which are optionally substituted by one to three substituents from the group consisting of H, alkyl, alkoxy, halogen, for example F, Cl and Br, halogenoalkyl, halogenoalkoxy, halogenoalkylthio, where halogen represents, for example, F or Cl, $S(O)_oR^{3'}$, —$CONH_2$, $CSNH_2$, —$CH$=$N$—$O(alkyl)$ and cyano.

Ar particularly preferably represents the radical

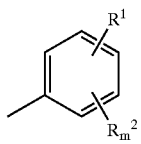

m particularly preferably represents 0, 1 or 2.

$R^1$ particularly preferably represents a substituent in the meta- or para-position from the group consisting of hydrogen, fluorine, chlorine, bromine, iodine or one of the groupings below
(l) —X—A
(m) —B—Z—D
(n) —Y—E.

$R^2$ particularly preferably represents hydrogen, fluorine, chlorine, bromine, iodine, cyano, nitro, $C_1$–$C_{16}$-alkyl, $C_1$–$C_{16}$alkoxy, in each case fluorine- or chlorine-substituted $C_1$–$C_6$-alkyl or $C_1$–$C_6$-alkoxy, represents $C_1$–$C_8$-alkoxy-$C_1$–$C_8$-alkoxy, or —S(O)$_o$R$^3$.

o particularly preferably represents 0, 1 or 2.

$R^3$ particularly preferably represents, $C_1$–$C_4$-alkyl or in each case fluorine- or chlorine-substituted methyl or ethyl.

X particularly preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene.

A particularly preferably represents phenyl, naphthyl or tetrahydronaphthyl, each of which is optionally mono- to trisubstituted by radicals from the list $W^1$, or represents 5- to 10-membered heterocyclyls which contain 1 or 2 aromatic rings, are in each case optionally mono- to trisubstituted by radicals from the list $W^2$ and have 1 to 4 heteroatoms including 0 to 4 nitrogen atoms, 0 to 2 oxygen atoms and 0 to 2 sulphur atoms, (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl).

B particularly preferably represents p-phenylene which is optionally mono- or disubstituted by radicals from the list $W^1$.

Z particularly preferably represents oxygen or sulphur.

D particularly preferably represents hydrogen, $C_1$–$C_{16}$-alkyl, $C_2$–$C_{16}$-alkenyl, $C_2$–$C_6$-alkinyl, in each case fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is optionally substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl, fluorine-, chlorine- or bromine-substituted phenyl or styryl, represents in each case optionally fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, represents phenyl-$C_1$–$C_4$-alkyl, naphthyl-$C_1$–$C_4$-alkyl, tetrahydronaphthyl-$C_1$–$C_6$-alkyl or 5- or 6-ring-membered heterocyclyl-$C_1$–$C_4$-alkyl having 1 or 2 heteroatoms from the group consisting of nitrogen, oxygen and sulphur, in particular furylmethyl, thienylmethyl, pyrrolylmethyl, oxazolylmethyl, isoxazolylmethyl, thioazolylmethyl or pyridylmethyl) each of which is optionally substituted by nitro, fluorine, chlorine, bromine, $C_1$–$C_6$-alkyl, $C_1$–$C_6$-alkoxy, fluorine- or chlorine-substituted $C_1$–$C_4$-alkyl or $C_1$–$C_4$-alkoxy, represents —CO—R$^4$, —CO—NR$^5$R$^6$, or the grouping

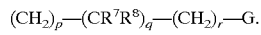

Z and D also particularly preferably together represent phenoxy-$C_1$–$C_3$-alkyl which is optionally substituted by nitro, fluorine, chlorine, bromine, $C_1$–$C_4$-alkyl, $C_1$–$C_4$-alkoxy, fluorine- or chlorine-substituted $C_1$–$C_4$-alkyl or $C_1$–$C_4$-alkoxy., Y particularly preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E particularly preferably represents hydrogen, $C_1$–$C_{16}$-alkyl, $C_2$–$C_{16}$-alkenyl, $C_2$–$C_6$-alkinyl, in each case fluorine- or chlorine-substituted $C_1$–$C_4$-alkyl or $C_2$–$C_4$-alkenyl, represents $C_3$–$C_6$-cycloalkyl which is optionally substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl, fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl, represents phenyl which is optionally mono- to trisubstituted by radicals from the list $W^1$ or represents 5- or 6-membered heterocyclyls which are in each case mono- or disubstituted by radicals from list $W^2$ and have 1 or 2 heteroatoms from the group consisting of nitrogen, oxygen and sulphur (in particular furyl, thienyl, pyrrolyl, oxazolyl, isoxazolyl, thiazolyl or pyridyl) or represent the grouping

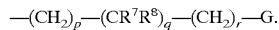

$R^4$ particularly preferably represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy oder $C_3$–$C_6$-cycloalkyl-$C_1$–$C_2$-alkyloxy, each of which is optionally substituted by fluorine, chlorine, $C_1$–$C_3$-alkyl fluorine- or chlorine-substituted $C_1$–$C_2$-alkyl or $C_2$–$C_3$-alkenyl, or represents phenyl which is optionally mono- or disubstituted by fluorine, chlorine, bromine, iodine, $C_1$–$C_4$-alkyl, $C_1$–$C_4$-alkoxy, fluorine- or chlorine-substituted $C_1$–$C_3$-alkyl or $C_1$–$C_4$-alkoxy.

$R^5$ particularly preferably represents hydrogen or $C_1$–$C_4$-alkyl.

$R^6$ particularly preferably represents $C_1$–$C_4$-alkyl or represents phenyl or benzyl, each of which is optionally mono- or disubstituted by fluorine, chlorine, bromine, $C_1$–$C_4$-alkyl, fluorine- or chlorine-substituted $C_1$–$C_4$-alkyl or $C_1$–$C_4$-alkoxy.

p, q and r particularly preferably independently of one another represent 0, 1, 2 or 3, their sum being smaller than 6.

$R^7$ and $R^8$ independently of one another particularly preferably represent hydrogen or $C_1$–$C_4$-alkyl.

G particularly preferably represents cyano, represents 5- or 6-membered heterocyclyl which is optionally mono- to trisubstituted by fluorine, chlorine, bromine, $C_1$–$C_4$-alkyl or by fluorine- or chlorine-substituted $C_1$–$C_4$-alkyl and optionally at the point of linkage by the radical $R^9$ and has 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) or one of the following groupings:

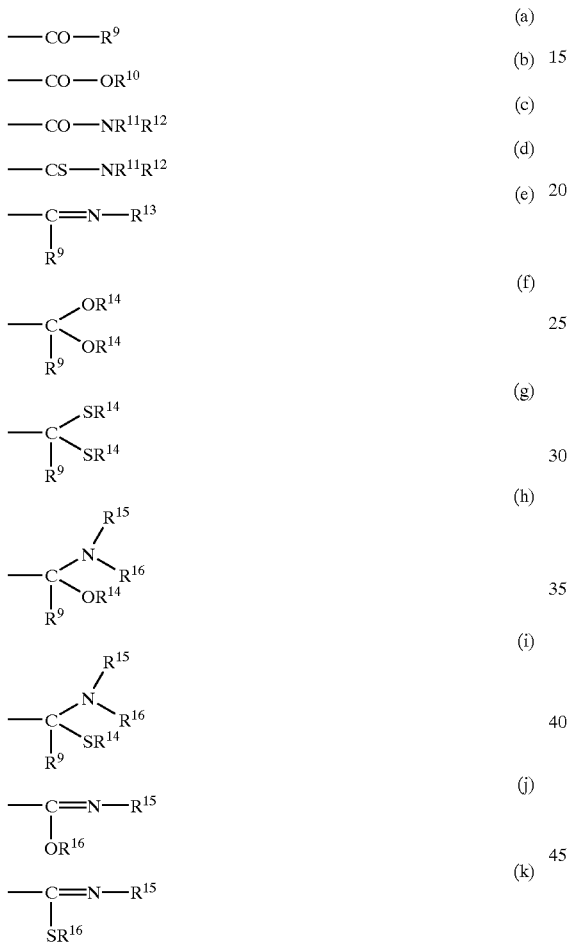

$R^9$ particulary preferably represents hydrogen, $C_1$–$C_6$-alkyl, $C_2$–$C_6$-alkenyl, in each case florine- or chlorine-substituted $C_1$–$C_4$-alkyl or $C_1$–$C_6$-alkenyl, $C_3$–$C_6$-cycloalkyl which is optionally substituted by fluorine, chlorine, $C_1$–$C_4$-alkyl, fluorine- or chlorine-substituted $C_1$–$C_4$-alkyl or represents phenyl which is optionally mono- to trisubstituted by $C_1$–$C_4$-alkylcarbonylamino, $C_1$–$C_4$-alkylcarbonyl-$C_1$–$C_4$-alkylamino and/or radicals from the list $W^3$.

$R^{10}$ particularly preferably represents hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl, fluorine- or chlorine-substituted $C_1$–$C_4$-alkyl, or represents phenyl-$C_1$–$C_4$-alkyl or naphthyl-$C_1$–$C_4$-alkyl, each of which is optionally mono- to trisubstituted by radicals from the list $W^3$.

$R^{11}$ and $R^{12}$ independently of one another particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl, fluorine- or a chlorine-substituted $C_1$–$C_4$-alkyl, represent phenyl or phenyl-$C_1$–$C_4$-alkyl, each of which is optionally mono- to trisubstituted by radicals from the list $W^3$, represent —$OR^{10}$ or —$NR^9R^{10}$ or toether —$(CH_2)_5$—, —$(CH_2)_6$— or —$(CH_2)_2$—O—$(CH_2)_2$—

$R^{13}$ particularly preferably represents —$OR^{10}$, —$NR^9R^{10}$ or —$N(R^9)$—$COOR^{10}$.

$R^{14}$, $R^{15}$ and $R^{16}$ independently of one another particularly preferably represent $C_1$–$C_4$-alkyl.

$W^1$ particularly preferably represents hydrogen, fluorine, chlorine, bromine, iodine, cyano, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_oR^3$.

$W^2$ particularly preferably represents fluorine, chlorine, bromine, cyano, formyl, nitro, $C_1$–$C_4$-alkyl, $C_1$–$C_4$-alkoxy, in each case fluorine or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_oR^3$ or —$C(R^9)$=N—$R^{13}$.

$W^3$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents di-$C_1$–$C_4$-alkylamino, —$S(O)_oR^3$, —$COOR^{17}$ or —$CONR^{18}R^{19}$.

$R^{17}$ particularly preferably represents hydrogen, $C_1$–$C_4$-alkyl, fluorine- or chlorine-substituted $C_1$–$C_4$-alkyl, $C_3$–$C_6$-cycloalkyl which is optionally substituted by fluorine, chlorine, $C_1$–$C_4$-alkyl, fluorine- or chlorine-substituted $C_1$–$C_4$-alkyl or represents phenyl which is optionally mono- to trisubstituted by radicals from the list $W^4$.

$R^{18}$ and $R^{19}$ independently of one another particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl, fluorine- or chlorine-substituted $C_1$–$C_4$-alkyl, or represent phenyl or phenyl-$C_1$–$C_4$-alkyl, each of which is optionally mono- to trisubstituted by radicals from the list $W^4$, represent —$OR^{14}$ or —$NR^{15}R^{16}$ or together represent —$(CH_2)_5$—, —$(CH_2)_6$— or —$(CH_2)_2$—O—$(CH_2)_2$—.

$W^4$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_oR^3$.

Hetaryl very particularly preferably represents thienyl, pyridyl, thiazolyl or furanyl groups optionally mono- to disubstituted by substituents from the group consisting of H, F, Cl, Br, cyano, CH₃, OCH₃, OCF₃, SCF₃, S(O)ₒR³ and CF₃.

Ar very particularly preferably represents the radical

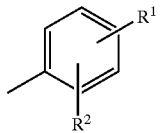

R¹ very particularly preferably represents a substituent in the meta- or para-position from the group consisting of hydrogen, fluorine, chlorine, bromine, iodine or one of the groupings below —X—A  (l)

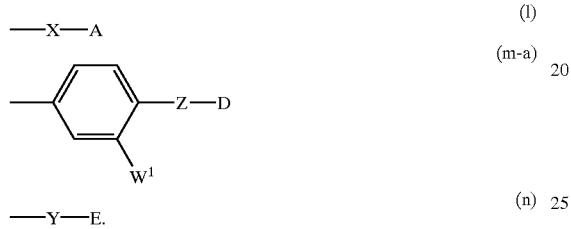

—Y—E.  (n)

R² very particularly preferably represents hydrogen, fluorine, chlorine, bromine, methyl, ethyl, methoxy, ethoxy, methylthio, ethylthio, trifluoromethyl, difluoromethoxy, trifluoromethoxy or trifluoromethylthio.

o very particularly preferably represents 0, 1 or 2, in particular 0 or 2.

R³ very particularly preferably represents methyl, ethyl, n-propyl, isopropyl, difluoromethyl or trifluoromethyl.

X very particularly preferably represents a direct bond, oxygen, sulphur, carbonyl, —CH₂—, —(CH₂)₂—, —CH=CH— (E or Z), —C≡C—, —CH₂O—, —(CH₂)₂O—, —CH(CH₃)O—, —OCH₂—, —O(CH₂)₂—, —SCH₂—, —S(CH₂)₂—, —SCH(CH₃)—, C₁-C₄-alkylenedioxy, in particular —OCH₂O—, —O(CH₂)₂O— or —OCH(CH₃)O—.

A very particularly preferably represents phenyl which is optionally mono- or disubstituted by radicals from the list W¹ or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is optionally mono- or disubstituted by radicals from the list W².

Z very particularly preferably represents oxygen or sulphur.

D very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl, cyclohexyl, cyclopropylmethyl, cyclobutylmethyl, cyclopentylmethyl or cyclohexylmethyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl₂, phenyl, styryl, fluorine-, chlorine- or bromine-substituted phenyl or 4-chlorostyryl, represents cyclopentenyl, cyclohexenyl, cyclohexenylmethyl or cyclopentenylmethyl, each of which is optionally substituted by fluorine, chlorine, methyl, ethyl, n-propyl, isopropyl, n-butyl, isobutyl, sec-butyl or tert-butyl, represents benzyl phenethyl naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is optionally mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—R⁴, —CO—NR⁵R⁶ or the grouping —(CH₂)ₚ—(CR⁷R⁸)_q—(CH₂)ᵣ—G.

Z and D also very particularly preferably together represent phenoxymrethyl which is optionally mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy.

Y very particularly preferably represents a direct bond, oxygen, sulphur, carbonyl, —CH₂—, —(CH₂)₂—, —CH=CH— (E or Z), —C≡C—, —CH₂O—, —(CH₂)₂O—, —CH(CH₃)O—, —OCH₂—, —O(CH₂)₂—, —SCH₂—, —S(CH₂)₂—, —SCH(CH₃)—, C₁-C₄-alkylenedioxy, in particular —OCH₂O— or —O(CH₂)₂O— or represents p-phenylene which is optionally monosubstituted by a radical from the list W¹.

E very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl or cyclohexyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl₂, phenyl, styryl, in each case fluorine-, chlorine- or bromine-substituted phenyl or by 4-chlorostyryl, represents cyclopentenyl or cyclohexenyl, each of which is optionally substituted by fluorine, chlorine, methyl, ethyl, n-propyl, isopropyl, n-butyl, isobutyl, sec-butyl or tert-butyl, represents phenyl which is optionally mono- or disubstituted by radicals from the list W¹, represents furyl, thienyl, pyrrolyl, oxazolyl, isoxazolyl, thiazolyl or pyridyl, each of which is optionally mono- or disubstituted by radicals from the list $W^2$, or represents the grouping

—(CH$_2$)$_p$—(CR$^7$R$^8$)$_q$—(CH$_2$)$_r$—G.

$R^4$ very particularly preferably represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl.

$R^5$ very particularly preferably represents hydrogen.

$R^6$ very particularly preferably represents methyl, ethyl or phenyl which is optionally monosubstituted by chlorine.

p, q and r very particularly preferably independently of one another represent 0, 1, 2 or 3, their sum being smaller than 4.

$R^7$ and $R^8$ independently of one another very particularly preferably represent hydrogen, methyl, ethyl, n-propyl, isopropyl, n-butyl, isobutyl, sec-butyl, tert-butyl.

G very particularly preferably represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is optionally mono- to trisubstituted by fluorine, chlorine, bromine, methyl, ethyl, n-propyl, isopropyl or trifluoromethyl and optionally at the point of linkage by the radical $R^9$ or represents one of the following groupings:

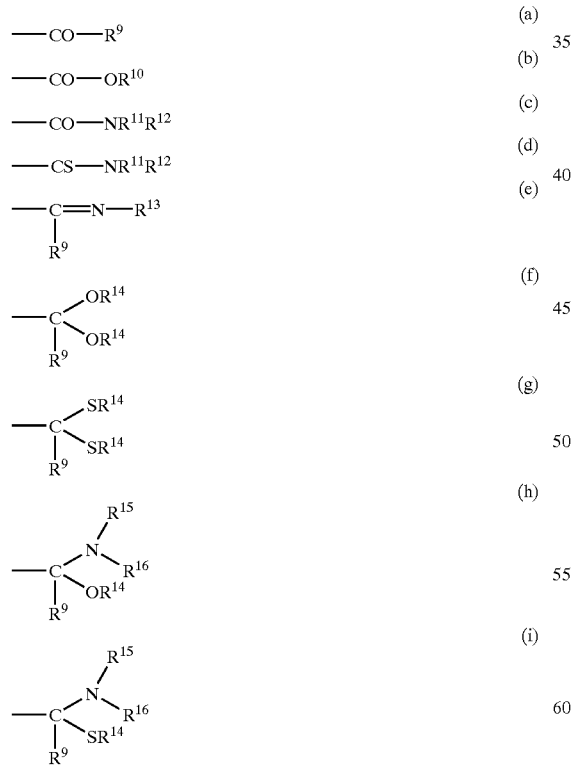

$R^9$ very particularly preferably represents hydrogen, methyl, ethyl, n-propyl, isopropyl, n-butyl, isobutyl, sec-butyl, tert-butyl, the isomeric pentyls, the isomeric hexyls, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, C$_3$–C$_6$-alkenyl; C$_3$–C$_6$-alkenyl which is mono to trisubstituted by fluorine or chlorine, represents cyclopropyl, cyclopentyl or cyclohexyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents phenyl which is optionally mono- or disubstituted by methylcarbonylamino, ethylcarbonylamino, methylcarbonyl-methylamino and/or radicals from the list $W^3$.

$R^{10}$ very particularly preferably represents hydrogen, methyl, ethyl, n-propyl, isopropyl, n-butyl, isobutyl, sec-butyl, tert-butyl, —CH$_2$CF$_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents benzyl or phenethyl, each of which is optionally mono- or disubstituted by radicals from the list $W^3$.

$R^{11}$ and $R^{12}$ independently of one another very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine, chlorine, methyl, ethyl, n-propyl, isopropyl or trifluoromethyl, represent phenyl, benzyl or phenethyl, each of which is optionally mono- or disubstituted by radicals from the list $W^3$, represent —OR$^{10}$ or —NR$^9$R$^{10}$.

$R^{13}$ very particularly preferably represents —OR$^{10}$, —NR$^9$R$^{10}$ or —N(R$^9$)—COOR$^{10}$.

$R^{14}$, $R^{15}$ and $R^{16}$ independently of one another particularly preferably represent methyl, ethyl, n-propyl or isopropyl.

$W^1$ very particularly preferably represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, trifluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl or —S(O)$_o$R$^3$.

$W^2$ very particularly preferably represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=N—OC$_3$H$_7$, —C(C$_2$H$_5$)=N—OCH$_3$, —C(C$_2$H$_5$)=N—OC$_2$H$_5$ or —C(C$_2$H$_5$)=N—OC$_3$H$_7$.

$W^3$ very particularly preferably represents fluorine, chlorine, cyano, nitro, methyl, ethyl, methoxy, ethoxy, methylthio, trifluoromethyl, trifluoromethoxy, trifluoromethylthio, dimethylamino, diethylamino, —COOR$^{17}$ or —CONR$^{18}$R$^{19}$.

$R^{17}$ very particularly preferably represents hydrogen, methyl, ethyl, n-propyl, isopropyl, tert-butyl, —CH$_2$CF$_3$, represents cyclopropyl, cyclopentyl or cyclohexyl, each of which is optionally mono- or disubstituted by fluorine, chlorine, methyl, ethyl, n-propyl, isopropyl or —CF$_3$, or represents phenyl which is optionally mono- or disubstituted by radicals from the list $W^4$.

$R^{18}$ and $R^{19}$ independently of one another very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine or chlorine, represent phenyl, benzyl or phenethyl, each of which is optionally mono- or disubstituted by radicals from the list $W^4$, represent —OR$^{14}$ or —NR$^{15}$R$^{16}$.

$W^4$ very particularly preferably represents fluorine, chlorine, bromine, cyano, nitro, methyl, ethyl, tert-butyl, methoxy, ethoxy, methylthio, trifluoromethyl, trifluoromethoxy or trifluoromethylthio.

Preference is furthermore given to compounds of the formula (I-a)

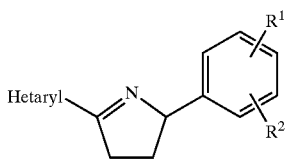

(I-a)

in which

Hetaryl has the general, preferred, particularly preferred or very particularly preferred meanings mentioned above, $R^2$ has the general, preferred, particularly preferred or very particularly preferred meanings mentioned above, $R^1$ represents hydrogen or phenyl which is mono- to disubstituted by radicals from the list $W^1$ or represents one of the following groupings (m-b) —B—O—D (l) —Y—E, B represents p-phenylene which is optionally mono-substituted by a radical from the list $W^1$, Y represents a direct bond or represents p-phenylene which is optionally mono- or disubstituted by radicals from the list $W^1$ and D and E have the very particularly preferred meanings mentioned above, where G represents cyano or one of the following groupings (a) —CO—R$^9$

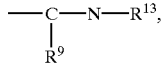

(e)

in which $R^9$ and $R^{13}$ have the general, preferred, particularly preferred or very particularly preferred meanings mentioned above and $W^1$ has the general, preferred, particularly preferred or very particularly preferred meaning mentioned above.

Preference is furthermore given to compounds of the formula (I-f)

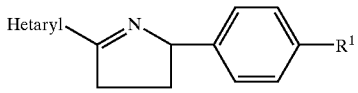

(I-f)

in which

Hetaryl represents thienyl, thiazolyl, pyridyl or furanyl groups which are optionally mono- or disubstituted by substituents from the group consisting of H, F, Cl, cyano, OCF$_3$, OCH$_3$, SCF$_3$, CH$_3$, S(O)$_o$R$^3$ and CF$_3$, and o represents 0, 1 or 2, and $R^1$ represents hydrogen or
a) phenoxy, benzyloxy or phenyl, mono- or disubstituted by radicals from the lists $W^2$ or $W^1$,
b) hetaryl (in particular furyl, thienyl, pyrrolyl, oxazolyl, isoxazolyl, thiazolyl or pyridyl, specifically thienyl), mono- or disubstituted by radicals from the list $W^2$,
c) alkyloxy, alkenyloxy,
where $W^1$ and $W^2$ have the very particularly preferred meanings mentioned above, and $R^3$ represents CH$_3$, CHF$_2$, CF$_3$.

Preference is furthermore given to compounds of the formula (I-g)

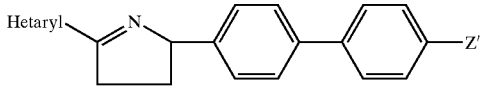

(I-g)

in which

Hetaryl represents thienyl, thiazolyl, pyridyl or furanyl groups which are optionally mono- or disubstituted by substituents from the group consisting of H, F, Cl, cyano, OCF$_3$, SCF$_3$, CH$_3$, OCH$_3$ and CF$_3$, and Z' represents hydrogen, fluorine, bromine, Cl, cyano, methyl, ethyl, n-prbpyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=N—OC$_3$H$_7$, —C(C$_2$H$_5$)=N—OCH$_3$, —C(C$_2$H$_5$)=N—OC$_3$H$_7$,

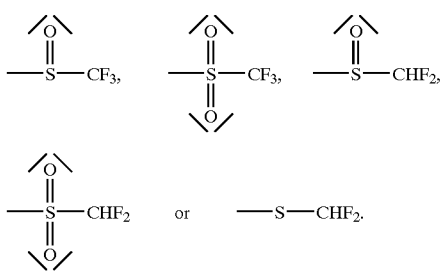

Preference is furthermore given to the compounds. of the formula (I-f-1) listed in Table 1.

TABLE 1

(I-f-1)

| Example No. | R¹ |
|---|---|
| I-1 | 4-isopropylphenyl |
| I-2 | 3,5-dichlorophenyl |
| I-3 | 4-fluorophenyl |
| I-4 | 4-chlorophenyl |
| I-5 | thien-3-yl |
| I-6 | 5-methyl-thiophen-2-yl-CH=N-O-CH₃ |
| I-7 | 4-OCF₃-phenyl |
| I-8 | —Br |
| I-9 | 5-methyl-2,2-difluoro-1,3-benzodioxol |

TABLE 1-continued (I-f-1)

| Example No. | R¹ |
|---|---|
| I-10 | 3-methyl-6-OCF₃-2-fluorophenyl (substituted) |
| I-11 | 3-CF₃-phenyl |
| I-12 | 4-CF₃-phenyl |
| I-13 | 2-CHO-phenyl |
| I-14 | 4-CHO-phenyl |
| I-15 | 4-COOH-phenyl |
| I-16 | 2-CH₃-3-F-phenyl |
| I-17 | benzothiophen-2-yl |
| I-18 | 2,2,3,3-tetrafluoro-1,4-benzodioxin |
| I-19 | 3,5-bis(CF₃)-phenyl |
| I-20 | H |
| I-21 | 3-acetylphenyl |

TABLE 1-continued (I-f-1)

[Structure: 2-(thiophen-2-yl)-5-(4-R¹-phenyl)-3,4-dihydro-2H-pyrrole]

| Example No. | R¹ |
|---|---|
| I-22 | 4-methylphenyl-CH=N-OCH₃ |
| I-23 | 3-methylphenyl-C(=O)-CH₂CH₃ |
| I-24 | 4-methylphenyl-C(=O)-CH₂CH₃ |
| I-25 | 4-methylphenyl-CH=N-OCH₂CH₃ |
| I-26 | 4-methylphenyl-S-CH(CH₃)₂ |
| I-27 | 4-methylphenyl-O-CH(CH₃)₂ |
| I-28 | 1-methylnaphthyl |
| I-29 | 4-methylphenyl-C(CH₃)=N-OCH₂CH₃ |
| I-30 | 4-methylphenyl-C(CH₂CH₃)=N-OCH₃ |
| I-31 | 4-methylphenyl-CH₂-CH(CH₃)₂ |
| I-32 | 4-methylphenyl-CH₂-S-CH(CH₃)₂ |
| I-33 | 4-methylbiphenyl |
| I-34 | 4-methylphenyl-(CH₂)₄-CH₃ |
| I-35 | 4-methylphenyl-CH₂-O-(4-chlorophenyl) |
| I-36 | 4-methylphenyl-O-CH₂-(4-chlorophenyl) |
| I-37 | 4-methylphenyl-CH₃ |
| I-38 | 4-methylphenyl-OCH₃ |
| I-39 | 4-methylphenyl-C(=O)-CH₃ |
| I-40 | —(CH₂)₃—CH₃ |
| I-41 | 4-methylphenyl-Br |
| I-42 | 4-methylphenyl-SCF₃ |
| I-43 | 4-methylphenyl-S(=O)-CF₃ |

TABLE 1-continued
(I-f-1)
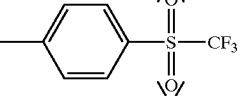
| Example No. | R¹ |
|---|---|
| I-44 | 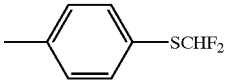 |
| I-45 | 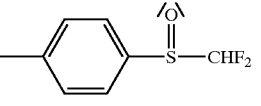 |
| I-46 | 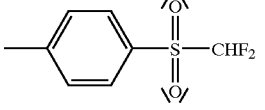 |
| I-47 | 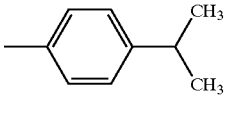 |
Preference furthermore given to the compounds of the formula (I-f-2) listed in Table 2
TABLE 2
(I-f-2)
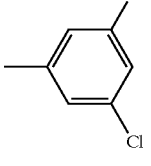
| Example No. | R¹ |
|---|---|
| I-48 | 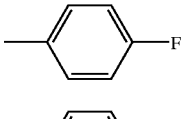 |
| I-49 | 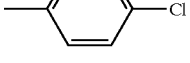 |
| I-50 | 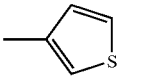 |
| I-51 | 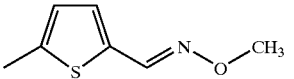 |
TABLE 2-continued
(I-f-2)
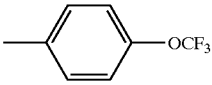
| Example No. | R¹ |
|---|---|
| I-52 | 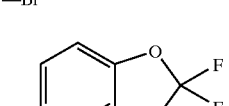 |
| I-53 | 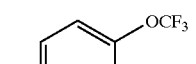 |
| I-54 | 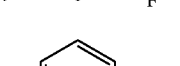 |
| I-55 | —Br |
| I-56 | 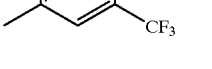 |
| I-57 | 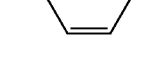 |
| I-58 | 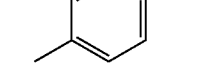 |
| I-59 | 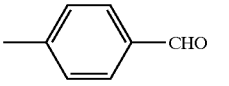 |
| I-60 |  |
| I-61 | —⟨C₆H₄⟩—CHO |
| I-62 | —⟨C₆H₄⟩—COOH |
| I-63 | 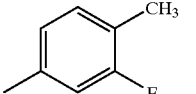 |
| I-64 | (benzothiophene) |

TABLE 2-continued
(I-f-2)
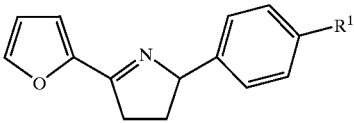
| Example No. | R¹ |
|---|---|
| I-65 | 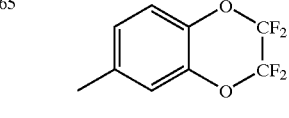 |
| I-66 | 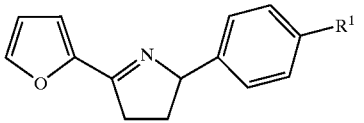 |
| I-67 | H |
| I-68 | 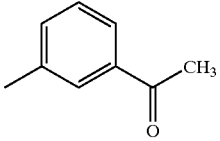 |
| I-69 | 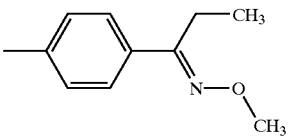 |
| I-70 | 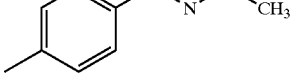 |
| I-71 | 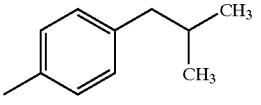 |
| I-72 | 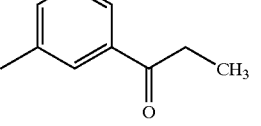 |
| I-73 | 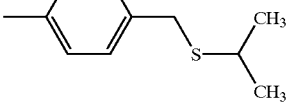 |
| I-74 | 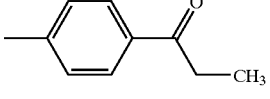 |
| I-75 | 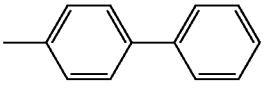 |
TABLE 2-continued
(I-f-2)
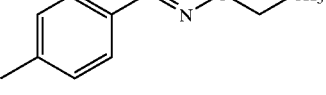
| Example No. | R¹ |
|---|---|
| I-76 |  |
| I-77 | 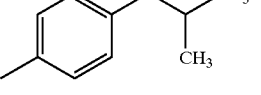 |
| I-78 | 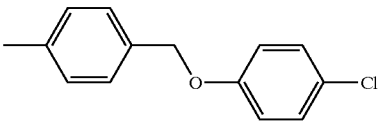 |
| I-79 | 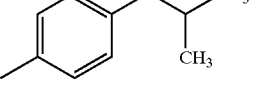 |
| I-80 | 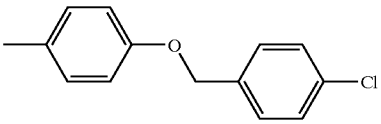 |
| I-81 | 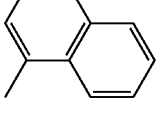 |
| I-82 | 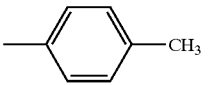 |
| I-83 | 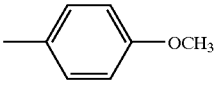 |
| I-84 | 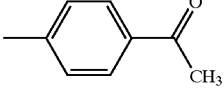 |
| I-85 |  |
| I-86 |  |

TABLE 2-continued
(I-f-2)
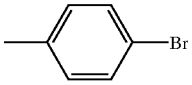
| Example No. | R¹ |
|---|---|
| I-87 | —(CH₂)₃—CH₃ |
| I-88 | 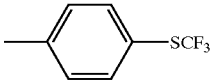 |
| I-89 | 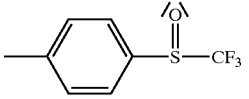 |
| I-90 | 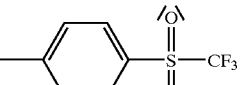 |
| I-91 | 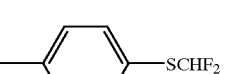 |
| I-92 | 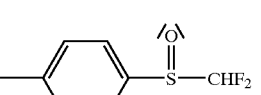 |
| I-93 | 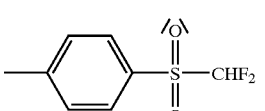 |
| I-94 | 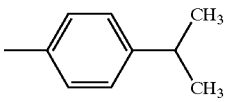 |
Preference is furthermore given to the compounds of the formula (I-f-3) listed in Table 3
TABLE 3
(I-f-3)
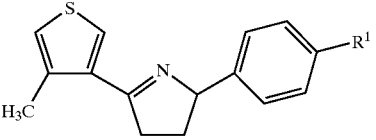
| Example No. | R¹ |
|---|---|
| I-95 |  |
TABLE 3-continued
(I-f-3)
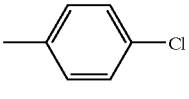
| Example No. | R¹ |
|---|---|
| I-96 | 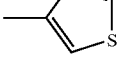 |
| I-97 | 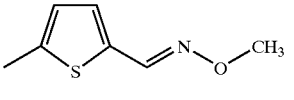 |
| I-98 | 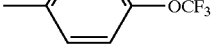 |
| I-99 | 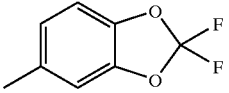 |
| I-100 | 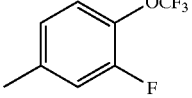 |
| I-101 | 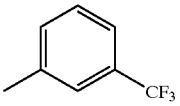 |
| I-102 | —Br |
| I-103 | 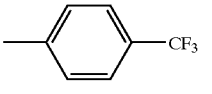 |
| I-104 | 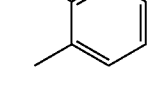 |
| I-105 | 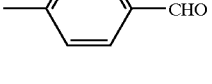 |
| I-106 |  |
| I-107 |  |
| I-108 |  |

TABLE 3-continued
(I-f-3)
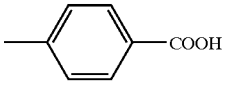
| Example No. | R¹ |
|---|---|
| I-109 | 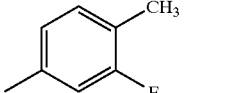 |
| I-110 | 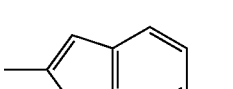 |
| I-111 | 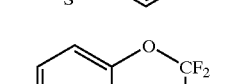 |
| I-112 | 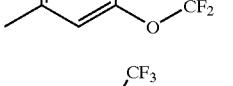 |
| I-113 | 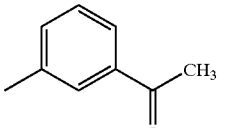 |
| I-114 | H |
| I-115 | 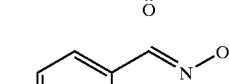 |
| I-116 | 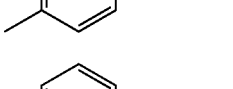 |
| I-117 | 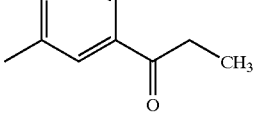 |
| I-118 | 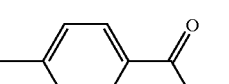 |
| I-119 | 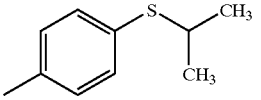 |
| I-120 | 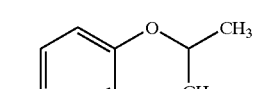 |
| I-121 |  |
| I-122 | 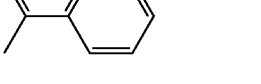 |
| I-123 | 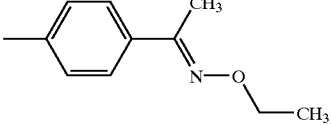 |
| I-124 | 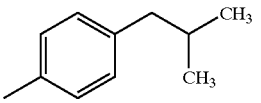 |
| I-125 | 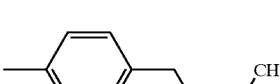 |
| I-126 |  |
| I-127 | 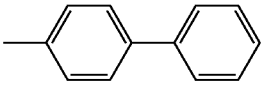 |
| I-128 | 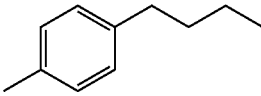 |
| I-129 | 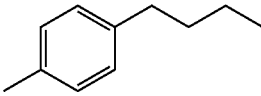 |

TABLE 3-continued (I-f-3)

[Structure: 3-methylthiophene connected to dihydropyrrole with phenyl-R¹ substituent]

| Example No. | R¹ |
|---|---|
| I-130 | –C₆H₄–O–CH₂–C₆H₄–Cl (4-((4-chlorobenzyl)oxy)phenyl) |
| I-131 | –C₆H₄–CH₃ |
| I-132 | –C₆H₄–OCH₃ |
| I-133 | –C₆H₄–C(=O)–CH₃ |
| I-134 | —(CH₂)₃—CH₃ |
| I-135 | –C₆H₄–Br |
| I-136 | –C₆H₄–SCF₃ |
| I-137 | –C₆H₄–S(=O)–CF₃ |
| I-138 | –C₆H₄–S(=O)₂–CF₃ |
| I-139 | –C₆H₄–SCHF₂ |
| I-140 | –C₆H₄–S(=O)–CHF₂ |
| I-141 | –C₆H₄–S(=O)₂–CHF₂ |

Preference is furthermore given to the compounds of the formula (I-f4) listed in Table 4

TABLE 4

(I-f-4)

[Structure: 5-chlorothiophene connected to dihydropyrrole with phenyl-R¹ substituent]

| Example No. | R¹ |
|---|---|
| I-142 | –C₆H₄–CH(CH₃)₂ |
| I-143 | 3,5-dichlorophenyl |
| I-144 | –C₆H₄–F |
| I-145 | –C₆H₄–Cl |
| I-146 | 3-methylthiophen-... |
| I-147 | 5-methylthiophene-2-CH=N–O–CH₃ |
| I-148 | –C₆H₄–OCF₃ |
| I-149 | —Br |
| I-150 | 2,2-difluoro-benzo[1,3]dioxol-5-yl |
| I-151 | 4-OCF₃-3-F-phenyl |
| I-152 | 3-CF₃-phenyl |
| I-153 | –C₆H₄–CF₃ |

TABLE 4-continued (I-f-4)

| Example No. | R¹ |
|---|---|
| I-154 | 2-CHO-phenyl (OHC, CH₃ ortho) — 2-methylbenzaldehyde group |
| I-155 | 4-CHO-phenyl |
| I-156 | 4-COOH-phenyl |
| I-157 | 2-fluoro-4-methylphenyl with CH₃ |
| I-158 | benzothiophen-2-yl |
| I-159 | 2,2-difluoro-1,3-benzodioxol-5-yl (O-CF₂-CF₂-O) |
| I-160 | 3,5-bis(trifluoromethyl)phenyl |
| I-161 | H |
| I-162 | 3-acetylphenyl |
| I-163 | 4-(CH=N-OCH₃)phenyl |
| I-164 | 3-propanoylphenyl |
| I-165 | 4-propanoylphenyl |
| I-166 | 4-(CH=N-OC₂H₅)phenyl |
| I-167 | 4-(S-iPr)phenyl |
| I-168 | 4-(O-iPr)phenyl |
| I-169 | naphthalen-1-yl |
| I-170 | 4-(C(CH₃)=N-OC₂H₅)phenyl |
| I-171 | 4-(C(C₂H₅)=N-OCH₃)phenyl |
| I-172 | 4-isobutylphenyl |
| I-173 | 4-(CH₂-S-iPr)phenyl |
| I-174 | biphenyl-4-yl |
| I-175 | 4-pentylphenyl |

TABLE 4-continued
(I-f-4)
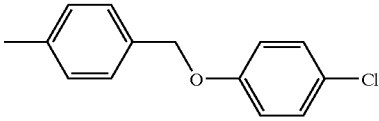
| Example No. | R¹ |
|---|---|
| I-176 | 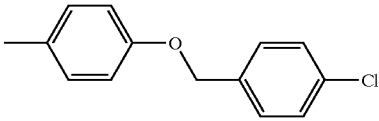 |
| I-177 | 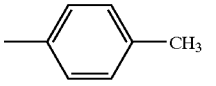 |
| I-178 | 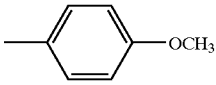 |
| I-179 | 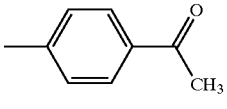 |
| I-180 | 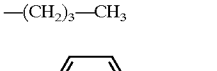 |
| I-181 | —(CH₂)₃—CH₃ |
| I-182 | 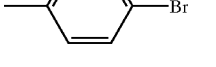 |
| I-183 | 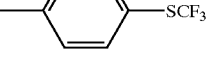 |
| I-184 | 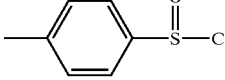 |
| I-185 | 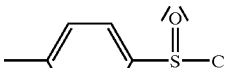 |
| I-186 | 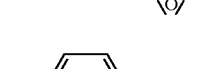 |
| I-187 | 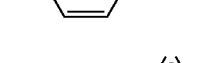 |
| I-188 | 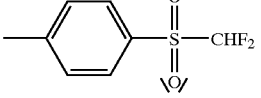 |
Preference is furthermore given to the compounds of the formula (I-f-5) listed in Table 5
TABLE 5
(I-f-5)
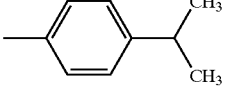
| Example No. | R¹ |
|---|---|
| I-189 | 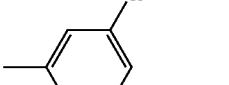 |
| I-190 | 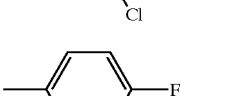 |
| I-191 | 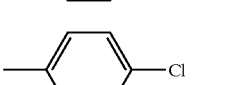 |
| I-192 | 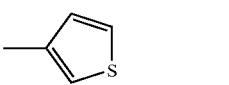 |
| I-193 | 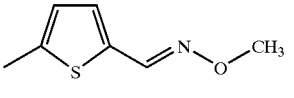 |
| I-194 | 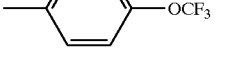 |
| I-195 |  |

TABLE 5-continued (I-f-5)

[Structure: 3-chlorothiophene connected to dihydropyrrole ring bearing phenyl-R¹ group]

| Example No. | R¹ |
|---|---|
| I-196 | —Br |
| I-197 | 2,2-difluoro-1,3-benzodioxol-5-yl |
| I-198 | 4-(OCF₃), 3-F phenyl |
| I-199 | 3-(CF₃)phenyl |
| I-200 | 4-(CF₃)phenyl |
| I-201 | 2-(CHO)phenyl |
| I-202 | 4-(CHO)phenyl |
| I-203 | 4-(COOH)phenyl |
| I-204 | 4-CH₃, 3-F phenyl |
| I-205 | benzothiophen-2-yl |
| I-206 | 2,2-bis(CF₂)-1,3-benzodioxin-6-yl |
| I-207 | 3,5-bis(CF₃)phenyl |
| I-208 | H |
| I-209 | 3-acetylphenyl |
| I-210 | 4-(CH=N-OCH₃)phenyl |
| I-211 | 3-propanoylphenyl |
| I-212 | 4-propanoylphenyl |
| I-213 | 4-(CH=N-OC₂H₅)phenyl |
| I-214 | 4-(S-iPr)phenyl |
| I-215 | 4-(O-iPr)phenyl |
| I-216 | naphthalen-1-yl |
| I-217 | 4-(C(CH₃)=N-OC₂H₅)phenyl |

TABLE 5-continued
(I-f-5)
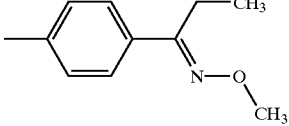
| Example No. | R¹ |
|---|---|
| I-218 | 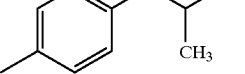 |
| I-219 | 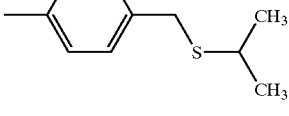 |
| I-220 | 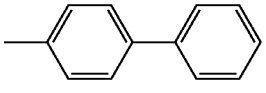 |
| I-221 |  |
| I-222 | 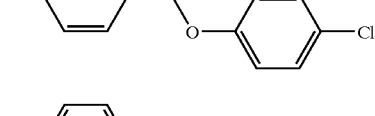 |
| I-223 | 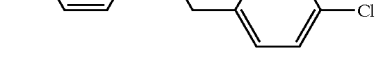 |
| I-224 | 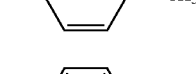 |
| I-225 | 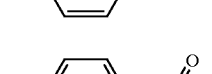 |
| I-226 | 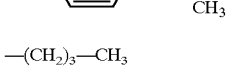 |
| I-227 | 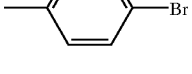 |
| I-228 | —(CH₂)₃—CH₃ |
| I-229 |  |
TABLE 5-continued
(I-f-5)
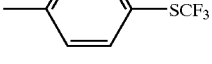
| Example No. | R¹ |
|---|---|
| I-230 | 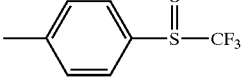 |
| I-231 | 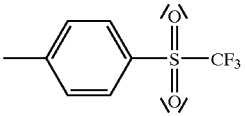 |
| I-232 | 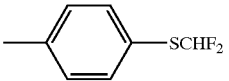 |
| I-233 | 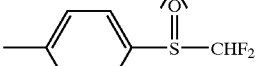 |
| I-234 | 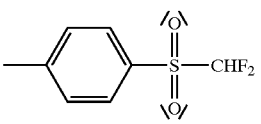 |
| I-235 | 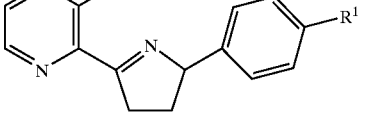 |
Preference is furthermore given to the compounds of the formula 1 (I-f-6) listed in Table 6
TABLE 6
(I-f-6)
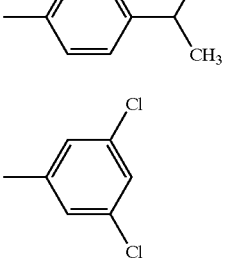
| Example No. | R¹ |
|---|---|
| I-236 | (4-isopropylphenyl) |
| I-237 | (3,5-dichlorophenyl) |

TABLE 6-continued
(I-f-6)
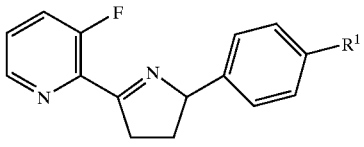
| Example No. | R¹ |
|---|---|
| I-238 | 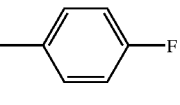 |
| I-239 | 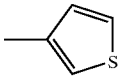 |
| I-240 | 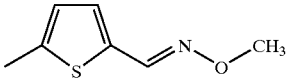 |
| I-241 | 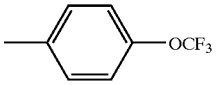 |
| I-242 | 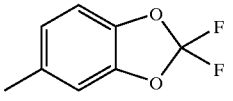 |
| I-243 | —Br |
| I-244 | 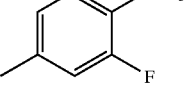 |
| I-245 | 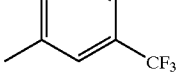 |
| I-246 | 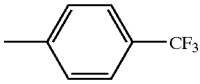 |
| I-247 | 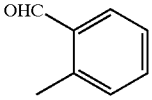 |
| I-248 | 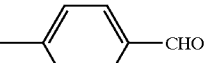 |
| I-249 | 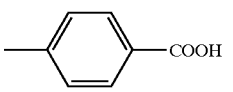 |
| I-250 | 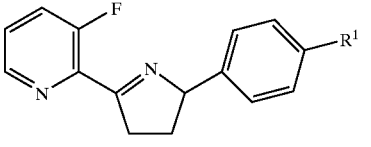 |
| I-251 | 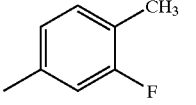 |
| I-252 | 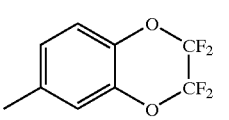 |
| I-253 | 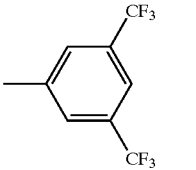 |
| I-254 | 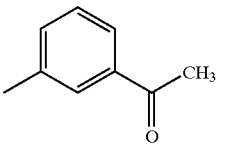 |
| I-255 | H |
| I-256 | 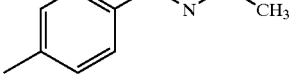 |
| I-257 | 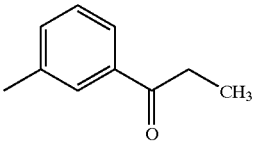 |
| I-258 | 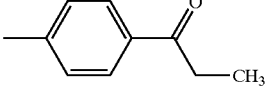 |
| I-259 | 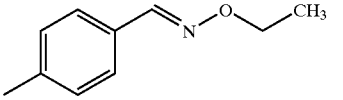 |
| I-260 | 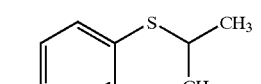 |
| I-261 |  |

TABLE 6-continued
(I-f-6)
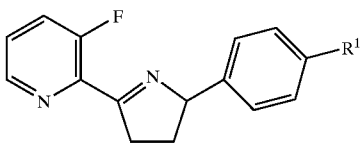
| Example No. | R¹ |
|---|---|
| I-262 | 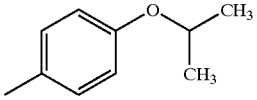 |
| I-263 | 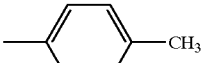 |
| I-264 | 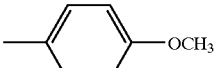 |
| I-265 | 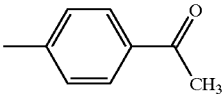 |
| I-266 | 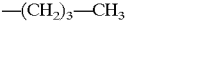 |
| I-267 | 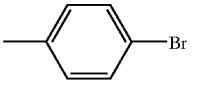 |
| I-268 | 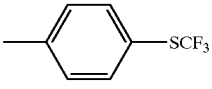 |
| I-269 | 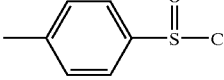 |
| I-270 | 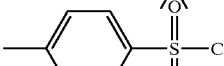 |
| I-271 | 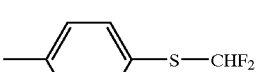 |
TABLE 6-continued
(I-f-6)
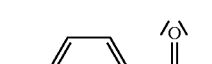
| Example No. | R¹ |
|---|---|
| I-272 | 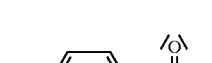 |
| I-273 | 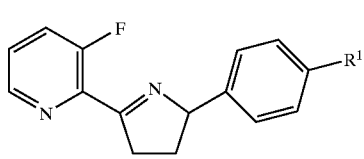 |
| I-274 | 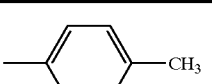 |
| I-275 | —(CH$_2$)$_3$—CH$_3$ |
| I-276 | 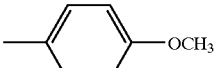 |
| I-277 | 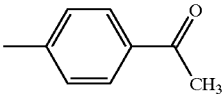 |
| I-278 | 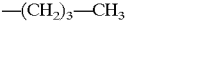 |
| I-279 | 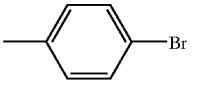 |
| I-280 | 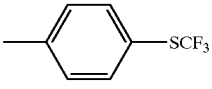 |
| I-281 | 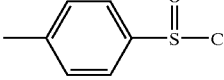 |
| I-282 | 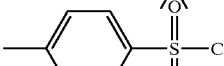 |

Preference is furthermore given to the compounds of the formula (I-f-7) listed in Table 7
TABLE 7
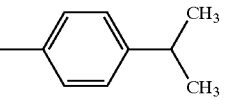
(I-f-7)
| Example No. | R¹ |
|---|---|
| I-283 | 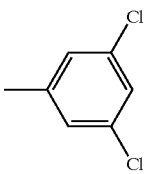 |
| I-284 | 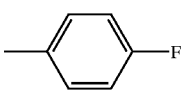 |
| I-285 | 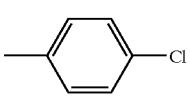 |
| I-286 | 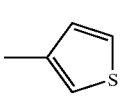 |
| I-287 | 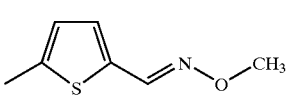 |
| I-288 | 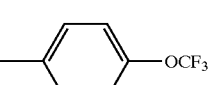 |
| I-289 | 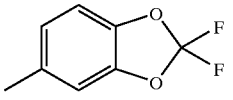 |
| I-290 | —Br |
| I-291 | 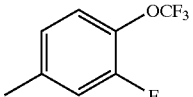 |
| I-292 | 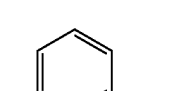 |
| I-293 |  |
| I-294 | 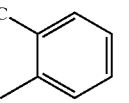 |
TABLE 7-continued
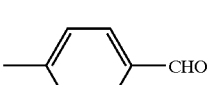
(I-f-7)
| Example No. | R¹ |
|---|---|
| I-295 | 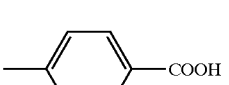 |
| I-296 | 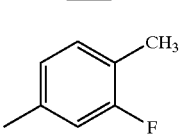 |
| I-297 | 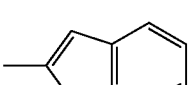 |
| I-298 | 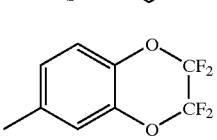 |
| I-299 | 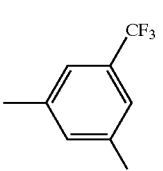 |
| I-300 | 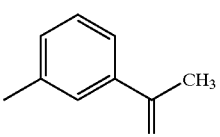 |
| I-301 | 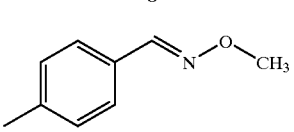 |
| I-302 | H |
| I-303 | 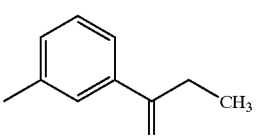 |
| I-304 |  |
| I-305 |  |

TABLE 7-continued
(I-f-7)
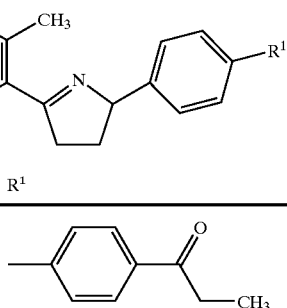
| Example No. | R¹ |
|---|---|
| I-306 | 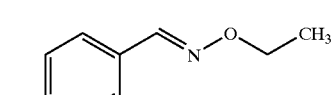 |
| I-307 | 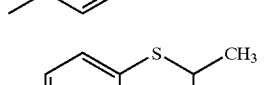 |
| I-308 | 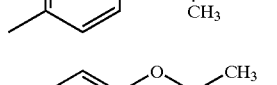 |
| I-309 | 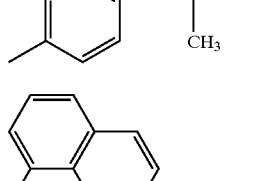 |
| I-310 | 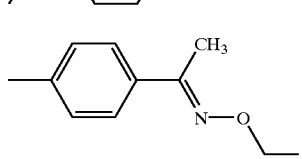 |
| I-311 | 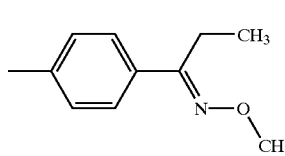 |
| I-312 | 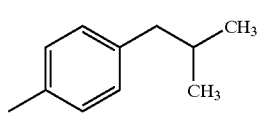 |
| I-313 | 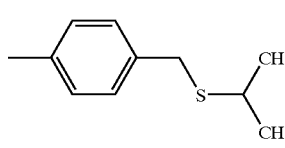 |
| I-314 | 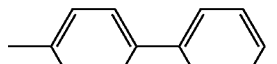 |
| I-315 | 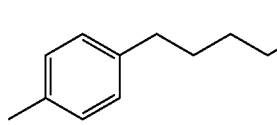 |
| I-316 | 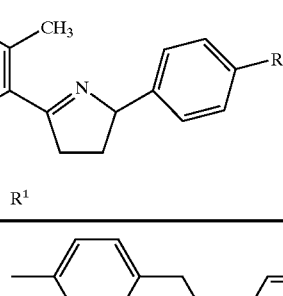 |
TABLE 7-continued
(I-f-7)
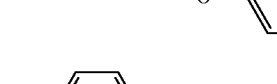
| Example No. | R¹ |
|---|---|
| I-317 | 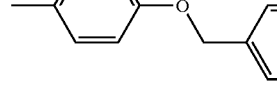 |
| I-318 | 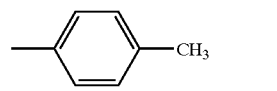 |
| I-319 | 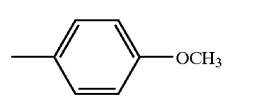 |
| I-320 | 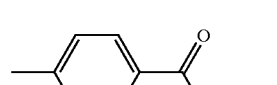 |
| I-321 | 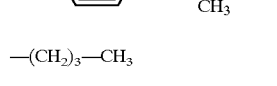 |
| I-322 | —(CH$_2$)$_3$—CH$_3$ |
| I-323 | 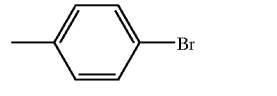 |
| I-324 | 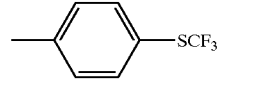 |
| I-325 | 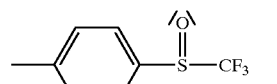 |
| I-326 | 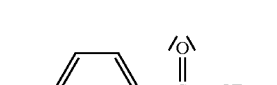 |
| I-327 | 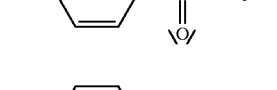 |
| I-328 |  |

TABLE 7-continued

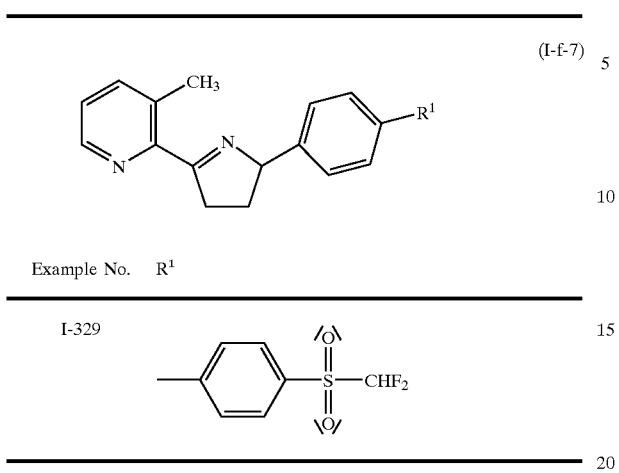

(I-f-7)

| Example No. | R¹ |
|---|---|
| I-329 | <image with SO2-CHF2 group on phenyl> |

Preference is furthermore given to the compounds of the formula (I-f-8) listed in Table 8

TABLE 8

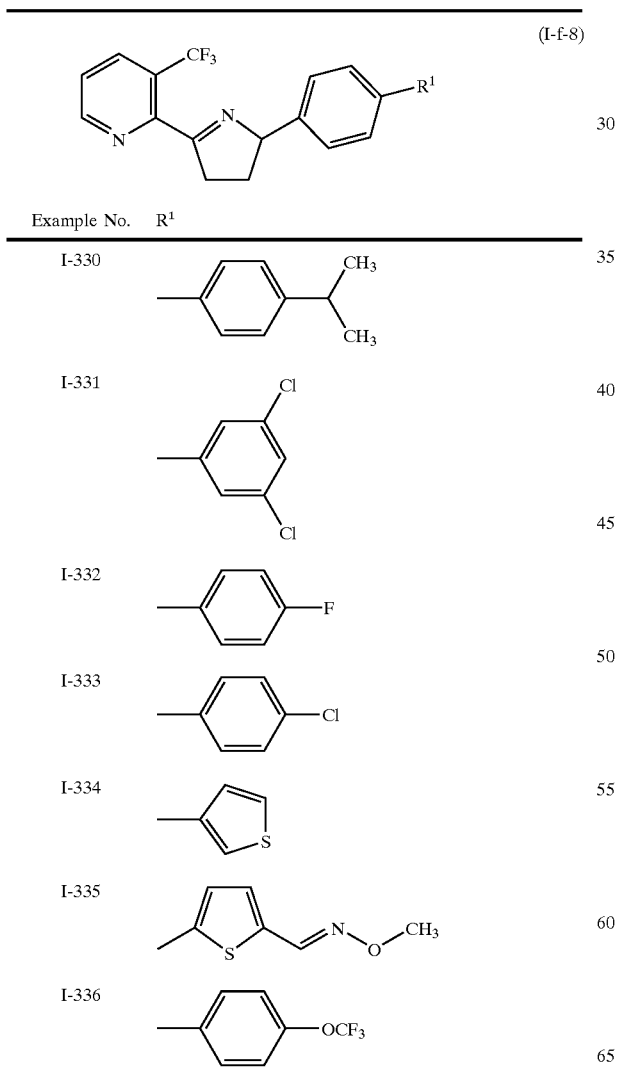

(I-f-8)

| Example No. | R¹ |
|---|---|
| I-330 | 4-isopropylphenyl |
| I-331 | 3,5-dichlorophenyl |
| I-332 | 4-fluorophenyl |
| I-333 | 4-chlorophenyl |
| I-334 | 3-thienyl |
| I-335 | 5-(methoxyiminomethyl)-2-thienyl |
| I-336 | 4-(OCF3)phenyl |

TABLE 8-continued

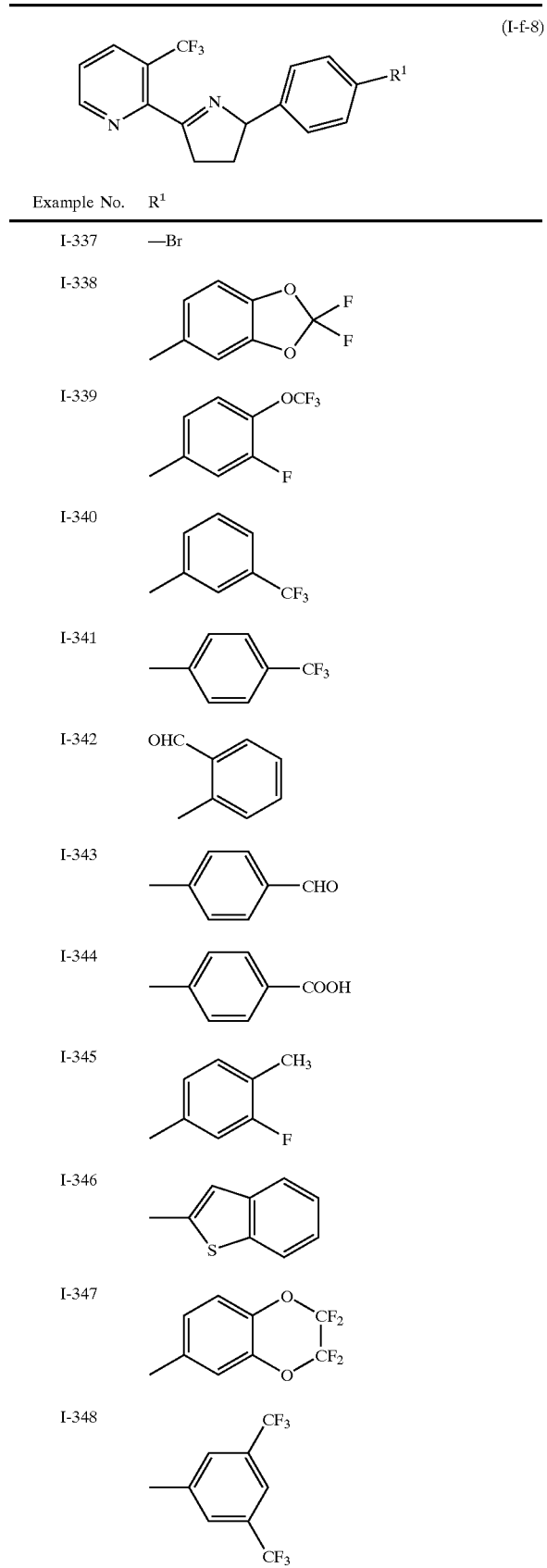

(I-f-8)

| Example No. | R¹ |
|---|---|
| I-337 | —Br |
| I-338 | 2,2-difluoro-1,3-benzodioxol-5-yl |
| I-339 | 2-fluoro-4-(OCF3)phenyl (substituted) |
| I-340 | 3-(CF3)phenyl |
| I-341 | 4-(CF3)phenyl |
| I-342 | 2-(CHO)phenyl |
| I-343 | 4-CHO-phenyl |
| I-344 | 4-COOH-phenyl |
| I-345 | 3-fluoro-4-methylphenyl |
| I-346 | 2-benzothienyl |
| I-347 | 2,2,3,3-tetrafluoro-1,4-benzodioxin-6-yl |
| I-348 | 3,5-bis(CF3)phenyl |

TABLE 8-continued
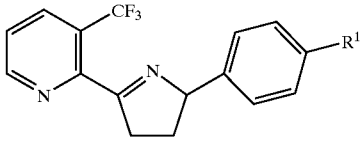
(I-f-8)
| Example No. | R¹ |
|---|---|
| I-349 | H |
| I-350 | 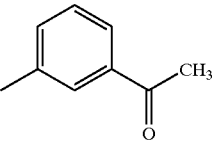 |
| I-351 | 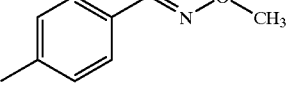 |
| I-352 | 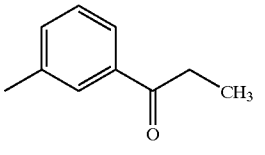 |
| I-353 | 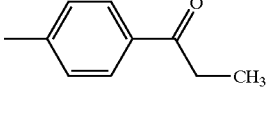 |
| I-354 | 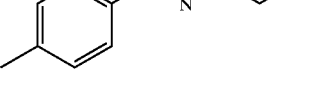 |
| I-355 | 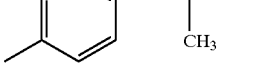 |
| I-356 | 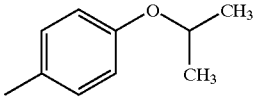 |
| I-357 | 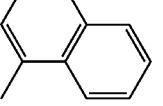 |
| I-358 | 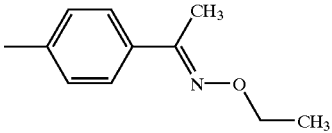 |
| I-359 | 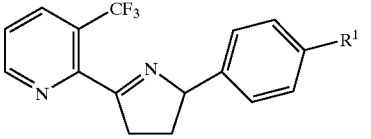 |
| I-360 | 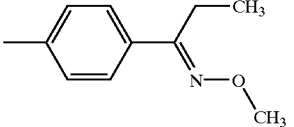 |
| I-361 | 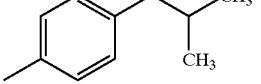 |
| I-362 | 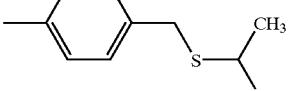 |
| I-363 | 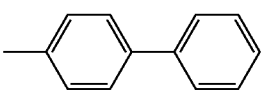 |
| I-364 | 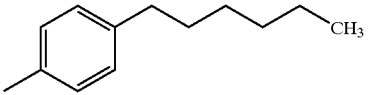 |
| I-365 | 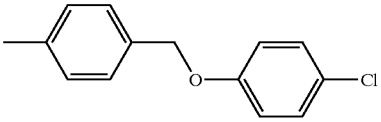 |
| I-366 | 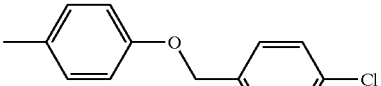 |
| I-367 | 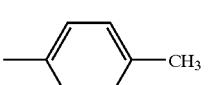 |
| I-368 | 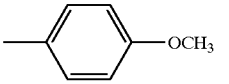 |
| I-369 | —(CH$_2$)$_3$—CH$_3$ |
| I-370 | 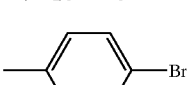 |

TABLE 8-continued
(I-f-8)
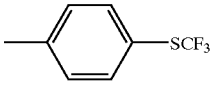
| Example No. | R¹ |
|---|---|
| I-371 | 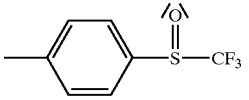 |
| I-372 | 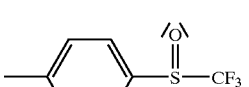 |
| I-373 | 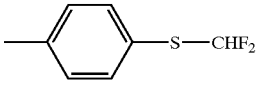 |
| I-374 | 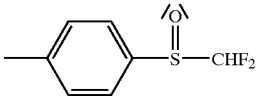 |
| I-375 | 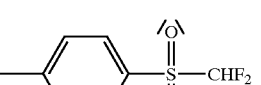 |
| I-376 |  |
Preference is furthermore given to the compounds of the formula (I-f-9) listed in Table 9
TABLE 9
(I-f-9)
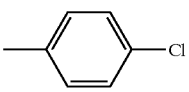
| Example No. | R¹ |
|---|---|
| I-377 | 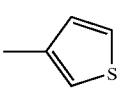 |
| I-378 | 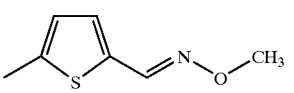 |
TABLE 9-continued
(I-f-9)
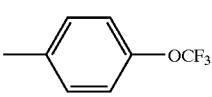
| Example No. | R¹ |
|---|---|
| I-379 |  |
| I-380 | 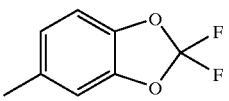 |
| I-381 | 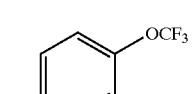 |
| I-382 | 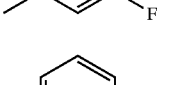 |
| I-383 | 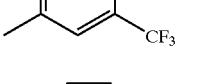 |
| I-384 | —Br |
| I-385 | 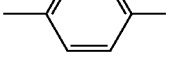 |
| I-386 | 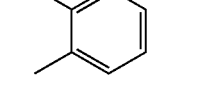 |
| I-387 | 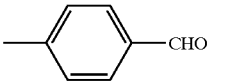 |
| I-388 | 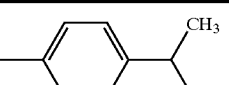 |
| I-389 | 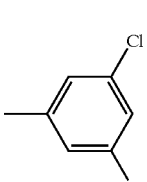 |
| I-390 |  |
| I-391 |  |

TABLE 9-continued
(I-f-9)
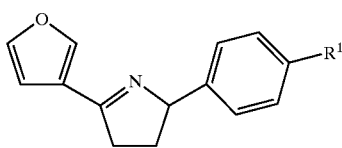
| Example No. | R¹ |
|---|---|
| I-392 | 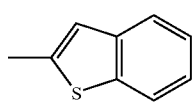 |
| I-393 | 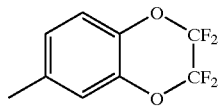 |
| I-394 | 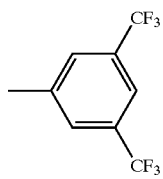 |
| I-395 | 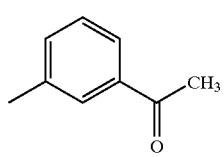 |
| I-396 | H |
| I-397 | 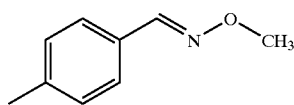 |
| I-398 | 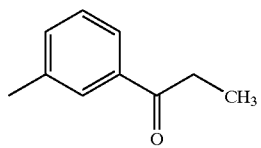 |
| I-399 | 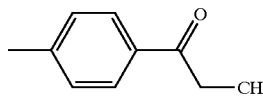 |
| I-400 | 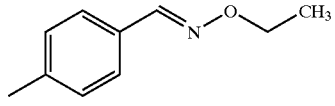 |
| I-401 | 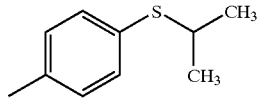 |
| I-402 | 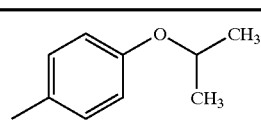 |
TABLE 9-continued
(I-f-9)
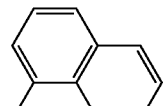
| Example No. | R¹ |
|---|---|
| I-403 | 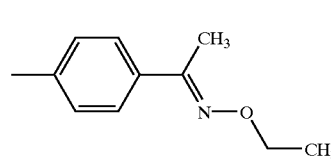 |
| I-404 | 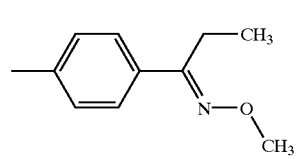 |
| I-405 | 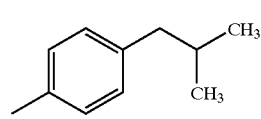 |
| I-406 | 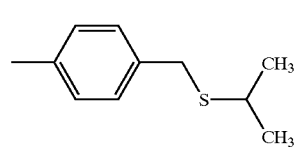 |
| I-407 | 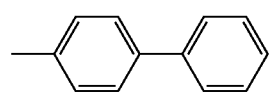 |
| I-408 | 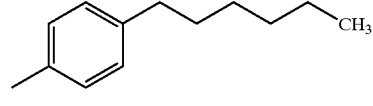 |
| I-409 | 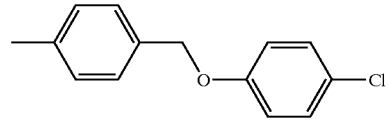 |
| I-410 | 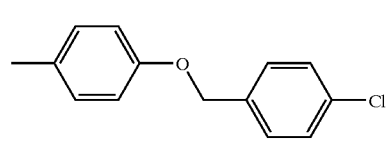 |
| I-411 | |
| I-412 | |

TABLE 9-continued (I-f-9)

| Example No. | R¹ |
|---|---|
| I-413 | —C₆H₄—CH₃ (para) |
| I-414 | —C₆H₄—OCH₃ (para) |
| I-415 | —C₆H₄—C(=O)CH₃ (para) |
| I-416 | —(CH₂)₃—CH₃ |
| I-417 | —C₆H₄—Br (para) |
| I-418 | —C₆H₄—SCF₃ (para) |
| I-419 | —C₆H₄—S(=O)—CF₃ (para) |
| I-420 | —C₆H₄—S(=O)₂—CF₃ (para) |
| I-421 | —C₆H₄—S—CHF₂ (para) |
| I-422 | —C₆H₄—S(=O)—CHF₂ (para) |
| I-423 | —C₆H₄—S(=O)₂—CHF₂ (para) |

Preference is furthermore given to the compounds of the formula (I-f-10) listed in Table 10

TABLE 10

(I-f-10)

| Example No. | R¹ |
|---|---|
| I-424 | —C₆H₄—CH(CH₃)₂ (para) |
| I-425 | —C₆H₃—(3,5-Cl₂) |
| I-426 | —C₆H₄—F (para) |
| I-427 | —C₆H₄—Cl (para) |
| I-428 | 3-methylthiophen-yl |
| I-429 | 5-methyl-thiophen-2-yl-CH=N—O—CH₃ |
| I-430 | —C₆H₄—OCF₃ (para) |
| I-431 | —Br |
| I-432 | 5-methyl-2,2-difluoro-benzo[1,3]dioxole |
| I-433 | —C₆H₃—(OCF₃, F) |
| I-434 | —C₆H₄—CF₃ (meta) |
| I-435 | —C₆H₄—CF₃ (para) |

TABLE 10-continued
(I-f-10)
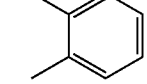
| Example No. | R¹ |
|---|---|
| I-436 | 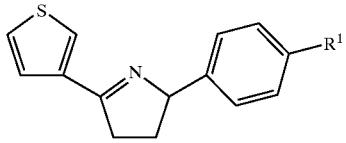 |
| I-437 | 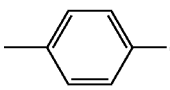 |
| I-438 | 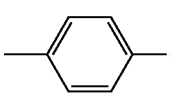 |
| I-439 | 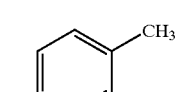 |
| I-440 |  |
| I-441 | 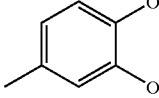 |
| I-442 | 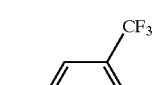 |
| I-443 | H |
| I-444 | 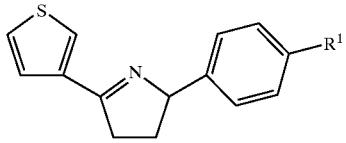 |
| I-445 | 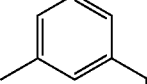 |
| I-446 | 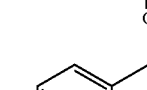 |
TABLE 10-continued
(I-f-10)
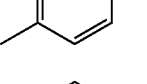
| Example No. | R¹ |
|---|---|
| I-447 | 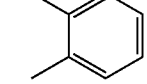 |
| I-448 | 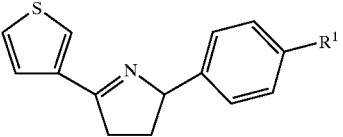 |
| I-449 | 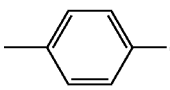 |
| I-450 | 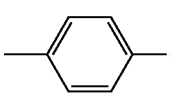 |
| I-451 | 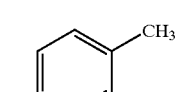 |
| I-452 |  |
| I-453 | 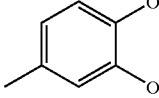 |
| I-454 | 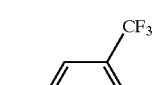 |
| I-455 | 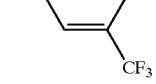 |
| I-456 | 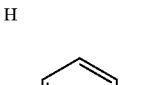 |
| I-457 | 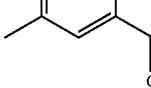 |

TABLE 10-continued
(I-f-10)
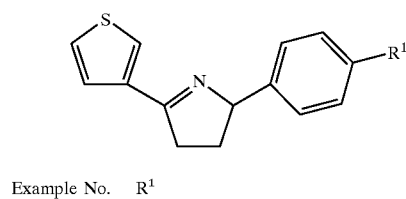
| Example No. | R¹ |
|---|---|
| I-458 | 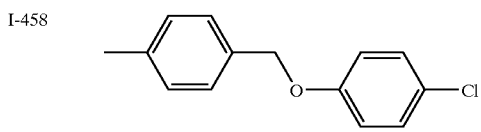 |
| I-459 | 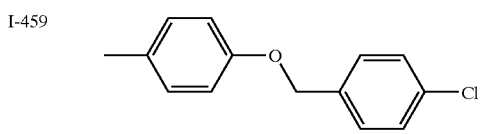 |
| I-460 | 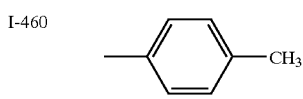 |
| I-461 | 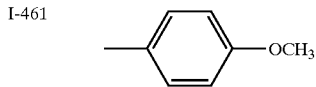 |
| I-462 | 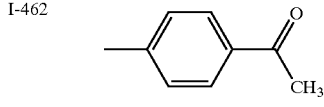 |
| I-463 | —(CH$_2$)$_3$—CH$_3$ |
| I-464 | 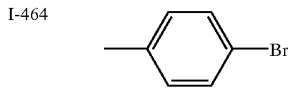 |
| I-465 | 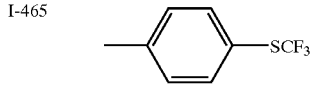 |
| I-466 | 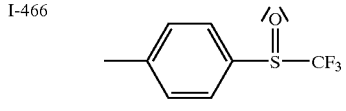 |
| I-467 | 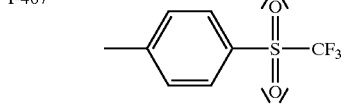 |
| I-468 | 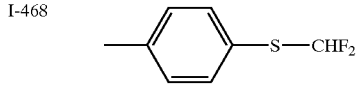 |
| I-469 | 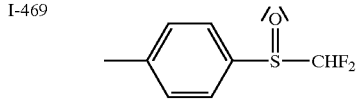 |
TABLE 10-continued
(I-f-10)
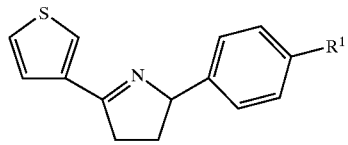
| Example No. | R¹ |
|---|---|
| I-470 | 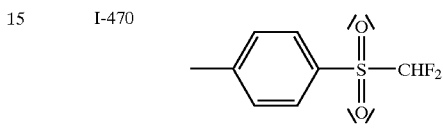 |
Preference is furthermore given to the compounds of the formula (I-f-11) listed in Table 11
TABLE 11
(I-f-11)
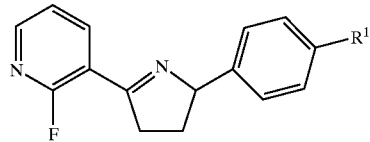
| Example No. | R¹ |
|---|---|
| I-471 | 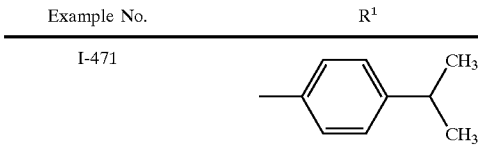 |
| I-472 | 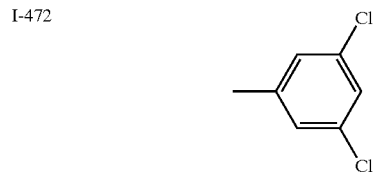 |
| I-473 | 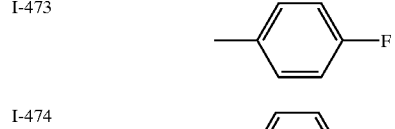 |
| I-474 |  |
| I-475 | 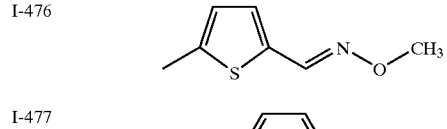 |
| I-476 |  |
| I-477 | 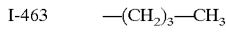 |

TABLE 11-continued
(I-f-11)
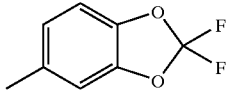
| Example No. | R¹ |
|---|---|
| I-478 | —Br |
| I-479 | 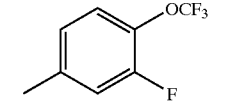 |
| I-480 | 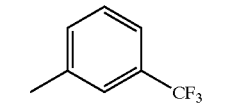 |
| I-481 | 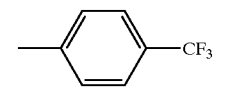 |
| I-482 | 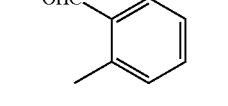 |
| I-483 | 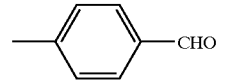 |
| I-484 | 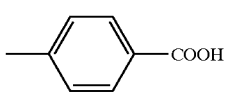 |
| I-485 | 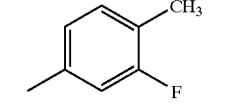 |
| I-486 | 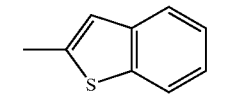 |
| I-487 | 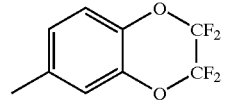 |
| I-488 | 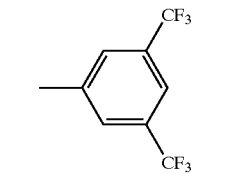 |
| I-489 | 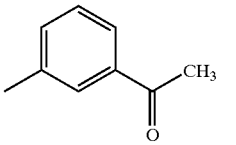 |
TABLE 11-continued
(I-f-11)
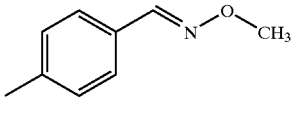
| Example No. | R¹ |
|---|---|
| I-490 | H |
| I-491 | 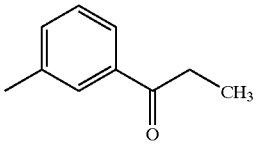 |
| I-492 | 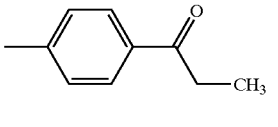 |
| I-493 | 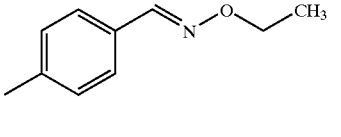 |
| I-494 | 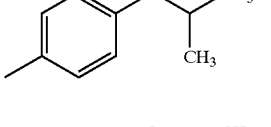 |
| I-495 | 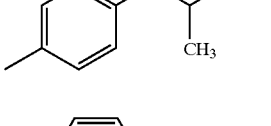 |
| I-496 | 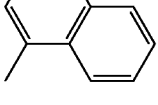 |
| I-497 | 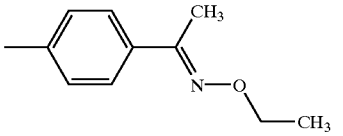 |
| I-498 | |
| I-499 | |

TABLE 11-continued
(I-f-11)
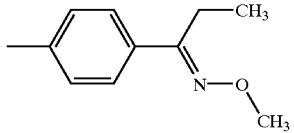
| Example No. | R¹ |
|---|---|
| I-500 | 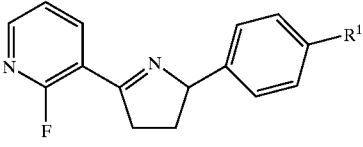 |
| I-501 | 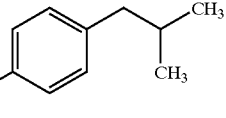 |
| I-502 | 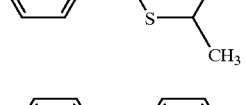 |
| I-503 | 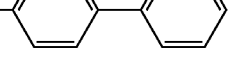 |
| I-504 |  |
| I-505 | 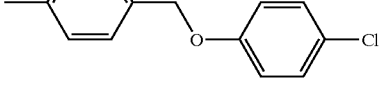 |
| I-506 | 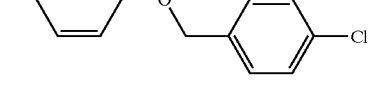 |
| I-507 | 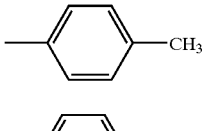 |
| I-508 | 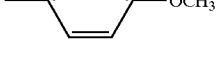 |
| I-509 | 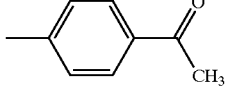 |
| I-510 | —(CH$_2$)$_3$—CH$_3$ |
| I-511 |  |
TABLE 11-continued
(I-f-11)
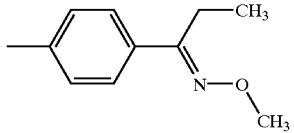
| Example No. | R¹ |
|---|---|
| I-512 | 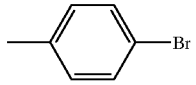 |
| I-513 | 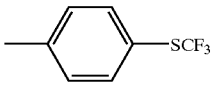 |
| I-514 | 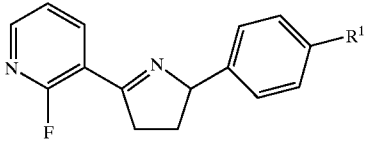 |
| I-515 | 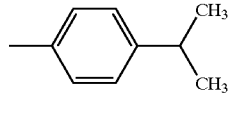 |
| I-516 | 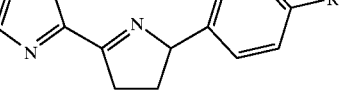 |
| I-517 | 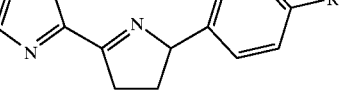 |
Preference is furthermore given to the compounds of the formula (I-f-12) listed in Table 12
TABLE 12
(I-f-12)
| Example No. | R¹ |
|---|---|
| I-518 | |
| I-519 | |

TABLE 12-continued
(I-f-12)
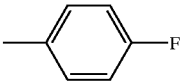
| Example No. | R¹ |
|---|---|
| I-520 | 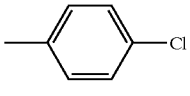 |
| I-521 | 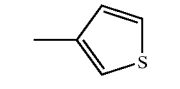 |
| I-522 | 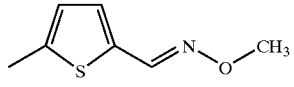 |
| I-523 | 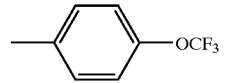 |
| I-524 | 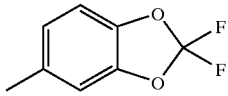 |
| I-525 | —Br |
| I-526 | 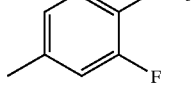 |
| I-527 | 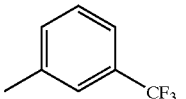 |
| I-528 | 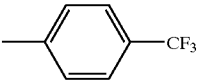 |
| I-529 | 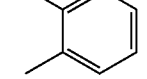 |
| I-530 | 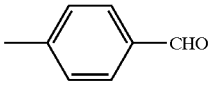 |
| I-531 | 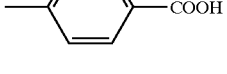 |
| I-532 | 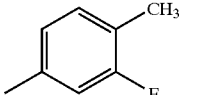 |
| I-533 | 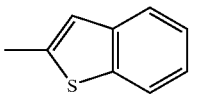 |
| I-534 | 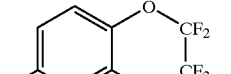 |
| I-535 | 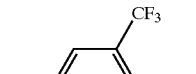 |
| I-536 | 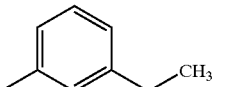 |
| I-537 | H |
| I-538 | 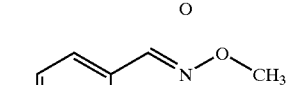 |
| I-539 | 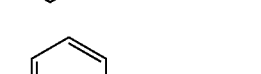 |
| I-540 |  |
| I-541 |  |
| I-542 |  |
| I-543 |  |

TABLE 12-continued
(I-f-12)
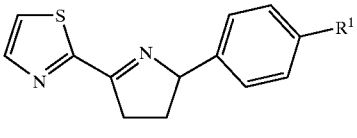
| Example No. | R¹ |
|---|---|
| I-544 | 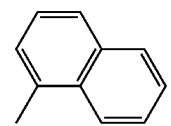 |
| I-545 | 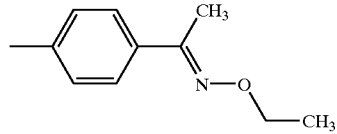 |
| I-546 | 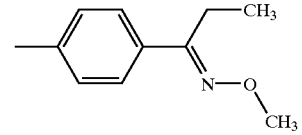 |
| I-547 | 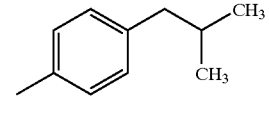 |
| I-548 | 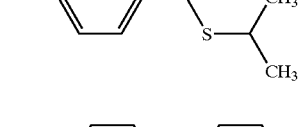 |
| I-549 | 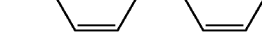 |
| I-550 | 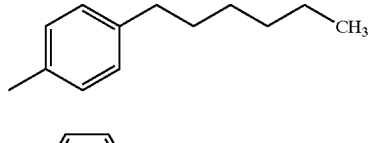 |
| I-551 | 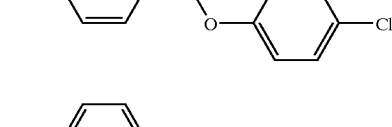 |
| I-552 | 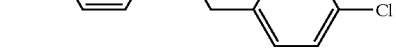 |
| I-553 |  |
TABLE 12-continued
(I-f-12)
| Example No. | R¹ |
|---|---|
| I-554 | 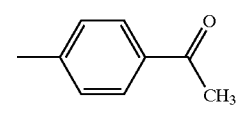 |
| I-555 |  |
| I-556 | 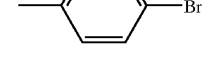 |
| I-557 | —$(CH_2)_3$—$CH_3$ |
| I-558 | 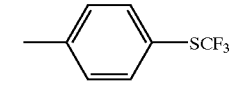 |
| I-559 | 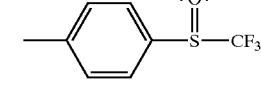 |
| I-560 | 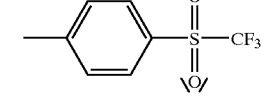 |
| I-561 | 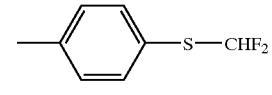 |
| I-562 | 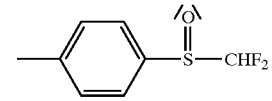 |
| I-563 | 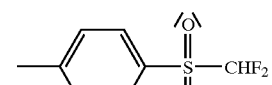 |
| I-564 |  |

Preference is furthermore given to the compounds of the formula (I-f-13) listed in Table 13
TABLE 13
(I-f-13)
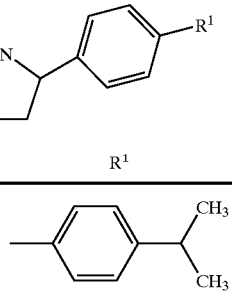
| Example No. | R¹ |
|---|---|
| I-565 | 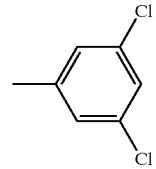 |
| I-566 |  |
| I-567 | 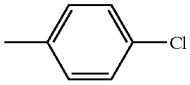 |
| I-568 | 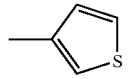 |
| I-569 | 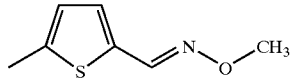 |
| I-570 | 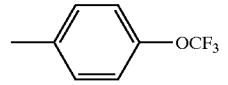 |
| I-571 | 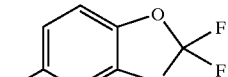 |
| I-572 | —Br |
| I-573 | 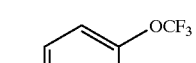 |
| I-574 | 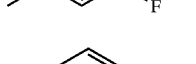 |
| I-575 | 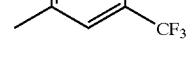 |
| I-576 | 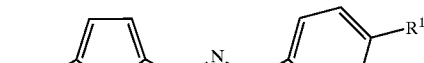 |
TABLE 13-continued
(I-f-13)
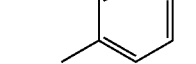
| Example No. | R¹ |
|---|---|
| I-577 | 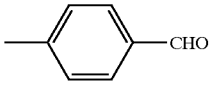 |
| I-578 | 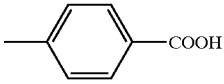 |
| I-579 | 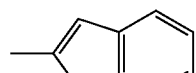 |
| I-580 | 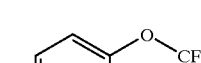 |
| I-581 | 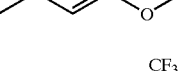 |
| I-582 | 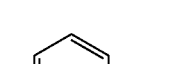 |
| I-583 | 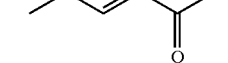 |
| I-584 | H |
| I-585 | 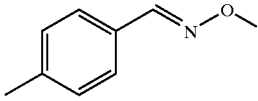 |
| I-586 |  |
| I-587 |  |

TABLE 13-continued (I-f-13)

[Structure: 5-methylfuran-2-yl connected to a dihydropyrrole ring with N=C, and a phenyl-R¹ group]

| Example No. | R¹ |
|---|---|
| I-588 | 4-methylphenyl-C(=O)-CH₂-CH₃ |
| I-589 | 4-methylphenyl-CH=N-O-CH₂-CH₃ |
| I-590 | 4-methylphenyl-S-CH(CH₃)₂ |
| I-591 | 4-methylphenyl-O-CH(CH₃)₂ |
| I-592 | 1-methylnaphthalen-yl |
| I-593 | 4-methylphenyl-C(CH₃)=N-O-CH₂-CH₃ |
| I-594 | 4-methylphenyl-C(CH₂CH₃)=N-O-CH₃ |
| I-595 | 4-methylphenyl-CH₂-CH(CH₃)-CH₃ |
| I-596 | 4-methylphenyl-CH₂-S-CH(CH₃)₂ |
| I-597 | 4-methylbiphenyl |
| I-598 | 4-methylphenyl-(CH₂)₄-CH₃ |
| I-599 | 4-methylphenyl-CH₂-O-(4-chlorophenyl) |
| I-600 | 4-methylphenyl-O-CH₂-(4-chlorophenyl) |
| I-601 | 4-methylphenyl-CH₃ |
| I-602 | 4-methylphenyl-OCH₃ |
| I-603 | 4-methylphenyl-C(=O)-CH₃ |
| I-604 | —(CH₂)₃—CH₃ |
| I-605 | 4-methylphenyl-Br |
| I-606 | 4-methylphenyl-SCF₃ |
| I-607 | 4-methylphenyl-S(=O)-CF₃ |
| I-608 | 4-methylphenyl-S(=O)₂-CF₃ |
| I-609 | 4-methylphenyl-S-CHF₂ |
| I-610 | 4-methylphenyl-S(=O)-CHF₂ |

TABLE 13-continued (I-f-13)

| Example No. | R¹ |
|---|---|
| I-611 | [4-methylphenyl-SO₂-CHF₂] |

Preference is furthermore given to the compounds of the formula (I-f-14) listed in Table 14

TABLE 14

(I-f-14)

| Example No. | R¹ |
|---|---|
| I-612 | 4-isopropylphenyl |
| I-613 | 3,5-dichlorophenyl |
| I-614 | 4-fluorophenyl |
| I-615 | 4-chlorophenyl |
| I-616 | thiophen-3-yl |
| I-617 | 5-methylthiophen-2-yl-CH=N-O-CH₃ |
| I-618 | 4-OCF₃-phenyl |
| I-619 | —Br |
| I-620 | 2,2-difluoro-benzo[1,3]dioxol-5-yl (methyl-substituted) |
| I-621 | 2-fluoro-4-methyl-phenyl-OCF₃ |
| I-622 | 3-CF₃-phenyl |
| I-623 | 4-CF₃-phenyl |
| I-624 | 2-CHO-phenyl (methyl) |
| I-625 | 4-CHO-phenyl |
| I-626 | 4-COOH-phenyl |
| I-627 | 2-methyl-3-fluoro-phenyl |
| I-628 | benzo[b]thiophen-2-yl |
| I-629 | 2,2-difluoro-benzo[1,4]dioxin-CF₂ |
| I-630 | 3,5-bis(CF₃)-phenyl |

TABLE 14-continued
(I-f-14)
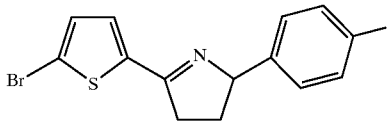
| Example No. | R¹ |
|---|---|
| I-631 | H |
| I-632 | 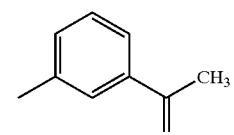 |
| I-633 | 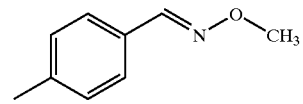 |
| I-634 | 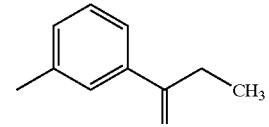 |
| I-635 | 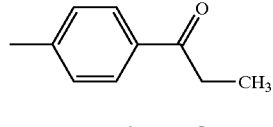 |
| I-636 |  |
| I-637 | 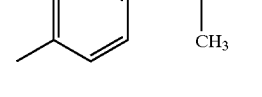 |
| I-638 | 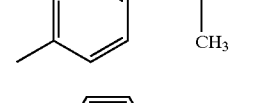 |
| I-639 | 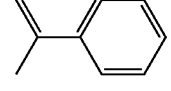 |
| I-640 | 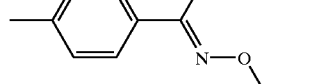 |
| I-641 | 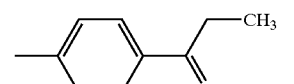 |
| I-642 | 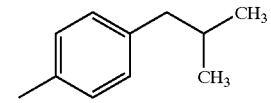 |
| I-643 | 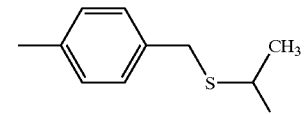 |
| I-644 | 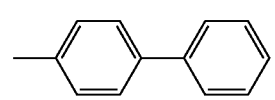 |
| I-645 | 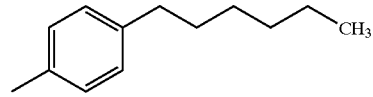 |
| I-646 | 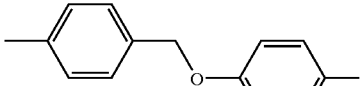 |
| I-647 | 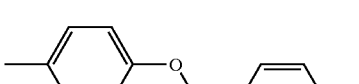 |
| I-648 |  |
| I-649 | 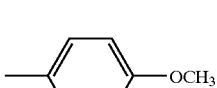 |
| I-650 | 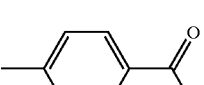 |
| I-651 | —(CH$_2$)$_3$—CH$_3$ |
| I-652 | 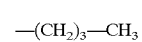 |
| I-653 | 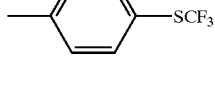 |

TABLE 14-continued (I-f-14)

| Example No. | R¹ |
|---|---|
| I-654 | —C₆H₄—S(=O)—CF₃ |
| I-655 | —C₆H₄—S(=O)(=O)—CF₃ |
| I-656 | —C₆H₄—S—CHF₂ |
| I-657 | —C₆H₄—S(=O)—CHF₂ |
| I-658 | —C₆H₄—S(=O)(=O)—CHF₂ |

Preference is furthermore given to the compounds of the formula (I-f-15) listed in Table 15

TABLE 15

(I-f-15)

| Example No. | R¹ |
|---|---|
| I-659 | —C₆H₄—CH(CH₃)₂ |
| I-660 | 3,5-dichlorophenyl |
| I-661 | —C₆H₄—F |

TABLE 15-continued (I-f-15)

| Example No. | R¹ |
|---|---|
| I-662 | —C₆H₄—Cl |
| I-663 | 3-thienyl |
| I-664 | 5-(CH=N—OCH₃)-thien-2-yl |
| I-665 | —C₆H₄—OCF₃ |
| I-666 | —Br |
| I-667 | 2,2-difluoro-benzo[1,3]dioxol-5-yl |
| I-668 | —C₆H₃(OCF₃)(F) |
| I-669 | 3-CF₃—C₆H₄— |
| I-670 | 4-CF₃—C₆H₄— |
| I-671 | 2-CHO—C₆H₄— |
| I-672 | 4-CHO—C₆H₄— |
| I-673 | 4-COOH—C₆H₄— |
| I-674 | 2-CH₃-4-F—C₆H₃— |

TABLE 15-continued
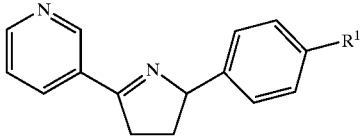
(I-f-15)
| Example No. | R$^1$ |
|---|---|
| I-675 | 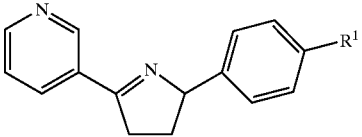 |
| I-676 | 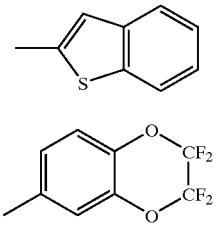 |
| I-677 | 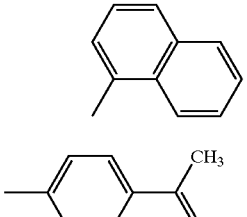 |
| I-678 | H |
| I-679 | 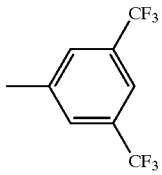 |
| I-680 | 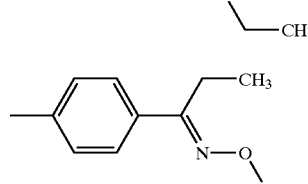 |
| I-681 | 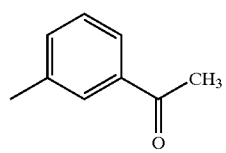 |
| I-682 | 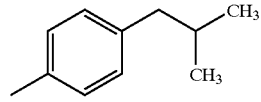 |
| I-683 | 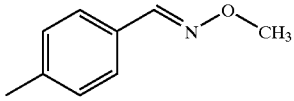 |
| I-684 | 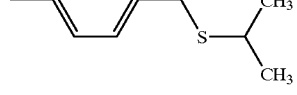 |
| I-685 | 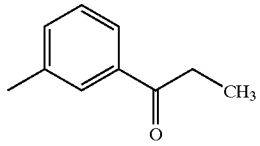 |
TABLE 15-continued
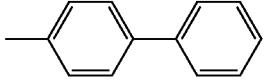
(I-f-15)
| Example No. | R$^1$ |
|---|---|
| I-686 | 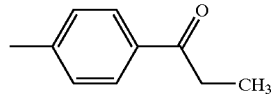 |
| I-687 |  |
| I-688 | 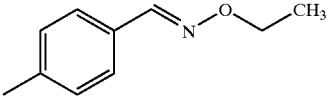 |
| I-689 | 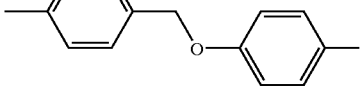 |
| I-690 | 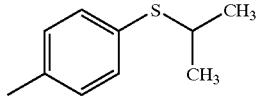 |
| I-691 | 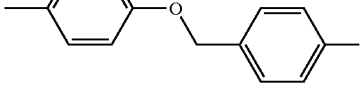 |
| I-692 | 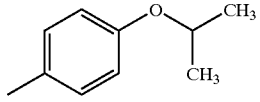 |
| I-693 | 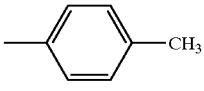 |
| I-694 | 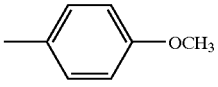 |
| I-695 |  |
| I-696 |  |

TABLE 15-continued (I-f-15)

[Structure: pyridine-pyrroline-phenyl-R¹]

| Example No. | R¹ |
|---|---|
| I-697 | -C₆H₄-C(O)CH₃ (4-acetylphenyl) |
| I-698 | —(CH₂)₃—CH₃ |
| I-699 | 4-Br-C₆H₄— |
| I-700 | 4-SCF₃-C₆H₄— |
| I-701 | 4-S(O)CF₃-C₆H₄— |
| I-702 | 4-S(O)₂CF₃-C₆H₄— |
| I-703 | 4-SCHF₂-C₆H₄— |
| I-704 | 4-S(O)CHF₂-C₆H₄— |
| I-705 | 4-S(O)₂CHF₂-C₆H₄— |

Preference is furthermore given to the compounds of the formula (I-f-16) listed in Table 16

TABLE 16

(I-f-16)

[Structure: 3-chlorothiophene-pyrroline-phenyl-R¹]

| Example No. | R¹ |
|---|---|
| I-706 | —OH |
| I-707 | —O—CH₂—CH=CH₂ |
| I-708 | —O—CH₂—C₆H₄-4-OCF₃ |
| I-709 | —O—CH₂—C₆H₄-4-Cl |
| I-710 | —O—C₆H₄-4-OCF₃ |
| I-711 | —O—CH₂—C₆H₄-4-CF₃ |
| I-712 | —O—CH₂—C₆H₃-2,4-Cl₂ |
| I-713 | —O—CH₂—C₆H₄-2-Cl |
| I-714 | —O—CH₂—C₆H₃-3,4-Cl₂ |
| I-715 | —O—CH₂—C₆H₄-3-Cl |

TABLE 16-continued (I-f-16)

| Example No. | R¹ |
|---|---|
| I-716 | —O—CH₂—C₆H₄—SCF₃ |
| I-717 | —O—CH₂—C₆H₃(CH₃)₂ |
| I-718 | —O—CH₂—C₆H₄—C(CH₃)₃ |
| I-719 | —O—CH₂—C₆H₄—cyclohexyl |
| I-720 | —O—CH₂—C≡CH |

Preference is furthermore given to the compounds of the formula (I-f-17) listed in Table. 17

TABLE 17

(I-f-17)

| Example No. | R¹ |
|---|---|
| I-721 | —C₆H₄—CH(CH₃)₂ |

TABLE 17-continued (I-f-17)

| Example No. | R¹ |
|---|---|
| I-722 | 3,5-dichlorophenyl |
| I-723 | 4-fluorophenyl |
| I-724 | 4-chlorophenyl |
| I-725 | 3-thienyl |
| I-726 | 5-methyl-thiophene-2-CH=N—O—CH₃ |
| I-727 | 4-OCF₃-phenyl |
| I-728 | —Br |
| I-729 | 2,2-difluoro-1,3-benzodioxol-5-yl |
| I-730 | 4-OCF₃-3-F-phenyl |
| I-731 | 3-CF₃-phenyl |
| I-732 | 4-CF₃-phenyl |
| I-733 | 2-OHC-phenyl |

TABLE 17-continued (I-f-17)

| Example No. | R¹ |
|---|---|
| I-734 | 4-CHO-phenyl |
| I-735 | 4-COOH-phenyl |
| I-736 | 4-methyl-2-fluoro-phenyl (with 2-CH₃, 5-F substitution) |
| I-737 | benzothiophen-2-yl (methyl-substituted) |
| I-738 | 2,2-difluoro-benzo[1,3]dioxol-5-yl (methyl-substituted) |
| I-739 | 3,5-bis(trifluoromethyl)phenyl |
| I-740 | H |
| I-741 | 3-acetyl-phenyl (with methyl) |
| I-742 | 4-(CH=N-O-CH₃)-phenyl |
| I-743 | 3-propionyl-phenyl (with methyl) |
| I-744 | 4-propionyl-phenyl |
| I-745 | 4-(CH=N-O-CH₂CH₃)-phenyl |
| I-746 | 4-(S-CH(CH₃)₂)-phenyl |
| I-747 | 4-(O-CH(CH₃)₂)-phenyl |
| I-748 | 1-methyl-naphthalenyl |
| I-749 | 4-(C(CH₃)=N-O-CH₂CH₃)-phenyl |
| I-750 | 4-(C(CH₂CH₃)=N-O-CH₃)-phenyl |
| I-751 | 4-isobutyl-phenyl |
| I-752 | 4-(CH₂-S-CH(CH₃)₂)-phenyl |
| I-753 | 4-methyl-biphenyl |
| I-754 | 4-pentyl-phenyl |

TABLE 17-continued (I-f-17)

[Structure: 3-(trifluoromethyl)thiophene connected to a pyrroline ring with N, bearing a 4-R¹-phenyl substituent]

| Example No. | R¹ |
|---|---|
| I-755 | —C₆H₄—CH₂—O—C₆H₄—Cl (4-((4-chlorophenoxy)methyl)phenyl) |
| I-756 | —C₆H₄—O—CH₂—C₆H₄—Cl |
| I-757 | —C₆H₄—CH₃ |
| I-758 | —C₆H₄—OCH₃ |
| I-759 | —C₆H₄—C(O)CH₃ |
| I-760 | —(CH₂)₃—CH₃ |
| I-761 | —C₆H₄—Br |
| I-762 | —C₆H₄—SCF₃ |
| I-763 | —C₆H₄—S(O)—CF₃ |
| I-764 | —C₆H₄—S(O)₂—CF₃ |
| I-765 | —C₆H₄—SCHF₂ |
| I-766 | —C₆H₄—S(O)—CHF₂ |

TABLE 17-continued (I-f-17)

[Structure: same as above]

| Example No. | R¹ |
|---|---|
| I-767 | —C₆H₄—S(O)₂—CHF₂ |

Preference is furthermore given to the compounds of the formula 1 (I-f-18) listed in Table 18

TABLE 18

(I-f-18)

[Structure: 2-pyridyl connected to a pyrroline ring with N, bearing a 4-R¹-phenyl substituent]

| Example No. | R¹ |
|---|---|
| I-768 | —C₆H₄—CH(CH₃)₂ |
| I-769 | 3,5-dichlorophenyl |
| I-770 | —C₆H₄—F |
| I-771 | —C₆H₄—Cl |
| I-772 | 3-thienyl |
| I-773 | 5-(CH=N—OCH₃)-thien-2-yl |
| I-774 | —C₆H₄—OCF₃ |

TABLE 18-continued
(I-f-18)
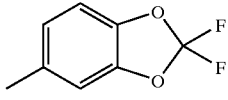
| Example No. | R¹ |
|---|---|
| I-775 | —Br |
| I-776 | 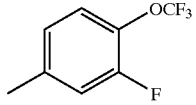 |
| I-777 | 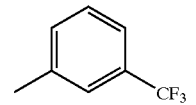 |
| I-778 | 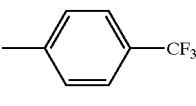 |
| I-779 | 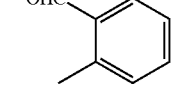 |
| I-780 | 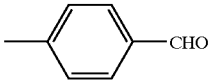 |
| I-781 | 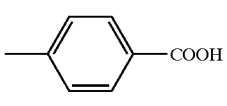 |
| I-782 | 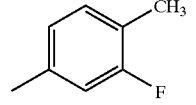 |
| I-783 | 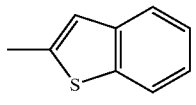 |
| I-784 | 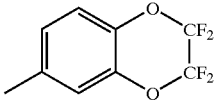 |
| I-785 | 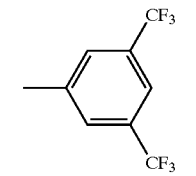 |
| I-786 | 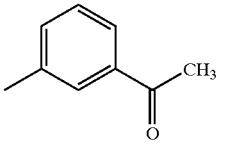 |
TABLE 18-continued
(I-f-18)
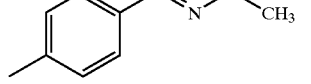
| Example No. | R¹ |
|---|---|
| I-787 | H |
| I-788 | 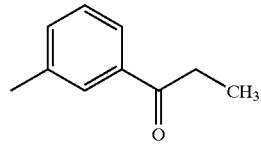 |
| I-789 | 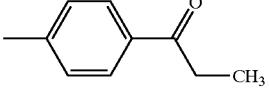 |
| I-790 | 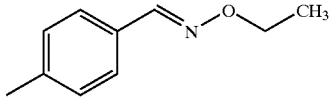 |
| I-791 | 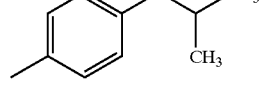 |
| I-792 | 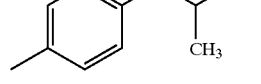 |
| I-793 | 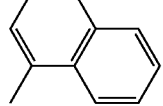 |
| I-794 | 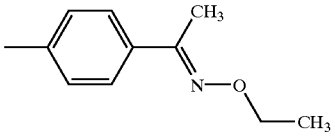 |
| I-795 |  |
| I-796 |  |

TABLE 18-continued
(I-f-18)
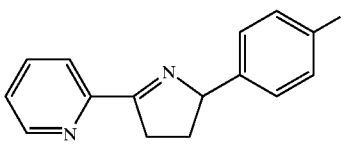
| Example No. | R¹ |
|---|---|
| I-797 | 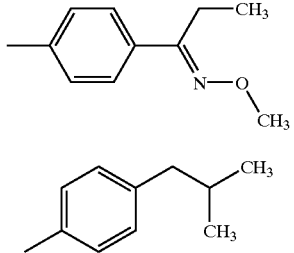 |
| I-798 | 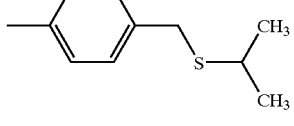 |
| I-799 | 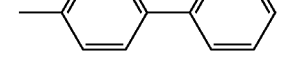 |
| I-800 |  |
| I-801 | 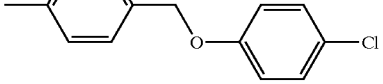 |
| I-802 | 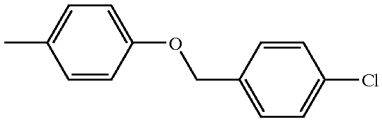 |
| I-803 | 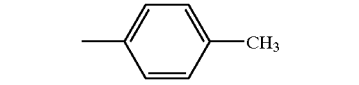 |
| I-804 | 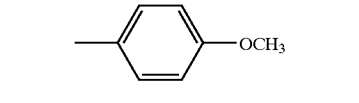 |
| I-805 | 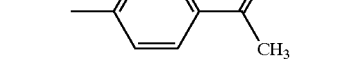 |
| I-806 | 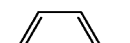 |
| I-807 | —(CH₂)₃—CH₃ |
| I-808 | 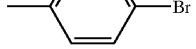 |
TABLE 18-continued
(I-f-18)
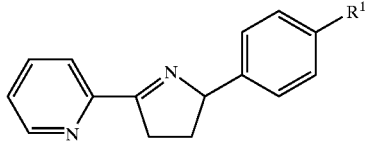
| Example No. | R¹ |
|---|---|
| I-809 | 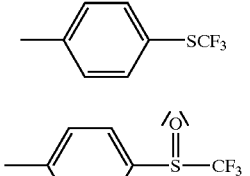 |
| I-810 | 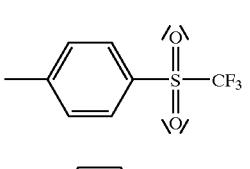 |
| I-811 | 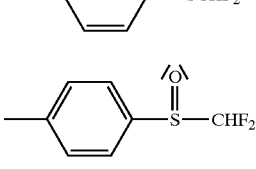 |
| I-812 | 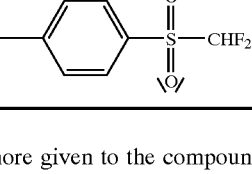 |
| I-813 | 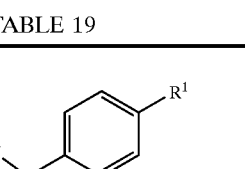 |
| I-814 | 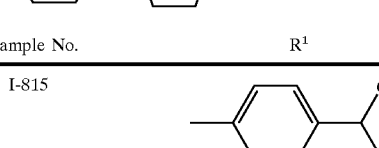 |
Preference is furthermore given to the compounds of the formula (I-f-19) listed in Table 19
TABLE 19
(I-f-19)
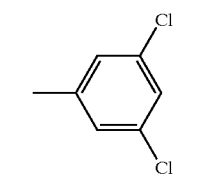
| Example No. | R¹ |
|---|---|
| I-815 | 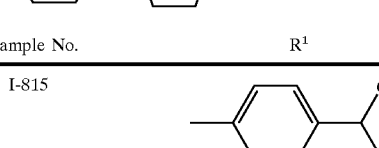 |
| I-816 | 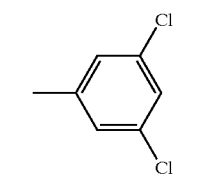 |

TABLE 19-continued (I-f-19)

| Example No. | R¹ |
|---|---|
| I-817 | 4-F-phenyl |
| I-818 | 4-Cl-phenyl |
| I-819 | thiophen-3-yl |
| I-820 | 5-(CH=N-OCH₃)-thiophen-2-yl |
| I-821 | 4-OCF₃-phenyl |
| I-822 | —Br |
| I-823 | 2,2-difluoro-benzo[1,3]dioxol-5-yl |
| I-824 | 4-OCF₃-3-F-phenyl |
| I-825 | 3-CF₃-phenyl |
| I-826 | 4-CF₃-phenyl |
| I-827 | 2-CHO-phenyl (OHC-) |
| I-828 | 4-CHO-phenyl |
| I-829 | 4-COOH-phenyl |
| I-830 | 4-CH₃-3-F-phenyl |
| I-831 | benzo[b]thiophen-2-yl |
| I-832 | 2,2-difluoro-benzo[1,3]dioxol-6-yl (CF₂-CF₂) |
| I-833 | 3,5-bis(CF₃)-phenyl |
| I-834 | H |
| I-835 | 3-C(=O)CH₃-phenyl |
| I-836 | 4-(CH=N-OCH₃)-phenyl |
| I-837 | 3-C(=O)CH₂CH₃-phenyl |
| I-838 | 4-C(=O)CH₂CH₃-phenyl |
| I-839 | 4-(CH=N-OCH₂CH₃)-phenyl |
| I-840 | 4-S-CH(CH₃)₂-phenyl |

TABLE 19-continued
(I-f-19)
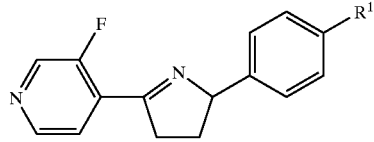
| Example No. | R¹ |
|---|---|
| I-841 | 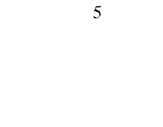 |
| I-842 | 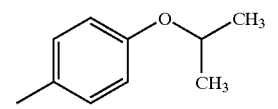 |
| I-843 | 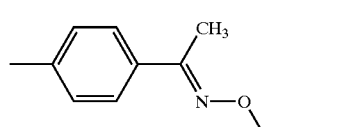 |
| I-844 | 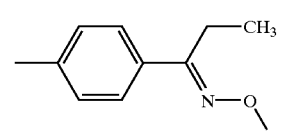 |
| I-845 | 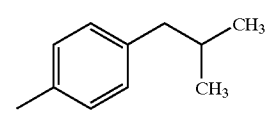 |
| I-846 | 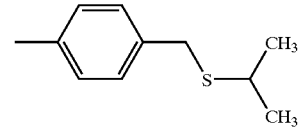 |
| I-847 | 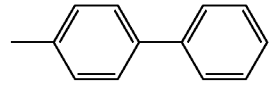 |
| I-848 |  |
| I-849 | 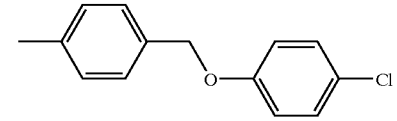 |
| I-850 | 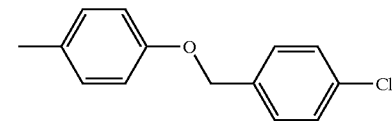 |
TABLE 19-continued
(I-f-19)
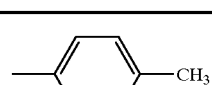
| Example No. | R¹ |
|---|---|
| I-851 | 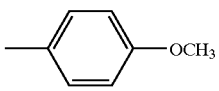 |
| I-852 | 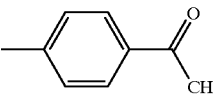 |
| I-853 | 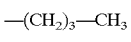 |
| I-854 | —$(CH_2)_3$—$CH_3$ |
| I-855 | 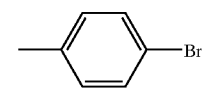 |
| I-856 | 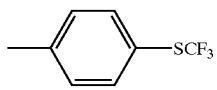 |
| I-857 | 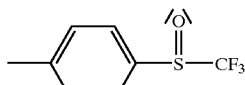 |
| I-858 | 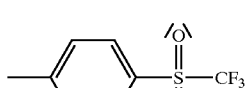 |
| I-859 | 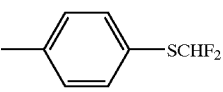 |
| I-860 | 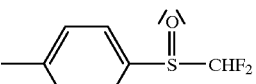 |
| I-861 | 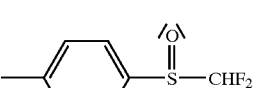 |

Preference is furthermore given to the compounds of the formula (I-f-20) listed in Table 20

TABLE 20

(I-f-20)

| Example No. | R¹ |
|---|---|
| I-862 | 4-isopropylphenyl |
| I-863 | 3,5-dichlorophenyl |
| I-864 | 4-fluorophenyl |
| I-865 | 4-chlorophenyl |
| I-866 | thiophen-3-yl (3-methylthiophene position) |
| I-867 | 5-(methoxyiminomethyl)thiophen-2-yl |
| I-868 | 4-trifluoromethoxyphenyl |
| I-869 | —Br |
| I-870 | 2,2-difluoro-1,3-benzodioxol-5-yl |
| I-871 | 4-trifluoromethoxy-3-fluorophenyl |
| I-872 | 3-trifluoromethylphenyl |
| I-873 | 4-trifluoromethylphenyl |

TABLE 20-continued (I-f-20)

| Example No. | R¹ |
|---|---|
| I-874 | 2-methyl-6-formylphenyl (OHC, CH₃ on phenyl) |
| I-875 | 4-formylphenyl (CHO) |
| I-876 | 4-carboxyphenyl (COOH) |
| I-877 | 4-methyl-3-fluorophenyl (CH₃, F) |
| I-878 | benzothiophen-2-yl |
| I-879 | 2,2-difluoro-1,3-benzodioxin (CF₂-CF₂) |
| I-880 | 3,5-bis(trifluoromethyl)phenyl |
| I-881 | H |
| I-882 | 3-acetylphenyl |
| I-883 | 4-(methoxyiminomethyl)phenyl |
| I-884 | 3-propionylphenyl |

TABLE 20-continued
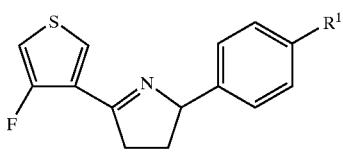
(I-f-20)
| Example No. | R¹ |
|---|---|
| I-885 | 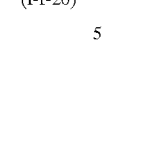 |
| I-886 | 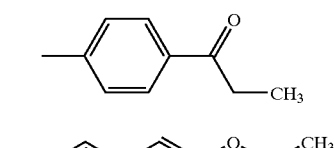 |
| I-887 | 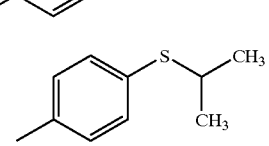 |
| I-888 | 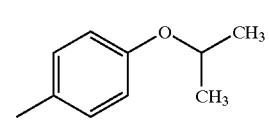 |
| I-889 | 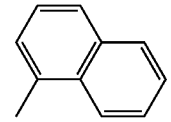 |
| I-890 | 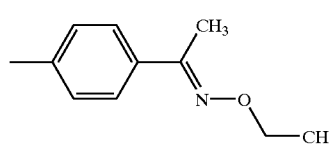 |
| I-891 | 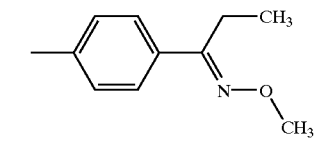 |
| I-892 | 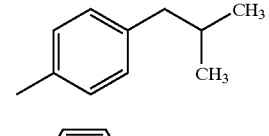 |
| I-893 | 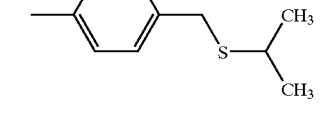 |
| I-894 | 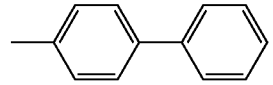 |
| I-895 | 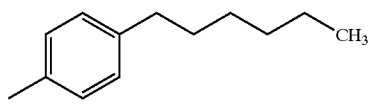 |
TABLE 20-continued
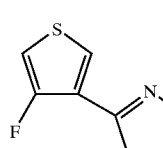
(I-f-20)
| Example No. | R¹ |
|---|---|
| I-896 | 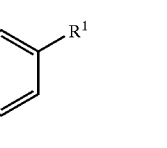 |
| I-897 | 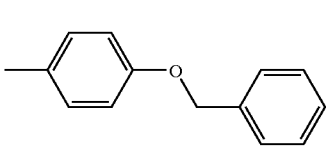 |
| I-898 | 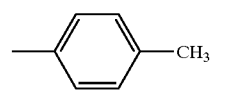 |
| I-899 | 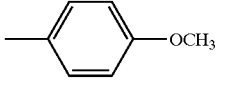 |
| I-900 | 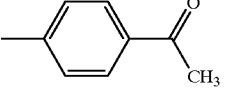 |
| I-901 | —(CH$_2$)$_3$—CH$_3$ |
| I-902 | 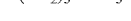 |
| I-903 | 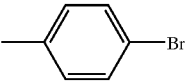 |
| I-904 | 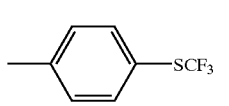 |
| I-905 | 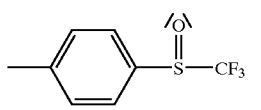 |
| I-906 | 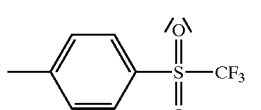 |
| I-907 | 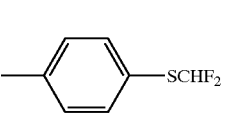 |

TABLE 20-continued

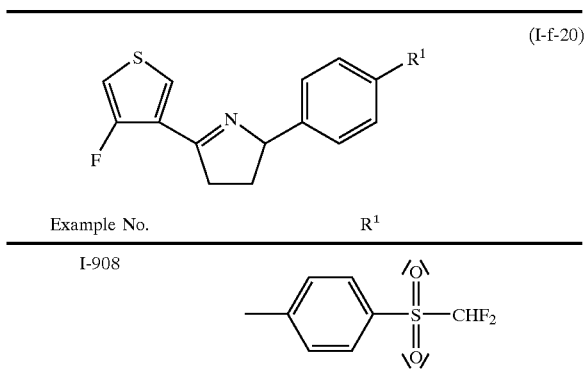

| Example No. | R¹ |
|---|---|
| I-908 | |

The abovementioned general or preferred radical definitions or illustrations can be combined with one another as desired, i.e. including combinations between the respective ranges and preferred ranges. They apply to the end products and, correspondingly, to the precursors and intermediates.

Preference according to the invention is given to the compounds of the formula (f) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals, such as alkyl or alkenyl, can be in each case straight-chain or branched as far as this is possible, including in combination with heteroatoms, such as, for example, in alkoxy.

Optionally substituted radicals can be mono- or polysubstituted, and in the case of polysubstitution, the substituents can be identical or different. A plurality of radicals having the same indices, such as, for example, m radicals $R^2$ for m >1, can be identical or different.

Using, for example, tBOC-[1-(4-ethyl-2-methyl-phenyl)-3-(-2-carboxylthienyl-)-1-propyl]-amine as starting material, the course of the reaction in the process (A) according to the invention can be represented by the following formula scheme:

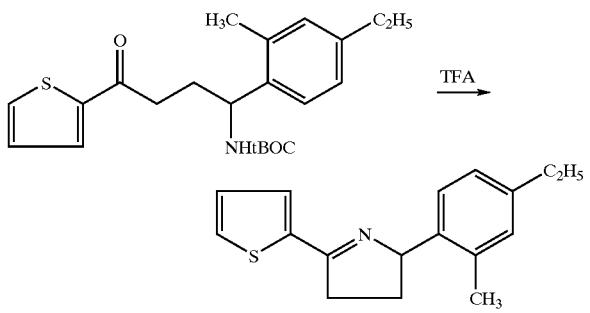

Using, for example, 2-(4-methoxyphenyl)-cyclobutane O-methanesulphonyloxime and 2-thienylmagnesium bromide as starting materials, the course of the reaction in; the process (B) according to the invention can be represented by the following formula scheme:

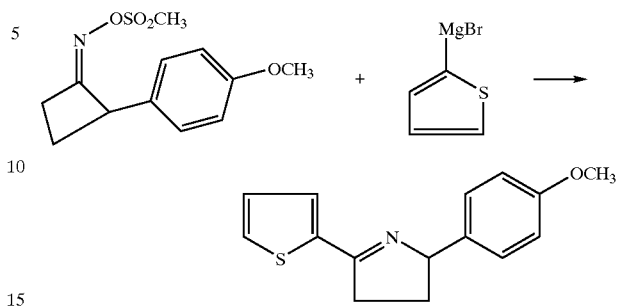

Using, for example, 2-(2-thienyl)-5-(4-iodophenyl)-3,4-dihydro-2H-pyrrole and 4-cyanomethoxyphenylboronic acid as starting materials, the course of the reaction in the process (C) according to the invention can be represented by the following formula scheme:

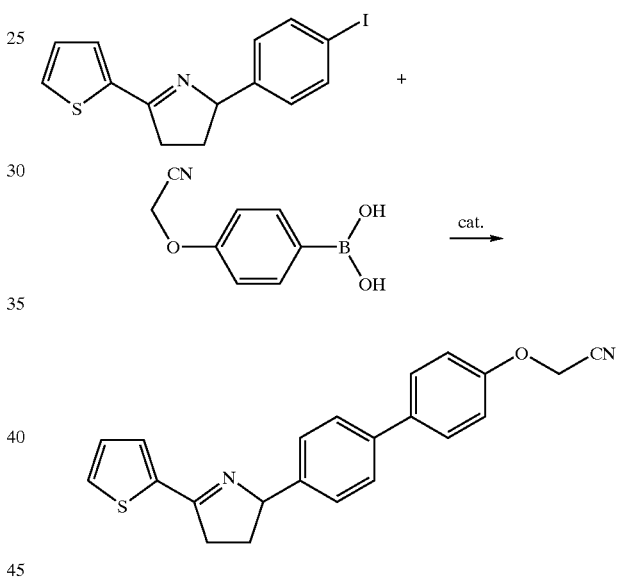

Using, for example, 2-(2-thienyl)-5-(3'-chloro-4'-hydroxybiphenyl-4-yl)-3,4-dihydro-2H-pyrrole and methyl α-bromovalerate as starting materials, the course of the reaction in the process (D) according to the invention can be represented by the following formula scheme:

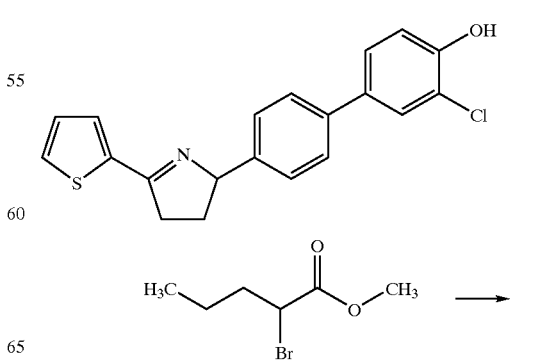

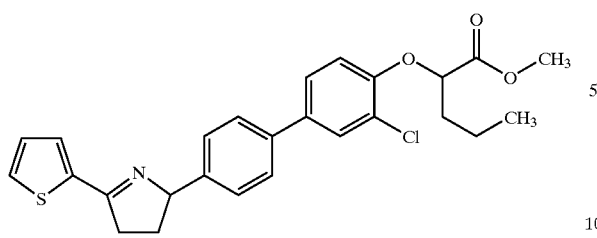

Using, for example, 5-(4'-cyclopropylcarbonylmethoxy-3-trifluoromethoxy-biphenyl-4-yl)-2-(2-thienyl)-3,4-dihydro-2H-pyrrole and O-methylhydroxylamine as starting materials, the course of the reaction in the process (E) according to the invention can be represented by the following formula scheme:

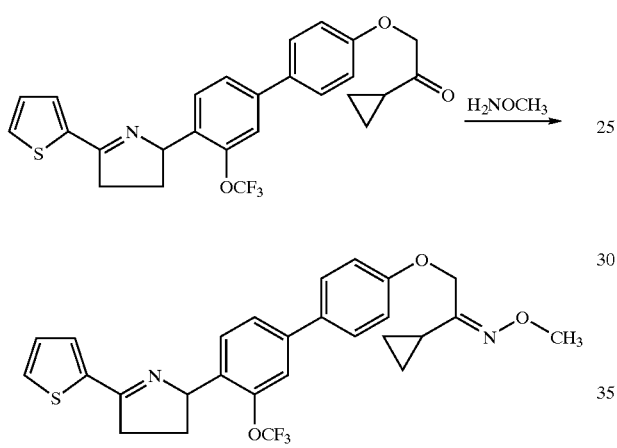

Using, for example, 4-bromobenzyl cyanide and 2-methylcarbonylthiophene, the course of the reaction in the process (F) according to the invention can be represented by the following formula scheme:

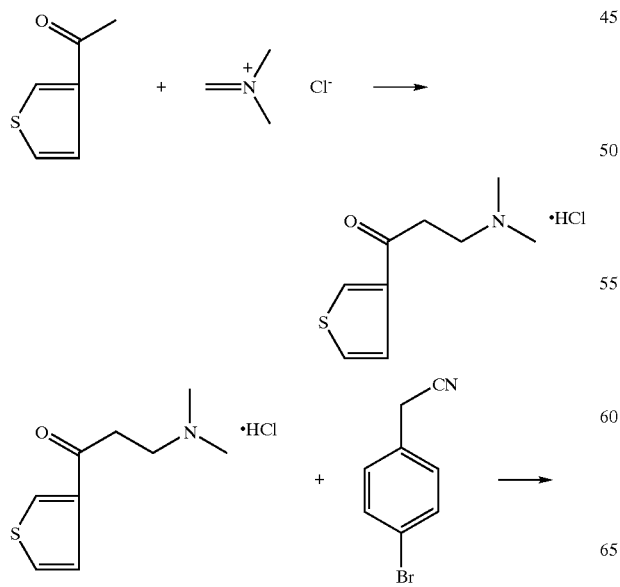

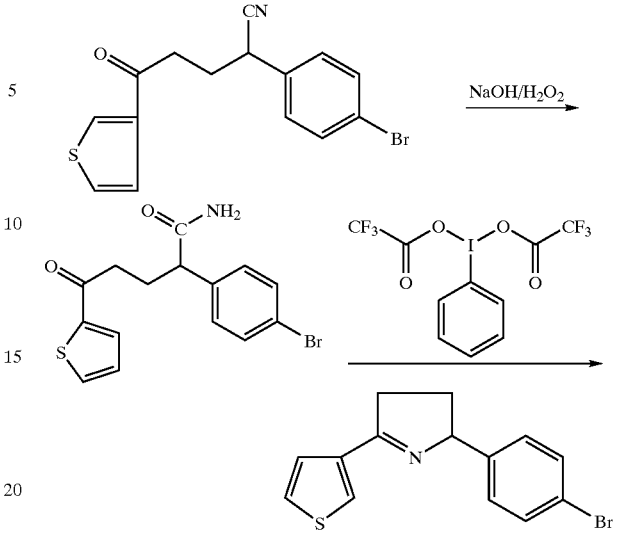

Using, for example, 5-phenylpyrrolidin-2-one, the course in the process (G) according to the invention can be represented by the following formula scheme:

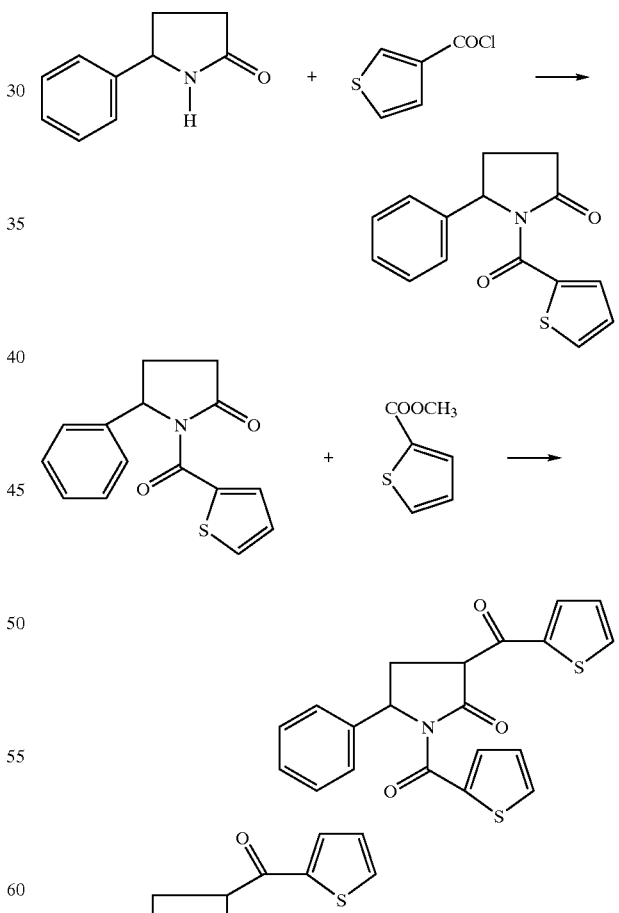

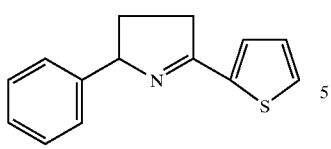

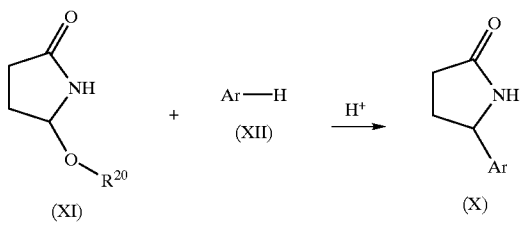

The formula (II) provides a general definition of the aminoketone derivatives required for carrying out the process (A) according to the invention. In this formula, Ar and Hetaryl preferably have those meanings which have already been mentioned in connection with the description of the cyclic imines of the formula (I) as being preferred.

Aminoketone derivatives of the formula (II) can be prepared, for example, by reacting BOC-protected lactams of the formula (VIB) with metallated heteroaromatics of the formula (IX) at temperatures between 0° C. and 80° C. in accordance with the reaction scheme below:

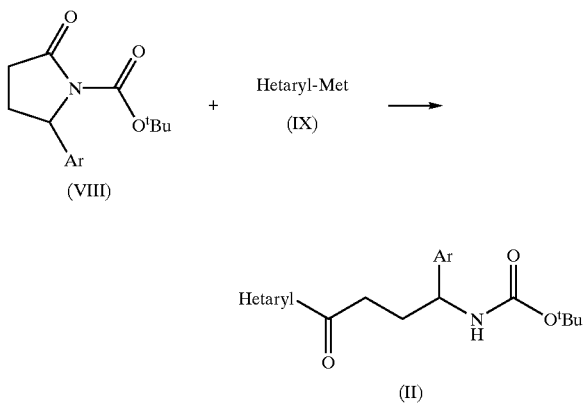

In the formula (IX), Met represents a monovalent metal radical, such as Li, MgI, MgBr or MgCl.

Some metallated hetaryls of the formula (IX) are known, or they can be prepared by known methods, such as, for example, lithiation or Grignard reaction, from the corresponding hetaryls or halogenated hetaryls.

Protected lactams of the formula (VIII) are obtained, for example, by BOC-protecting lactams of the formula (X) by customary methods, such as, for example, metallation with butyllithium and reaction with di-tert-butyl dicarbonate (cf., for example, T. W. Greene, P. G. M. Wuts, Protective Groups in Organic Synthesis, 2. Ed., John Wiley & Sons, New York 1991).

Lactams of the formula (X) can be prepared, for example, starting with ω-alkoxylactams of the formula (XI), according to two methods. They can be reacted with aromatics of the formula (XII) in the presence of an acidic catalyst, such as, for example, sulphuric acid, acetic acid or aluminium chloride, and, if appropriate, in the presence of a diluent, such as, for example, dichloromethane or acetonitrile, in accordance with the reaction scheme below [see also WO 98/22 438]:

Alternatively, they can be reacted with aryl-Grignard reagents of the formula (XIII) in the presence of a diluent, such as, for example, tetrahydrofuran, in accordance with the reaction scheme below [cf. Org. Prep. Proced. Int. 25, 255 (1993)]:

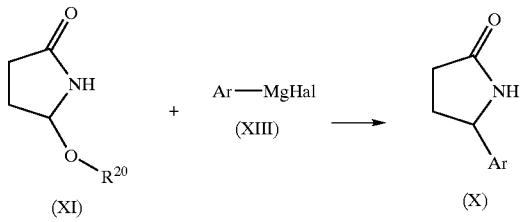

In formula (XI), $R^{20}$ represents methyl or ethyl. In formula (XIII), Hal represents chlorine, bromine or iodine.

The ω-alkoxylactams of the formula (XI) are known, some of them are commercially available, and they can be prepared, for example, from the corresponding unsubstituted imides by cathodic or sodium boronate reduction, or from the unsubstituted lactams by anodic oxidation, in each case in the presence of methanol or ethanol (cf., for example, J. Org. Chem. 56, 1822 (1991); Synthesis 1980, 315).

The aromatics of the formula (XII) are benzene derivatives which are generally known or can be prepared using a wide array of generally known methods of organic chemistry.

The aryl-Grignard reagents of the formula (XIII) can be prepared in a customary manner from the corresponding aryl halides and magnesium. Aryl halides are generally known compounds of organic chemistry.

Lactams of the formula (X) can also be prepared, for example, by cyclizing substituted ω-benzoylcarboxylic acids of the formula (XIV) with a reagent prepared from ammonium carbonate and formic acid at boiling point, in accordance with the following reaction scheme [cf. Recl. Trav. Chim. Bays-Bas 81, 788 (1962), WO 98122 438]:

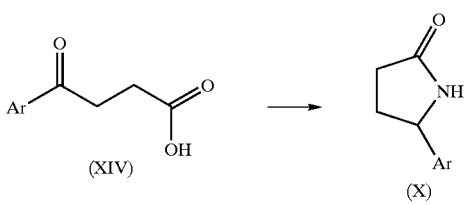

The ω-benzoylcarboxylic acids of the formula (XIV) required for this purpose can be prepared, for example, by reacting the dicarboxylic anhydrides of the formula (XV)

with aromatics of the formula (XII) in the presence of a Lewis acid, such as, for example, aluminium chloride, and, if appropriate, in the presence of a diluent, such as, for example, benzene, in accordance with the reaction scheme below [cf. Recl. Trav. Chim. Bays-Bas 81, 788 (1962)]:

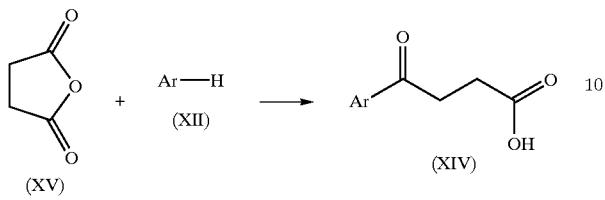

The anhydride required for this purpose (succinic anhydride) is commercially available.

If Ar in the active compound of the formula (I) according to the invention, as in the formula (I-b) given further above, represents an optionally substituted biphenynyl, the corresponding biphenyllactams of the formula (X-a) can be, prepared in an advantageous variant of the process described here by reacting, analogously to the process (C) described above and further below, certain phenyllactams of the formula (XVI) with boronic acids of the formula (VI), in accordance with the following reaction scheme:

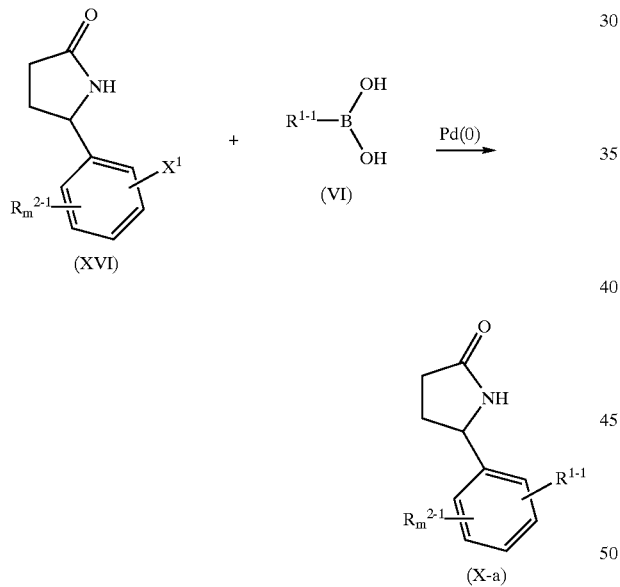

The phenyllactams of the formula (XVI) in which $X^1$ represents bromine or iodine are a subset of the compounds of the formula (X) whose preparation is described above. The phenyllactams of the formula (XVI) in which $X^1$ represents trifluoromethanesulphonyl can be prepared by the method of process (C) from the corresponding compounds of the formula (X) in which Ar is substituted by $R^1$=hydroxyl.

The novel 2H-pyrrole derivatives of the formula (I) can also be prepared, for example, by reducing the nitro group of the nitroketones of the formula (XVII) which are also novel in a process (A.b) according to the following reaction scheme:

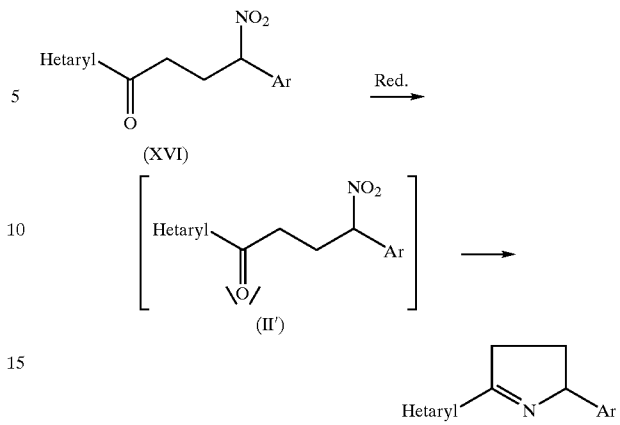

Here, an aminoketone intermediate of the formula (II') is formed; however, this is cyclocondensed in situ to (I), in particular in acidic medium.

The reduction can be carried out by catalytic hydrogenation or other generally known, methods for reducing nitro groups (cf., for example, Houben-Weyl, Methoden der Organischen Chemie, Georg Thieme Verlag Stuttgart, volume 11/1, 394 409 and volume 4/1c, 490 506).

Nitroketones of the formula (XVII) can be prepared, for example, by condensing ω-chloroalkyl hetaryl ketones of the formula (XX) in the presence of a diluent, such as, for example, methanol, ethanol, another lower aliphatic alcohol or else tetrahydrofuran and in the presence of an acid binder, such as, for example, sodium hydride or an alkali metal alkoxide, preferably that which corresponds to the alcohol used as diluent, in accordance with the reaction scheme below:

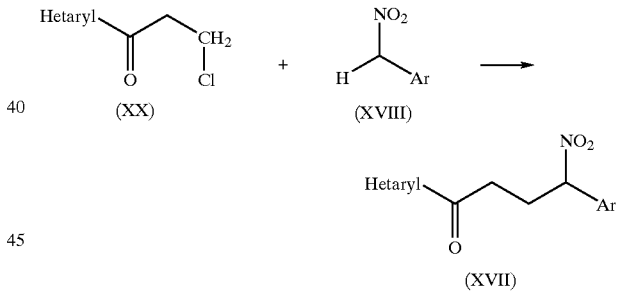

The ω-chloroalkyl hetaryl ketones of the formula (XX) can be prepared in a known manner, such as, for example, by Friedel-Crafts acylation of hetaryls of the formula (XXI) (see further below) with 3-chloropropionyl chloride.

The nitromethylbenzenes of the formula (XVIII) are known or can be prepared in a known manner, such as, for example, by nitration of corresponding toluenes in the side-chain or reaction of corresponding benzyl halides with silver nitrite [cf., for example, J. Am. Chem. Soc. 77, 6269 (1955); J. Am. Chem. Soc 86, 2681 (1964); Houben-Weyl, Methoden der Organischen Chemie, Georg Thieme Verlag Stuttgart, volume 10/1, 46–57 (substitution of halogen), volume E16, 145–154 (both methods)]. The toluenes or benzyl halides required for this purpose are generally known compounds of organic chemistry.

The nitroketones of the formula (XVII) can be prepared, for example, by Michael additions of nitromethylbenzenes of the formula (XVIII) to hetaryl vinyl ketones of the formula (XIX) in the presence of a diluent, such as, for example, methanol, ethanol or another lower aliphatic alcohol and in the presence of an acid binder, such as, for example, preferably an alkali metal alkoxide which corresponds to the alcohol used as diluent, in accordance with the reaction scheme below (cf., for example, J. Prakt. Chem., series 4, 1, 57 (1955); Houben-Weyl, Methoden der Organischen Chemie, Georg Thieme Verlag Stuttgart, volume 10/1, 199-206):

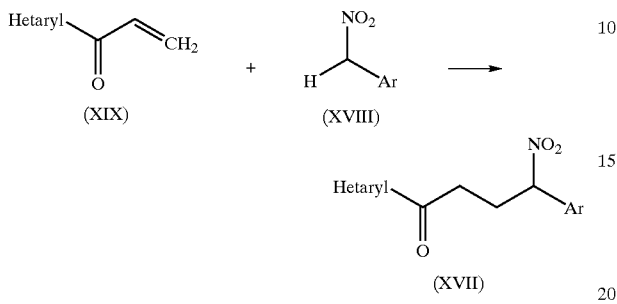

The hetaryl vinyl ketones of the formula (XIX) can be prepared, for example, by eliminating hydrogen chloride from β-chloropropyl ketones of the formula (XX), which can be obtained, for example, by Friedel-Crafts acylation of hetaryls of the formula (XXI) with 3-chloropropionyl chloride, in the presence of an acid binder, such as, for example, potassium acetate, in the presence of a diluent, such as, for example, methanol, in accordance with the reaction scheme below [cf., for example, J. Prakt. Chem., series 4, 1, 57 (1955)]:

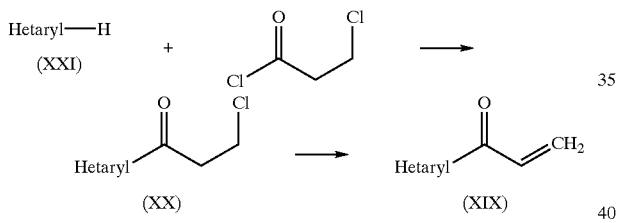

Hetaryls are available commercially or by generally known methods of organic chemistry.

The hetaryl vinyl ketones of the formula (XIX) can also be prepared by reacting O-methyl methyl-hetarylhydroxamates of the formula (XXII) with vinylmagnesium bromide, in accordance with the following reaction scheme:

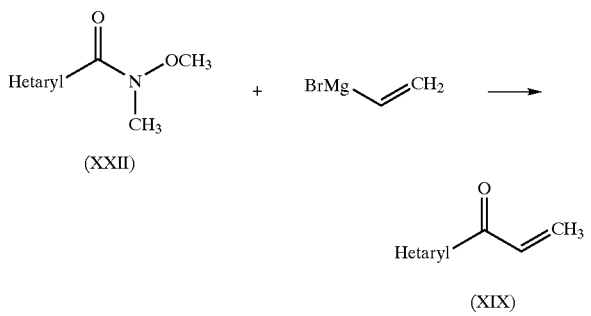

The O-methyl methyl-hetarylhydroxamates of the formula (XXII) can be prepared by known methods, for example from the corresponding, carboxylic acid derivatives [cf., for example, analogously to Tetrahedron Lett. 22, 3815 (1981)].

Since the hetaryl vinyl ketones of the formula (XIX) are sensitive, they are, in a preferred variant of preparing the nitroketones of the formula (XVII), directly reacted further with nitromethylbenzenes of the formula (XVIII).

Nitroketones of the formula (XVII) can also be prepared by adding, in accordance with the reaction scheme below, enamines of hetaryl methyl ketones of the formula (XXV) to α-nitrostyrenes of the formula (XXVI), followed by acid hydrolysis of the reaction product:

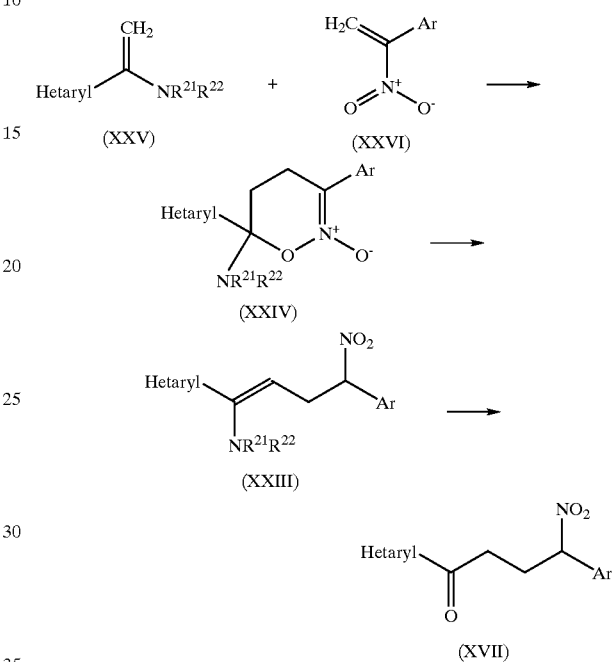

In the formulae (XXIII), (XXIV) and (XXV), $R^{21}$ and $R^{22}$ together with the nitrogen atom to which they are attached represent a cyclic amino radical, such as, for example, 1-pyrrolidino, 1-piperidino or 4-morpholino.

In most instances, the addition proceeds in a [4+2]-cycloaddition to afford 1,2-oxazine N-oxide derivatives of the formula (XXIV) which can be isolated, and the reaction is, if appropriate, carried out in the presence of a non-polar diluent, such as, for example, diethyl ether, at, for example, from −80° to +20° C. The hydrolysis is carried out using, for example, aqueous mineral acids, such as hydrochloric acid, if appropriate in the presence of methanol or ethanol [cf., for example, Helv. Chim. Acta 68, 162 (1985); Tetrahedron 45, 2099 (1989)]. In many instances, it is advantageous first to open the ring to afford compounds of the formula (XXIII) by simple dissolution of the 1,2-oxazine N-oxide derivative in methanol or ethanol, since the undesirable Nef reaction which yields the corresponding diketo compound will otherwise take place as a competing reaction [cf., for example, Tetrahedron 45, 2099(1989)].

Some of the enamines of the formula (XXV) are known, or they can be prepared, for example, from appropriately substituted hetaryl ketones and cyclic amines by standard procedures (for example Org. Syntheses Vol. 58, 56, John Wiley & Sons, New York). Some of the hetaryl ketones required for this purpose are commercially available or known, or they can be prepared by known methods of the chemistry of aromatics.

Some of the nitrostyrenes of the formula (XXVI) are known, or they can be prepared, for example, by formulation of the nitromethylbenzenes of the formula (XVIII) given above (cf, for example, Houben-Weyl, Methoden der Organischen Chemie, Georg Thieme Verlag, Stuttgart, volume E16, 215).

Novel 2H-pyrrole derivatives of the formula (I) can also be prepared, for example, by hydrolysing imines of the formula (XXVII) in a process (A.c) according to the following reaction scheme:

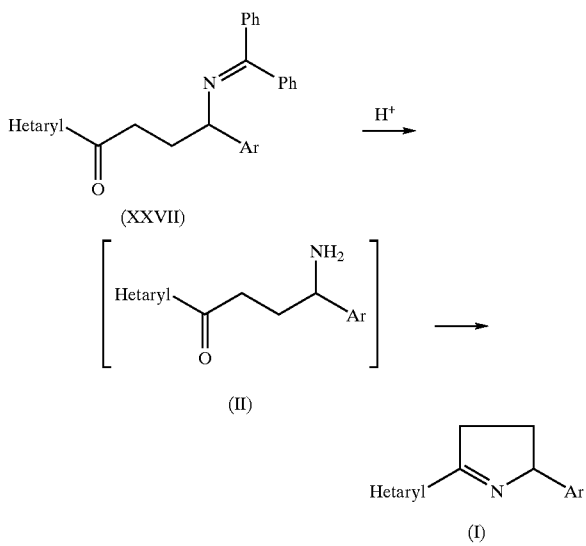

The hydrolysis can be carried out by generally known methods by using, for example, aqueous hydrochloric acid. Here, too, the aminoketone intermediates of the formula (II') cyclocondense in situ to give the compounds of the formula (I).

The imines of the formula (XXVII) can be prepared, for example, by carrying out Michael additions of N-diphenylmethylenebenzylamines of the formula (XVIII) to the hetaryl vinyl ketone of the formula (XIX), according to the following reaction scheme:

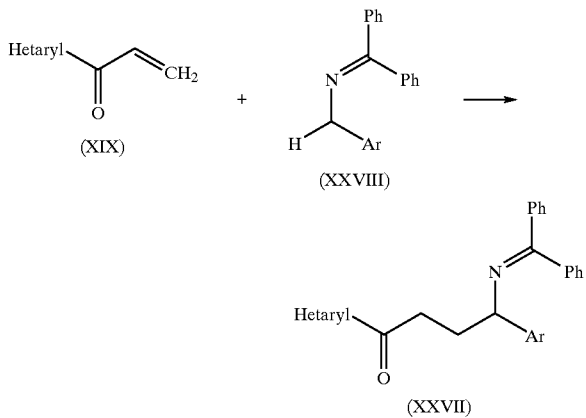

The addition is carried out in the presence of an acid binder and in the presence of a diluent, such as, for example, acetonitrile or dichloromethane and, if appropriate, in the presence of a reaction auxiliary, for example at room temperature. A preferred acid binder is aqueous alkali, such as 50% strength aqueous sodium hydroxide solution, in the presence of a phase-transfer catalyst, such as, for example, triethylbenzylammonium chloride as reaction auxiliary [cf., for example, Synth. Commun.17, 211 (1987)].

The preparation of the hetaryl vinyl ketone of the formula (XIX) is described further above. The N-diphenylmethylenebenzylamines of the formula (XXVIII) are obtained, for example, by reacting the corresponding benzylamines with benzophenone (cf., for example, Tetrahedron. Lett. 1978, 2641). The benzylamines required for this purpose are known, or they can be prepared by known methods, such as, for example, aminolysis of the corresponding benzyl halides (see above).

The formula (III) provides a general definition of the cyclic O-methanesulphonyl oximes required for carrying out the process (B) according to the invention. In this formula, Ar preferably has those meanings already mentioned in connection with the description of the cyclic imines of the formula (I) as being preferred. The O-methanesulphonyl oximes of the formula (III) are described in WO 98/22438.

The O-methylsulphonyl oximes of the formula (III) can be prepared, for example, by first converting cyclic α-aryl ketones of the formula (XXX) by generally known methods into their oximes of the formula (XXIX) and then reacting these with methanesulphonyl chloride analogously to the mesylation of alcohols, according to the following reaction scheme:

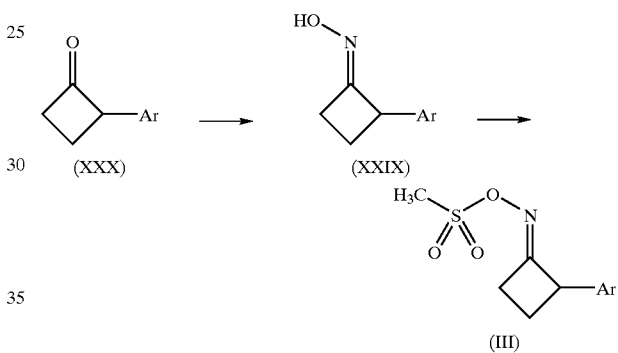

Cyclic α-aryl ketones of the formula (XXX) can be prepared, for example, by epoxidizing 1-arylcycloalkenes of the formula (XXXII) by conventional methods, for example using m-chloroperbenzoic acid, to give oxiranes of the formula (XXXI), and then isomerizing these by acid work-up, according to the following reaction scheme [cf., for example, Tetrahedron 30, 2027 (1974)]:

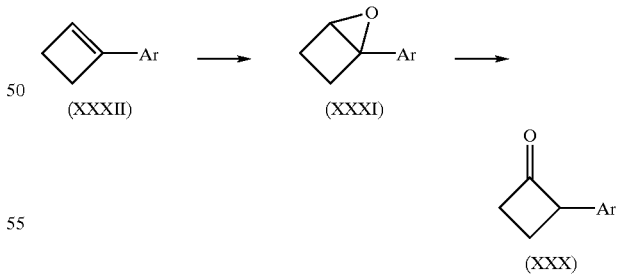

Of course, it is also possible to isomerize oxiranes of the formula (XXXI) obtained by different routes to cyclic α-arylketones of the formula (XXX), for example by shaking a solution in chloroform with 20% strength sulphuric acid.

1-Arylcycloalkenes of the formula (XXXII) can be prepared, for example, by reacting the aryl-Grignard reagents of the formula (XIII) described further above with cyclobutanone of the formula (XXXIV) under usual Grignard conditions and dehydrating the cyclic benzyl alcohols of the formula (XXXIII), for example obtained in this manner, according to the reaction scheme below:

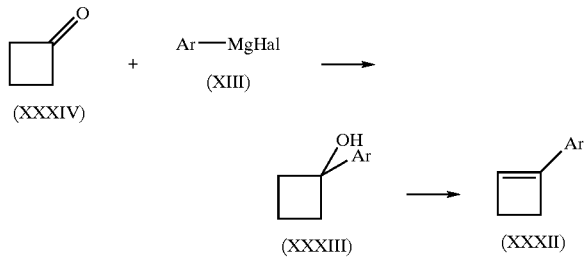

The dehydration can be carried out, for example, by dissolving the alcohol in a solvent of low polarity, such as hexane, and stirring with half-concentrated sulphuric acid, for example at from 0° C. to 20° C. [cf., for example, Tetrahedron 30, 2027 (1974)].

Cyclobutanone of the formula (XXXIV) is commercially available.

Hetaryl-Grignard reagents of the formula (IV) can be prepared by Grignard reaction from the corresponding hetaryl halides and magnesium. Hetaryl halides are generally known compounds of organic chemistry.

The cyclic imines of the formula (V) required for carrying out process (C) according to the invention are, in as far as $X^1$ represents bromine, hydroxyl or iodine, subsets of the compounds of the general formula (I) according to the invention and can be prepared, for example, by process (A) or (B). If $X^1$ represents trifluoromethanesulphonyl, the compounds of the formula (V-a) can be prepared by reaction of hydroxyl compounds of the formula (I-h), which can also be prepared by process, (A) or (B) using trifluoromethanesulphonyl chloride or trifluorromethanesulphonic anhydride in the presence of an acid binder, such as, for example, pyridine, and, if appropriate, in the presence of a diluent, according to the following reaction scheme:

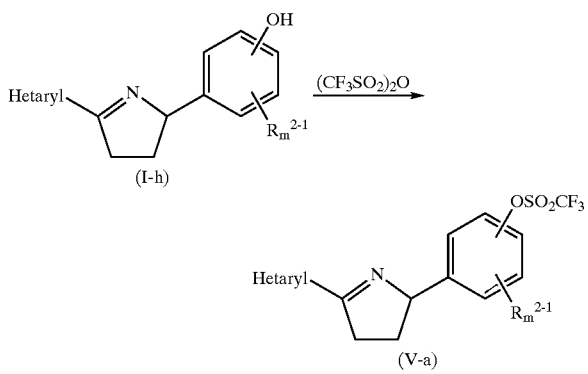

The formula (VI) provides a general definition of the boronic acids also required for carrying out processs (C) α) according to the invention. In this formula, $R^{1-1}$ preferably has those meanings which have already been mentioned in connection with the description of the cyclic imines of the formula (I-b) as being preferred.

Aromatic boronic acids of the formula (VI) are known or can be prepared by known methods [cf. Chem. Rev. 45, 2457 (1995); Pure Appl. Chem. 66, 213 (1994)].

The compounds of the formula $$R^{1-1}-Ab$$

required for carrying out the process (C) β) are known, and some of them are commercially available (see textbooks of organic chemistry and also catalogues of relevant fine-chemicals traders).

The cyclic imines of the formula (I-d) required for carrying out the process (D) according to the invention are subsets of the compounds of the general formula (I) according to the invention and can be prepared, for example, by processes (A) to (C).

The formula (VII) provides a definition of the compounds further required for carrying out the process (D) according to the invention. In this formula, $R^7$, $R^8$, G. p, q and r each preferably have those meanings which have already been mentioned in connection with the description of the cyclic imines of the formula (I) as being preferred. Ab represents a conventional leaving group, such as, for example, haloen, in particular chlorine or bromine; alkylsulphonyloxy, in particular methylsulphonyloxy; or optionally substituted arylsulphonyloxy; in particular phenylsulphonyloxy, p-chlorophenylsulphonyloxy or p-tolylsulphonyloxy.

The compounds of the formula (VII) are generally known compounds of organic chemistry.

The compounds of the formula (F-I), (F-II), (F-IV) and (F-VII) furthermore required for carrying out the process (F) according to the invention are generally known compounds of organic chemistry.

The hetarylcarbonyl chlorides and methyl hetarylcarbonates required for carrying out the process (G) according to the invention are available commercially or by generally known processes of organic chemistry. This also applies to the starting materials dialkylamine, acetylene and formaldehyde required for carrying out the variants.

The process (A) according to the invention is, if appropriate, carried out in the presence of a suitable acid acceptor. Suitable acid acceptors are all customary inorganic or organic bases. These preferably include alkaline earth metal or alkali metal hydroxides, amides, alkoxides, acetates, carbonates or bicarbonates, such as, for example, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (A) according to the invention is, if appropriate, carried out in the presence of a diluent. Suitable diluents are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether.

The reaction temperature for the process (A) according to the invention can be varied within a relatively wide range. In general, the reaction is carried out at temperatures between −50° C. and +150° C., preferably between −20° C. and +100° C.

Suitable diluents for carrying out the process (B) according to the invention are inert organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole.

Preference is given to using a solution of the Grignard reagent of the formula (IV) in an ether and a solution of the O-methylsulphonyl oxime of the formula (III) in a hydrocarbon.

The reaction temperature for the process (B) according to the invention can be varied within a relatively wide range. In general, the reaction is carried out at temperatures between −100° C. and +50° C., preferably between −80° C. and +30° C.

When carrying out the process (B) according to the invention, the Grignard reagent of the formula (IV) and the O-methylsulphonyl oximes of the formula (III) are employed in a molar ratio of from 1:1 to 3:1, preferably from 1:1 to 2:1.

Suitable catalysts for carrying out the process (C) according to the invention are palladium(0) complexes. Preference is given, for example, to tetrakis(triphenylphosphine)palladium.

Suitable acid acceptors for carrying out the process (C) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-di-methylaniline, N,N-dimethylbenzylamine, pyridine, N-methylpiperidine, N-methyl-morpholine, N,N-dimethylaminopyridine, diazabicyclooctane (DABCO), diazabi-cyclononene (DBN) or diazabicycloundecene (DBU).

Suitable diluents for carrying out the process (C) according to the invention are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether.

The reaction temperature for the process (C) according to the invention can be varied within a relatively wide range. In general, the reaction is carried out at temperatures between 0° C. and +140° C., preferably between 50° C. and +110° C.

When carrying out the process (C) according to the invention, the boronic acids of the formula (VI) and the compounds of the formula (V) are employed in a molar ratio of from 1:1 to 3:1, preferably from 1:1 to 2:1. The catalyst is generally employed in amounts of from 0.005 to 0.5 mol, preferably 0.01 mol to 0.1 mol, per mole of the compound of the formula (V). In general, an excess of base is employed.

The process (D) according to the invention is preferably carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (D) according to the invention can be carried out in the presence of a suitable phase-transfer catalyst. Examples of such catalysts include: tetrabutylammonium iodide, tetrabutylammonium bromide or tetrabutylammonium chloride, tributylmethylphosphonium bromide, trimethyl-$C_{13}/C_{15}$-alkylammonium chloride or trimethyl-$C_{13}/C_{15}$-alkylammonium bromide, dibenzyldimethylammonium methyl sulphate, dimethyl-$C_{12}/C_{14}$-alkylbenzylammonium chloride, 15-crown-5, 18-crown-6 or tris-[2-(2-methoxyethoxy)-ethyl]-amine.

The process (D) according to the invention is preferably carried out in the presence of a diluent. Suitable diluents are, for example, all solvents listed for process (A).

The reaction temperature for the process (D) according to the invention can be varied within a relatively wide range. In general, the reaction is carried out at temperatures between −20° C. and +100° C., preferably between 0° C. and 60° C.

When carrying out the process (D) according to the invention, in general approximately equimolar amounts of the starting materials are employed. However, it is also possible to use an excess of the compound of the formula (VII).

The reactions in accordance with the process E) according to the invention are derivatization reactions known to the person skilled in the art, in particular of carboxylic esters and ketones (cf., for example, Houben-Weyl, Methoden der Organischen Chemie, Georg Thieme Verlag, Stuttgart, vol. VII/2b, in particular 1912 ff; vol. VIII about carboxylic esters and their derivatives; vol. E5, in particular p. 812 ff. and the literature quoted therein).

The steps of the process (F) according to the invention are, if appropriate, carried out in the presence of a diluent. Suitable diluents are water (not for F. α), organic solvents and mixtures of these. Examples include: aliphatic, alicyclic or aromatic hydrocarbons, such as, for example, petroleum ehter, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethaine, diethylene glycol dimethyl ether or anisole; ketones, such as acetone, butanone, methyl isobutyl ketone or cyclohexanone; nitrites, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or, i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature for the individual steps of the process (F) according to the invention can be varied within a relatively wide range. In general, the reactions are carried out at temperatures between –50° C. and 250° C., preferably between –20° C. and +100° C.

When carrying out the process (F), the hetaryl chloromethyl ketone (F-I) and the iminium salt (F-II) are employed in a molar ratio of from 1:1 to 2:1, preferably 1.1:1.

When carrying out the process (F), the compounds of the formula (F-III) and the benzyl cyanide of the formula (F-IV) are employed in a molar ratio of from 1:1 to 1:2, preferably 1:1.05.

When carrying out the process (F), the compounds of the formula (F-V) to NaOH and H$_2$O$_2$ are employed in a ratio of from 1:2.5:5 to 1:5:10, preferably 1:2.5:5, based on the equivalents.

When carrying out the process (F), PIFA (F-VII) and the compounds to be used analogously, such as, for example, NaOBr or iodosobenzene and the compounds of the formula (F-VI) are employed in a molar ratio of from 1:1 to 3:1, preferably from 1:1 to 2:1.

The steps of the process (G) according to the invention are, if appropriate, carried out in the presence of a diluent. Suitable diluents are water (not for G. α and β), organic solvents and mixtures of these. Examples include: aliphatic, alicyclic or aromatic hydrocarbons, such as, for example, petroleum ether, hexane, heptane, cyclohexane, methylcyclohexane, benzene, toluene; xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone, nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature for the individual steps of the process (G) according to the invention can be varied within a relatively wide range. In general, the reactions are carried out at temperatures between –50° C. and 250° C., preferably between –20° C. and +100° C.

The steps α) and β) of the process (G) according to the invention are preferably carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). O-Chlorobenzoyl chloride or methyl ester, are employed in excess.

The reactions of the processes according to the invention can be carried out at atmospheric pressure or at elevated pressure; preference is given to working at atmospheric pressure. Work-up is carried out by customary methods of organic chemistry. The end products are preferably purified by crystallization, chromatographic purification or by removing the volatile components, if appropriate under reduced pressure.

The active compounds are suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculate.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, Melanoplus differentialis and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus* corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria melloenella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus sunnamensis,* Anthonomus spp., Sitophilus spp., *Otiorrhynchus sulcatus, Cosmopolites sordidus, Ceuthorrhynchus assimilis, Hypera postica,* Dermestes spp Trogoderna spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderrna spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Omithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., Trichodorus spp.

The active compounds of the formula (I) according to the invention in particular have outstanding activity against mustard beetle larvae (*Phaedon cochleariae*), caterpillars of the owlet moth (*Spodoptera frugiperda*), larvae of the green rice leaf hopper (*Nephotettix cincticeps*), green peach aphids (*Myzus persicae*) and all stages of the common spider mite (*Tetranychus urticae*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example and preferably by mixing the active compounds with extenders, that is liquid solvents and/or solid carriers, if appropriate with the use of surface-active aagents, that is emulsifying agents and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products;

suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulatin substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:
   2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxy-phenyl)-acetamide; 8-hydroxyquinoline sulphate; methyl (E)-2-{2-[6-(2-cyano-phenoxy)-pyrimidin4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole,
   benalaxyl, benodanil, benomyl, binapacryl, biphenyl, bitertanol, blasticidin-S, bromuconazole, bupirimate, buthiobate,
   calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
   dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon,
   edifenphos, epoxyconazole, ethirimol, etridiazole,
   fenarimol, fenbuconazole, fenfuram, fenitropan, fenpiclonil, fenpropidin, fenpropimorph, fentin acetate, fentin hydroxide, ferbam, fenimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox,
   guazatine,
   hexachlorobenzene, hexaconazole, hymexazol,
   imazalil, imibenconazole, iminoctadine, iprobenfos (EBP), iprodione, isoprothiolane,
   kasugamycin, copper preparations such as: copper hydroxide, copper naphthenate, copper oxychloride, copper sulphate, copper oxide, oxine-copper and Bordeaux mixture,
   mancopper, mancozeb, maneb, mepanipyrim, mepronil, metalaxyl, metconazole, methasulfocarb, methfuroxam, metiram, metsulfovax, myclobutanil,
   nickel dimethyldithiocarbamate, nitrothal-isopropyl, nuarimol,
   ofurace, oxadixyl, oxamocarb, oxycarboxin,
   pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon,
   quintozene (PCNB),
   sulphur and sulphur preparations,
   tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole,
   validamycin A, vinclozolin,
   zineb, ziram.

Bactericides:
   bronopol, dichlorophen, nitrapyrin, nickel dimethyldithiocarbamate, kasuamycin, octhilinone, furancarboxylic acid, oxytetracycline, probenazole, streptomycin, tecloftalam, copper sulphate and other copper preparations.

Insecticides/Acaricides/Nematicides:
   abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, beta-cyluthrin, bifenthrin, BPMC, brofenprox, bromophos A, bufencarb, buprofezin, butocarboxim, butylpyridaben,
   cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
   deltamethrin, demeton M, demeton S, demeton-S-methyl, diafenthiuron, diazinon, dichlofenthion, dichlorvos, dicliphos, dicrotophos, diethion, diflubenzuron, dimethoate, dinmethylvinphos, dioxathion, disulfoton,
   edifenphos, emamectin, esfenvalerate, ethiofencarb, ethion, ethofenprox, ethoprophos, etrimfos,
   fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythnrnate, flufenoxuron, flufenprox, fluvalinate, fonofos, formothion, fosthiazate, fubfenprox, furathiocarb,
   HCH, heptenophos, hexaflumuron, hexythiazox,
   imidaclopnid, iprobenfos, isazofos, isofenphos, isoprocarb, isoxathion, ivermectin,
   lamda-cyhalothrin, lufenuron,
   malathion, mecarbam, mevinphos, mesulfenphos, metaldehyde, methacrifos, methamidophos, methidathion, methiocarb, methomyl, metolcarb, milbemectin, monocrotophos, moxidectin,
   naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyradaphenthion, pyresmethrin, pyrethrum, pyridaben, pyrimidifen, pyriproxifen, quinalphos,

RH 5992, salithion, sebufos, silafluofen, sulfotep, suiprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thurinciensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex. spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres. spp., Knemidocoptes spp., Cytodites spp. and Laminosioptes spp.

For example, they have an outstanding activity against all larval stages of the fly *Lucilia cuprina* and all development stages of the tick *Amblyomma variegatum*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of preferred examples but without any limitation:

Beetles, such as *Hylotrupes bajulus, Chlorophorus pilosis, Anobium punctatum, Xestobium rufovillosum, Ptili-* nus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec. and Dinoderus minutus.

Dermapterans, such as Sirex juvencus, Urocerus gigas, Urocerus gigas taignus and Urocerus augur.

Termites, such as Kalotermnes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis and Coptotermes formosanus.

Bristletails, such as Lepisma saccharina.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic polar organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the, active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example I-54

At 25° C., 0.5 g of furan was initially charged in 25 ml of THF and admixed with 5 ml of 1.6N butyllithium solution in n-hexane. The mixture was stirred at this temperature for ½ hour, and a solution of 2.0 g of N-tbutoxycarbonyl-γ-4'-trifluoromethoxybiphenyl-4-yl-γ-butyrolactam (VIII-2) in 5 ml of THF was then added dropwise at −30° C. over a period of 15 minutes. The mixture was then stirred initially at −20° C. for 2 hours and then at room temperature overnight. The mixture was then diluted with water and extracted three times with methylene chloride. The combined organic phases were washed with saturated sodium chloride solution and dried over magnesium sulphate. Evaporation gave 2.0 g (86% of theory) of N-tert-butoxy-carbonyl-protected aminoketone (II-54) as a beige solid of melting point 74° C.

10 ml of trifluoroacetic acid were initially charged and cooled to 5° C. abgekühlt. Over a period of 10 minutes, 1.7 g of the above protected aminoketone were added, and the mixture was then stirred at room temperature overnight. The mixture was evaporated and the residue that remained was made alkaline using aqueous potassium carbonate and extracted repeatedly with dichloromethane. The combined organic phases were washed with saturated sodium chloride solution and dried over magnesium sulphate. Evaporation gave 1.1 g (86% of theor of 2-(2-furyl)-5-(4'-trifluoromethoxybiphen-4-yl)-3,4-dihydro-2H-pyrrole.

$^1$H-NMR (300 MHz, d$_6$-DMSO) [ppm]: 1.77 (m, 1H); 2.53 (m, 1H); 2.87–3.12 (m, 2H); 5.26 (t, 1H); 6.66–6.68 (dd, 1H); 7.06–7.07 (d, 1H); 7.37–7.80 (m, 8H); 7.89 (d, 1H).

The following compounds were obtained by analogous methods:

Example I-289

The starting material used was 2-bromo-3-methylpyridine.

MW: 396.41

M.p.: 53–54° C.

Example I-336

The starting material used was 2-bromo-3-trifluoromethyl-pyridine.

log P (pH2.3)=5.06

Example I-477

The starting material used was 2-fluoro-pyridine.

M.p. 81–83° C.

Example I-774

The starting material used was 2-bromo-pyridine.

M.p. 102–104° C.

Example I-821

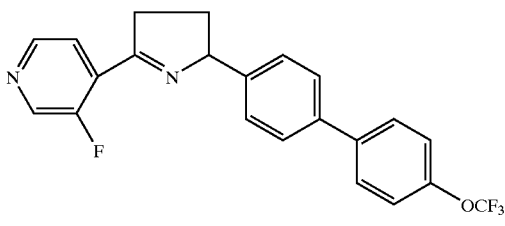

The starting material used was 3-fluoro-pyridine.
M.p. 87–89° C.

Example I-727

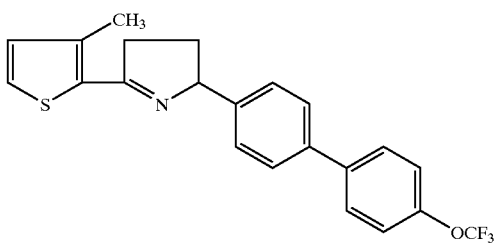

The starting material used was 3-methylthiophene.
M.p. 110° C.

Example I-383

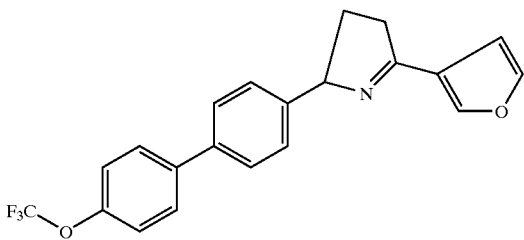

Here, 3-bromo-furan was used as starting material.
$^1$H-NMR (300 MHz, $d_6$-DMSO) [ppm]: 1.76 (m, 1H); 2.50 (m, 1H); 2.80–3.11 (m, 2H); 5.20 (t, 1H); 6.85–6.86 (d, 1H); 7.36–7.80 (m, 8H and 1-furyl-H); 8.24 (s, 1H).

Example I-524

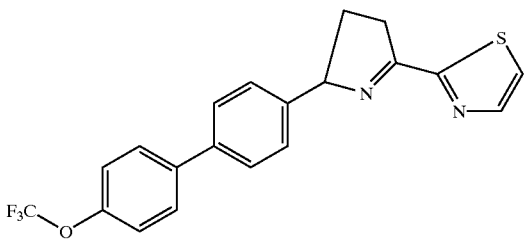

Here, 2-bromo-thiazole was used as starting material.
$^1$H-NMR (300 MHz, $d_6$-DMSO) [ppm]: 1.89 (m, 1H); 2.61 (m, 1H); 3.13 (m, 1H); 3.35 (m, 1H); 5.36 (t, 1H); 7.40–7.80 (m, 8H); 7.96–7.97 (d, 1H); 8.04–8.05 (d, 1H).

Example I-706

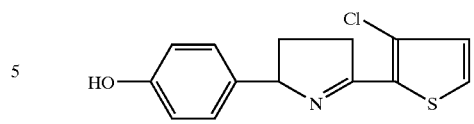

2-(5-(4-Hydroxyphenyl)-$\Delta^2$-pyrrolin-2-yl)-3-chlorothiophene

At 0° C., 60 g of crude 4-(4-tert-butyloxycarbonyloxyphenyl)-4-tert-butyloxycarbonylamino-1-(3-chlorothiophen-2-yl)-butan-1-one (II-706) in 100 ml of methylene chloride were admixed with 90 ml of trifluoroacetic acid and the mixture was stirred at 20° C. overnight. The mixture was diluted with water, neutralized with sodium hydrogen carbonate and extracted with methylene chloride. The solvent is removed, and the brown resin is then stirred with diisopropyl ether and filtered off with suction. This gives 24.8 g (yield 89.5% of theory) of 2-(5-(4-hydroxyphenyl)-$\Delta^2$-pyrrolin-2-yl)-3-chlorothiophene of m.p. 146°.

Example I-708

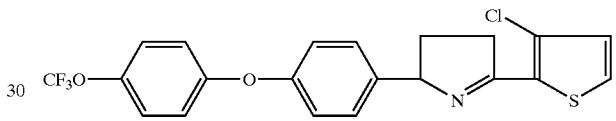

2-(5-(4-Trifluoromethoxyphenoxy-phenyl)-$\Delta^2$-pyrrolin-2-yl)-3-chlorothiophene At room temperature, 1.4 g of the compound I-706 are stirred with 1.5 g (7.5 mmol) of 4-trifluoromethoxyphenylboronic acid and 0.9 g (5 mmol) of copper acetate and 4 g of powdered molecular sieve (4 Å) in 20 ml of methylene chloride with 2.5 g (25 mmol) of triethylamine overnight. The mixture is filtered, the filtrate is concentrated and the residue is purified by column chromatography.

This gives 0.8 g (yield 35.5% of theory) of 2-(5-(4-Trifluoromethoxyphenoxy)-$\Delta^2$-pyrrolin-2-yl)-3-chlorothiophene as a brown resin of log p (pH 2.3): 4.50.

Example I-718

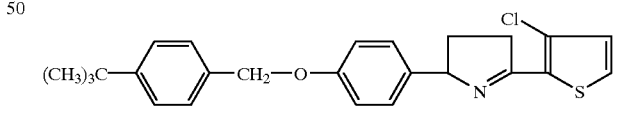

3-Chloro-2-[5-(4-(4-tert-butylbenzyloxy)-phenyl)-$\Delta^2$-pyrrolin-2-yl]-thiophene 0.9 g (5 mmol) of 4-tert-butyl-benzyl chloride are added to a mixture of 1.4 g (5 mmol) of the compound I-706 and 2.1 g (15 mmol) of potassium carbonate in 30 ml of acetonitrile, and the mixture is stirred at room temperature overnight. Water is then added, and the product is extracted with ethyl acetate. The solvent is removed under reduced pressure and the crude product that remains is purified by column chromatography and then recrystallized from n-pentane. This gives 1.0 g of 3-chloro-2-[5-(4-(4-tertbutylbenzyloxy)-phenyl)-Δ²-pyrrolin-2-yl]-thiophene of m.p. 102° in a yield of 47.2% of theory.
Analogously to the procedures for preparing Examples I-708 and I-718, it is possible to obtain the following examples:
Example I-707
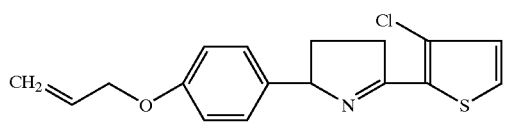
log P$_{(acidic)}$:2.29
Example I-709
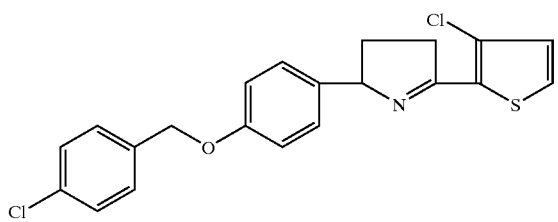
M.p. 134° C.
Example I-710
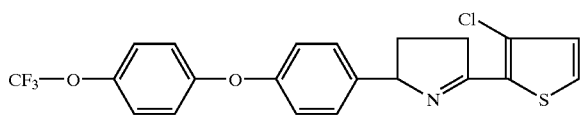
log P$_{(acidic)}$: 4.50
Example I-711
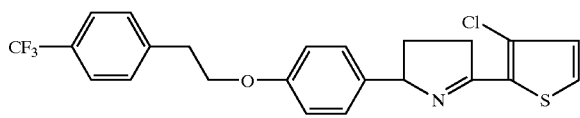
M.p. 86° C.
Example I-712
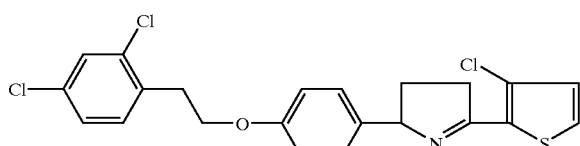
M.p. 76° C.
Example I-713
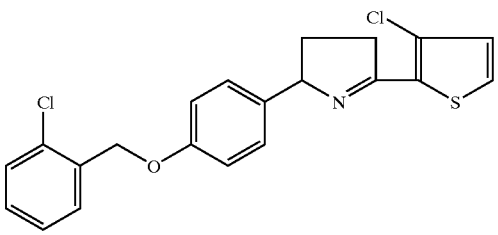
M.p. 84° C.
Example I-714
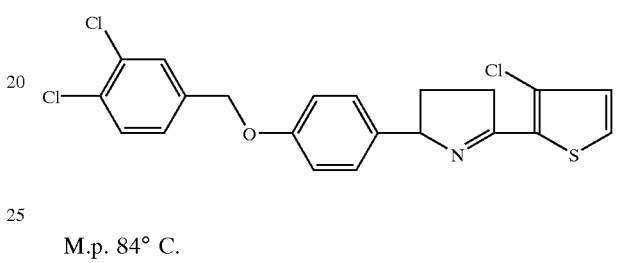
M.p. 84° C.
Example I-715
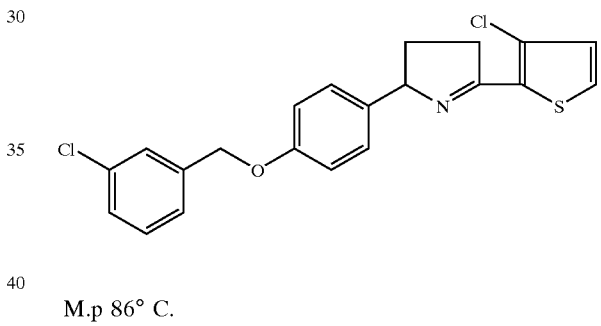
M.p 86° C.
Example I-716
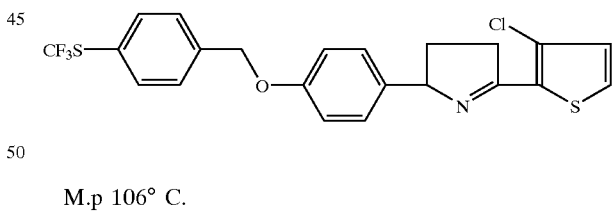
M.p 106° C.
Example I-717
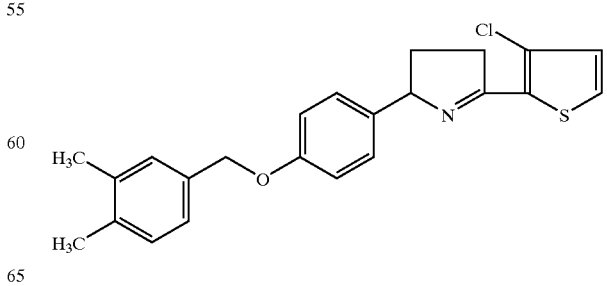
M.p. 104° C.

Example I-720 log $P_{(acidic)}$: 1.97

Example I-571

Here, only 2-bromo-5-methylfuran was used as starting material.

$^1$H-NMR (300MHz, $d_6$-DMSO) [ppm]: 1.75 (m, 1H); 2.35 (s, 3H); 2.50 (m, 1H); 2.81–3.10 (m, 2H); 5.22 (t, 1H); 6.28 (d, 1H), 6.93 (d, 1H); 7.33–7.80 (m, 8H).

In the examples below, the intermediate II was not isolated but cyclized in situ:

Example I-3

3.3 g (9.1 mmol) of 1-(tert-butyloxycarbonylamino)-1-(4-fluorophenyl)-4-thienylbutan4-one are dissolved in 30 ml of methylene chloride and, with ice-cooling, admixed with 9 ml of trifluoroacetic acid. After 5 hours, the reaction mixture is washed with NaHCO$_3$ solution until neutral, and the organic phase is separated off and concentrated under reduced pressure. The residue of altogether 2.0 g is purified on silica gel using the system cyclohexane/ethyl acetate (2:1). This gives 1.5 g (yield: 67.3% of theory) of 2-(2-thienyl)-5-(4-fluorophenyl)-3,4-dihydro-2H-pyrrole as an oil;

log$_p$ (pH=2.3): 1.04

Example I-7

Here, the starting material used was 2-bromo-thiophene.

M.p. 128° C.

log$_p$ (pH=2.3): 2.45

Example I-148

Here the starting material used was 2-bromo-5-chloro-thiophene.

M.p. 144° C.

log$_p$ (pH=2.3): 4.21

Example I-195

Here the starting material used was 2-bromo-3-chloro-thiophene.

M.p. 99° C.

log$_p$ (pH=2.3): 4.67

Example I-430

Here the starting material used was 3-bromo-thiophene.

M.p. 116° C.

log$_p$ (pH=2.3): 2.44

Example I-618

Here the starting material used was 2-bromo-5-bromo-thiophene.

M.p. 100° C.

log$_p$ (pH=2.3): 4.73

Example I-678

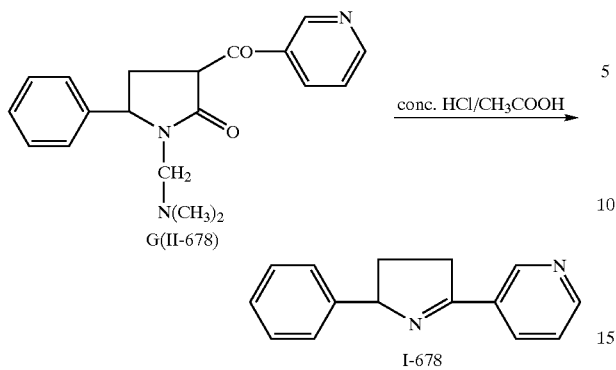

5.6 g (17.3 mmol) of 1-dimethylaminomethyl-5-phenyl-3-pyridoyl-pyrrolidin-2-one are refluxed for 5 hours in your mixture of 60 ml of conc. hydrochloric acid and 30 ml of glacial acetic acid. The reaction mixture is allowed to stand overnight and then adjusted to pH 10 using conc. aqueous sodium hydroxide solution with ice-cooling, and is extracted with methylene chloride. The organic phase is evaporated and the oily residue (1.5 g) is purified by silica gel chromatography using the system ethyl acetate. This gives 0.18 g (yield: 4.7% of theory) of 2-(3-pyridyl)-5-(phenyl)-3,4-dihydro-2H-pyrrolene as a resinous product of $\log_p$ (pH=7.5): 2.01.

Example I-868

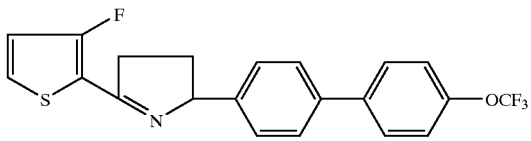

Boc-protected aminoketone (II-868) (3.80 g, 7.3 mmol) was initially charged in $CH_2Cl_2$ (10 ml). At 0° C., trifluoroacetic acid (8.37 g, 73 mmol) was added, and the mixture was then stirred at room temperature for 3 hours. The solution was concentrated under reduced pressure and the residue was adjusted to pH 14 using 1 N NaOH, and then extracted with ethyl acetate. The organic phase was dried over $MgSO_4$, filtered and concentrated. This gave a crude yield of 3.12 g (100% of theory). 1.50 g of this crude material, were purified by column chromatography (mobile phase cyclohexane:ethyl acetate). This gave 0.27 g of pure 5-(3-fluorothien-2-yl)-3,4-dihydro-2-[4'-trifluoromethoxy]-[1,1'-biphenyl]-4-yl-2H-pyrrole (= yield of 19% of theory).

HPLC: 95.4%.

log P (pH 2.3)=3.18

LC-MS: $M^+ + M = 406$

Preparation of the starting materials

Example II-3

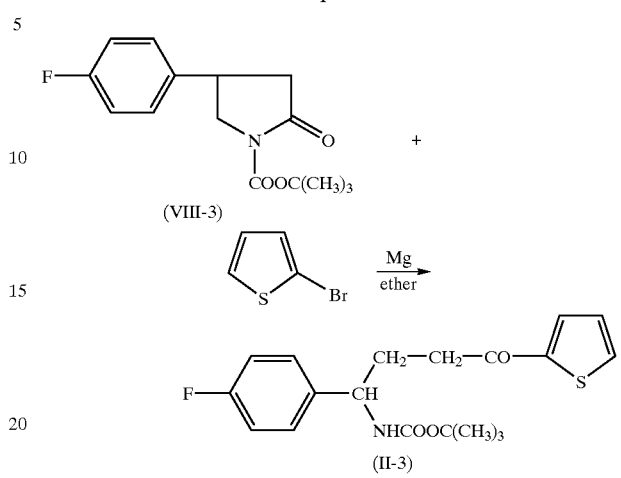

3.6 g (22 mmol) of 2-bromothiophene are added dropwise to 0.6 g (23 mg atom) of magnesium, covered with a layer of 60 ml of diethyl ether, and the mixture is then boiled at reflux for 30 min. With stirring at -50° C., a solution of 5 g (18 mmol) of 1-(tert-butyloxycarbonyl)-5-(4-fluorophenyl)-pyrrolidone-2, dissolved in 80 ml of abs. diethyl ether, is added dropwise to this Grignard solution. The temperature is allowed to rise to 25° C., and the mixture is stirred overnight. With stirring, a concentrated $NH_4Cl$ solution is then added dropwise, and the org. phase is separated off and concentrated using a rotary evaporator. The cooled oil is stirred with n-pentane, resulting in the crystallization of 3.4 g (yield 52% of theory) of 1-(tert-butyloxycarbonyl)-1-(4-fluorophenyl)-4-(2-thienyl)-butan-4-one.

M.p. 110–120°.

Example II-54

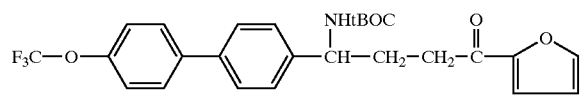

At 25° C., 0.5 g of furan was initially charged in 25 ml of THF and admixed with 5 ml of 1.6N butyllithium solution in n-hexane. The mixture was stirred at this temperature for ½ hour, and a solution of 2.0 g of N-$^t$butoxycarbonyl-γ-4'-trifluoromethoxybiphenyl-4-yl-γ-butyrolactam (VIII-2) in 5 ml of THF was then added dropwise at -30° C. over a period of 15 minutes. The mixture was then stirred initially at -20° C. for 2 hours and then at room temperature overnight. The mixture was then diluted with water and extracted three times with methylene chloride. The combined organic phases were washed with saturated sodium chloride solution and dried over magnesium sulphate. Evaporation gave 2.0 g (86% of theory) of N-tert-butoxy-carbonyl-protected aminoketone (II-54) as a beige solid of melting point 74° C.

The following compounds were obtained analogously to II-54:

Example II-571

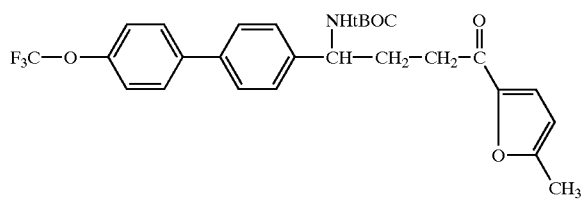

M.p.: 71° C.

Example II-383

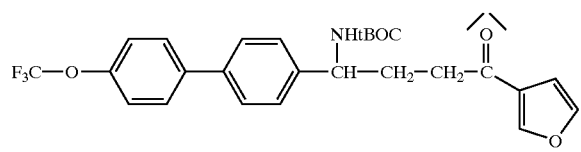

M.p.: 67° C.

Example II-524

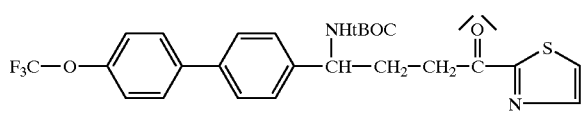

M.p.: 117° C.

Example II-706

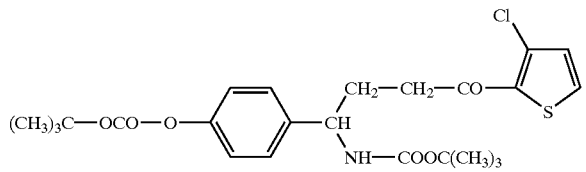

4-(4-(tert-Butyloxycarbonyloxyphenyl)-4-tert-butyloxycarbonylamino-1-(3-chlorothiophenyl-2)-butan-1-one At −70° C., with stirring and under an atmosphere of argon, 142 ml (0.23 mol) of a 1.6 molaren [lacuna] butyllithium . . . (n-hexane) are added dropwise to a solution of 23.8 g (0.2 mol) of 3-chlorothiophene in 150 ml of diethyl ether. After 5 min, 37.8 g (0.1 mol) of 1-tert-butyloxycarbonyl-5-(4-tert.-butyloxycarbonyloxyphenyl)pyrrolidone-(2), dissolved in 300 ml of ether, are then added at −70° C. The reaction mixture is stirred at −70° C. for 2 h and then allowed to stand at room temperature overnight. 10% strength ammonium chloride solution is then added, and the product is extracted with ethyl acetate. The organic phase is washed with water and the solvent is then removed under reduced pressure. This gives 60.8 g of an oily, 4-(4-(tert-butyloxycarbonyloxyphenyl)-4-tert-butyloxycarbonylamino-1-(3-chlorothiophenyl-2)-butan-1-one-containing crude product which is directly reacted further as such.

Example II-868

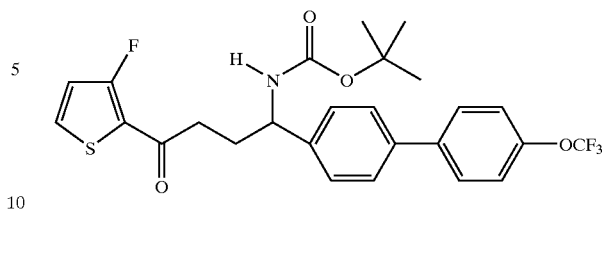

3-Fluorothiophene (1.66 g) was initially charged in THF (20 ml). "Bule (1.6 M, 7.3 δml) was added dropwise at −78° C. After 30 min, compound VIII-2 in TMF (5 ml) was added dropwise, and the mixture was then stirred at room temperature overnight. The mixture was then diluted with water (100 ml) and extracted with ethyl acetate. The organic phase was dried over MgSO₄, filtered and concentrated. A crude yield of 3.82 g was isolated.

HPLC: 58.3% log P (pH 2.3)=5.05

The crude product was reacted further without purification.

Example VII-3

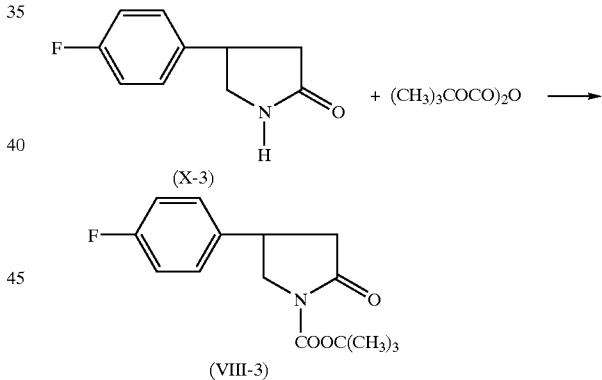

1-(tert-Butyloxycarbonyl)-5-(4-fluorophenyl)-pyrrolidin-2-one 22.6 g (0.126 mol) of 5-(4-fluorophenyl)-pyrrolidin-2-one in 200 ml of toluene are boiled at reflux with 55 g (0.25 mol) of tert-butyl pyrocarbonate for 5 hours. After cooling the mixture, is washed repeatedly with water and the organic phase, is dried and concentrated under reduced pressure using a rotary evaporator. The residue is stirred with petroleum ether and the crystals are filtered off with suction. This gives 21.8 g (62% yield of theory) of 1-(tert-butyloxycarbonyl)-5-(4-fluorophenyl)-pyrrolidin-2-one of m.p. 117°.

Example VIII-1

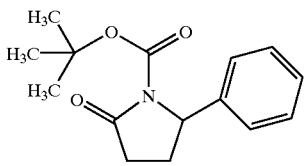

3.4 g of γ-phenyl-γ-butyrolactam (for example from Ex. X-1) were initially charged in 63 ml of tetrahydrofuran (THF) and, at −78° C., admixed with 9.24 ml of 2.4N butyllithium solution in n-hexane. The mixture was stirred at this temperature for half an hour, and a solution of 5.04 g of di-tert-butyl dicarbonate in 20 ml of THF was then added dropwise with further cooling, and the mixture was stirred at −78° C. for another 3 hours and then without cooling overnight. The mixture was then hydrolysed using saturated aqueous ammonium chloride solution, diluted with water and extracted three times with ethyl acetate. The combined organic phases were washed with saturated sodium chloride solution and dried over magnesium sulphate. Evaporation gave 1.54 g (28% of theory) of N-$^t$butoxycarbonyl-γ-phenyl-γ-butyrolactam.

$^1$H-NMR (400MHz, d$_6$-DMSO) [ppm]: 1.18 (s, 9H); 1.73 (m, 1H); 2.402–260 (m, 3H); 5.10 (m, 1H), 7.24 (m, 2H); 7.30 (m, 1H); 7.38 (m, 2H)

Example VIII-2

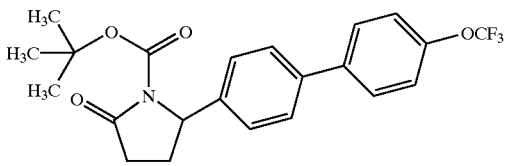

1.7 g of γ-4'-trifluoromethoxybiphenyl-4-yl-γ-butyrolactam (for example from Ex. X-a-2) were initially charged in 30 ml of tetrahydrofuran (THF) and, at −78° C., admixed with 2.42 ml of 2.4N butyllithium solution in n-hexane. The mixture was stirred at this temperature for half an hour, and a solution of 1.27 g of di-tert-butyl dicarbonate in 10 ml of THF was then added dropwise with further cooling. Cooling is then removed and the mixture is stirred at room temperature overnight. The mixture was then hydrolysed using saturated aqueous ammonium chloride solution, acidified with 2N hydrochloric acid and extracted three times with dichloromethane. The mixture was dried and evaporated and the product was then purified by column chromatography (stationary phase: silica gel; mobile phase gradient cyclohexane:ethyl acetate=5:1.3 to 1.1:1). This gave 1.14 g (47%. of theory) of partially crystallined N-$^t$butoxycarbonyl-γ-4'-trifluoromethoxybiphenyl-4-yl-γ-butyrolactam.

$^1$H-NMR (400 MHz, CDCl$_3$) [ppm]: 1.22 (s, 9H); 1.79 (m, 1H); 2.48–2.60 (m, 3H); 5.17 (m, 1H); 7.36 (d, 2H); 7.46 (d, 2H); 7.71 (d, 2H); 7.80 (d, 2H)

Example VIII-8

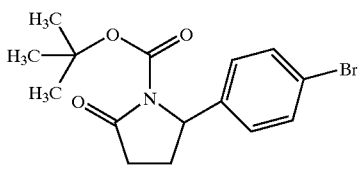

At −78° C., 3.24 ml of diisopropylamine were initially charged in 90 ml of THF and admixed with 9.24 ml of 2.4N butyllithium solution in n-hexane. The mixture was stirred at this temperature for ½ hour, and a solution of 5.02 g of γ-4-bromophenyl-γ-butyrolactam (for example from Example XI-3) in 20 ml of THF was then added dropwise. The mixture was stirred at −78° C. for another ½ hour, 5.04 g of di-tert-butyldicarbonate in 20 ml of THF were then added dropwise, and the mixture was allowed to thaw and stirred at room temperature overnight. The mixture was then hydrolysed using saturated aqueous ammonium chloride solution, acidified with 2N hydrochloric acid and extracted three times with 150 ml of dichloromethane. The mixture was dried over magnesium sulphate and evaporated, and the product was then purified by crystallization from dichloromethane/hexane. This gave a total of 7.61 g (97% of theory) of crystalline N$^t$butoxycarbonyl-γ-4-bromophenyl-γ-butyrolactam. The crystal fraction of the highest purity (2.34 g) had a melting point of 122–124° C.

Example VIII-706

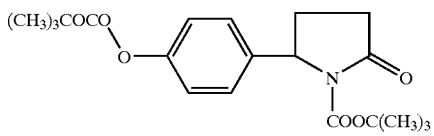

17.7 g (0.1 mol) of compound X2 (a), dissolved in 150 ml of dimethylformamide, are admixed with 1.5 g of 4-dimethylaminopyridine and then with 93.4 g (0.43 mol) of di-tert-butyl dicarbonate, and the mixture is stirred at room temperature for 5 hours. The mixture is then diluted with water and the precipitate is filtered off with suction, washed with water and dried under reduced pressure. This gives 35 g (yield 92.7% of theory) of 5-(4-tert-butyloxycarbonyloxyphenyl)-1-tert-butyloxycarbonylpyrrolidone-(2) of m.p. 168° C.

Example X-1

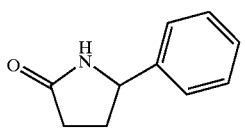

At 0° C., 6.45 g of γ-ethoxy-γ-butyrolactam and 50 ml of conc. sulphuric acid were initially charged and 18.8 ml of benzene were added. After thawing, the mixture was stirred at room temperature for 4 days. For work-up, the mixture was poured onto ice and extracted three times with ethyl acetate, and the combined extracts were washed once each with water and saturated sodium chloride solution, dried and concentrated. This gave 8.1 g (100% of theory) of γ-phenyl-γ-butyrolactam.

¹H-NMR (400 MHz, d₆-DMSO) [ppm]: 1.75 (m, 1H); 2.23 (t, 2H); 2.45 (m, 1H); 4.67 (t, 1H); 7.26–7.39 (m, 5H); 8.08 (br, 1H)

Example X-2

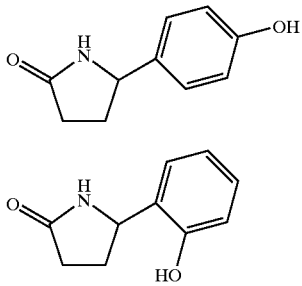

(X-2a)

(X-2b)

12.9 g of γ-ethoxy-γ-butyrolactam, 10 ml of conc. sulphuric acid and 90 ml of glacial acetic acid were initially charged at 0° C. and admixed a little at a time with a total of 18.8 g of phenol. After thawing, the mixture was stirred at room temperature for 2 days. For work-up, the mixture was poured onto ice and extracted three times with ethyl acetate, and the combined extracts were washed once each with water and saturated sodium chloride solution, dried and evaporated. After some time, γ-2-hydroxyphenyl-γ-butyrolactam (X-2b) of melting point 220° C. (6.4 g 36% of theory) crystallized form the aqueous phase. The evaporation residue was stirred with a 1:1 mixture of cyclohexane/ethyl acetate and gave, after filtration with suction, 4.65 g of γ4-hydroxyphenyl-γ-butyrolactam (X-2a) of melting point 183° C. The filtrate was concentrated. Recrystallization from dichloromethane/hexane gave a further 3.35 g (total: 45% of theory) of γ-4-hydroxyphenyl-γ-butyrolactam.

Example X-3

The 5-(4-fluorophenyl)-pyrrolidone-2 (X-3) is obtained by catalytic reductive amination of 4-fluorophenyl-4-oxo-butyric acid (J. Med. Chem. 27 1099 (1984) analogously to the procedure of Rappe et. al. Liebigs Ann. Chem. 596, p. 221 (1955), as described for 5-phenylpyrrolidone-2.

Example X-8

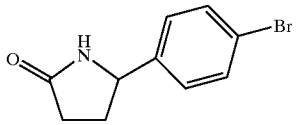

199.3 g of ammonium formate in 127.9 g of formic acid were initially charged in a 3l three-necked flask fitted with stirrer and distillation bridge, and 210 g of 4-brombenzoylpropionic acid, which had been recrystallized from toluene, were added. The flask was then immersed into an oilbath of a temperature of 200° C. At 60° C., the contents of the flask begin to dissolve, with evolution of gas. The mixture is distilled for about 2 h, the bottom temperature increasing from 140 to 167° C. After cooling, to below 60° C., 1 l of dichloromethane was added carefully and precipitated salt was removed by filtration with suction through a nutsch filter. The organic phase was washed with 1 l of water, dried over magnesium sulphate and concentrated under reduced pressure. For purification, the crude product was filtered through 1 kg of silica gel using dichoromethane/ethanol/triethylamine (95:5:3) and then crystallized from methyl tert-butyl ether. This gave 38 g, (19.% of theory) of γ-4-bromopheny)-γ-butyrolactam of melting point 142° C.

Example X-a-2

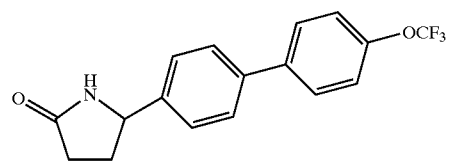

Under argon, 5.4 g of γ-4-trifluoromethylsulphonyloxyphenyl-γ-butyrolactam (for example from Ex. XVI-2) were initially charged in 43 ml of dimethoxyethane. 5.87 a of 4-trifluoromethoxyboronic acid and 1.01 g of tetrakis(triphenylphosphine)palladium were added successively. After 15 minutes, 28 ml of 2M of sodium carbonate solution were added and the mixture was heated at 80° C. and stirred overnight. After the reaction has ended, the mixture was taken up in water/ethyl acetate, the phases were separated and the aqueous phase was extracted twice with ethyl acetate. The combined organic phases were washed with saturated sodium chloride solution and dried. Evaporation gave 5.5 (98% of theory) of γ-4'-trifluoromethoxybiphenyl4-yl-γ-butyrolactam of melting point 128° C.

Example XVI-2

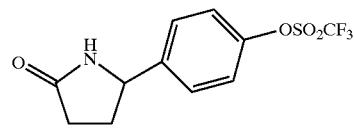

At 0° C., 10 g of trifluoromethanesulphonic anhydride were added dropwise to 5.23 g of γ-4-hydroxyphenyl-γ-butyrolactam (for example from Ex. X-2) in 60 ml of pyridine. The mixture was stirred at room temperature overnight and then poured, onto ice, acidified with 10% strength hydrochloric acid and extracted three times with ethyl acetate. Drying and evaporation of the solvent gave 6.4 g (70% of theory) of γ-4-trifluoromethylsulphonyloxyphenyl-γ-butyrolactam of melting point 127° C.

Example G (I'-678)

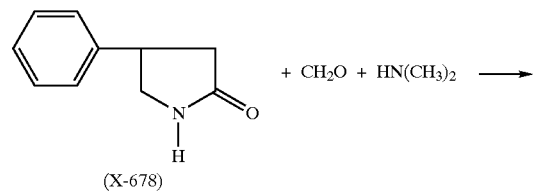

-continued

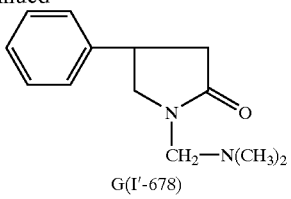
G(I'-678)

At 20° C., 20 g (0.25 mol) of aqueous formaldehyde solution (35% strength) and 29.3 g (0.25 mol) of 40% strength aqueous dimethylamine solution are added dropwise to a solution of 10 g (62 mmol) of 5-phenylpyrrolidin-2-one in 180 ml of isopropanol, and the mixture is stirred for 70 sec. Under reduced pressure, the solvent is removed using a rotary evaporator, and the residue is taken up in diisopropyl ether and, after drying over $MgSO_4$, concentrated under reduced pressure. This gives 8.7 g (64.4% yield of theory) of 1-dimethylamino-5-phenylpyrrolidone-2 as a colourless oil. Log p (pH 7.5)=1.52.

The preparation of the starting material (X-678) 5-phenylpyrrolidin-2-one is described in: Rappe et. al., Liebigs Ann. Chem. 596, p. 221 (1955).

Example G (II'-678)

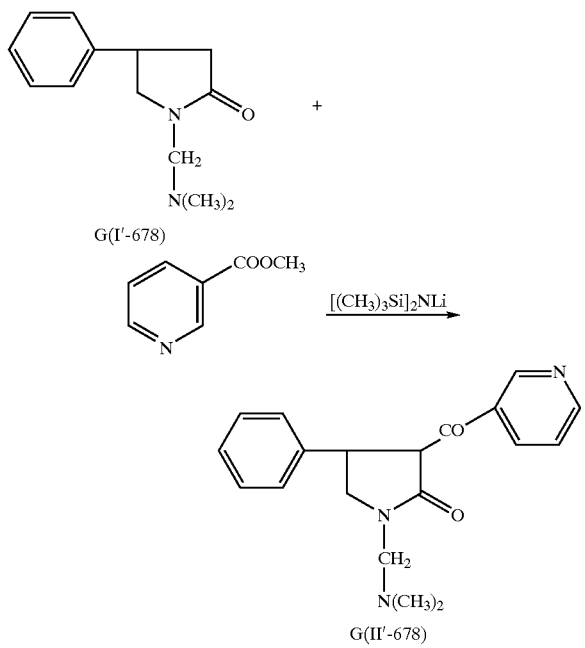

At −25°, a solution of 4.6 g (21 mmol) of 1-dimethylaminomethyl-5-phenylpyrrolidin-2-one, dissolved in 10 ml of absolute THF, is added dropwise to 43 ml of a 1-molar THF solution of lithium bis(trimethylsilyl) amide. The mixture is stirred at −25° C. for 30 min, after which 3 g (22 mmol) of methyl 3-pyridinecarboxylate, dissolved in 25 ml of tert-butyl methyl ester, are added, and the mixture is allowed to warm to room temperature. The mixture is stirred overnight and then carefully hydrolysed with water, the produced is extracted with dichloromethane and the org. phase is concentrated under reduced pressure. This gives 5.6 g of 1-dimethylaminomethyl-5-phenyl-3-pyridoyl-pyrrolidone-2 as a viscous oil which is reacted further without further purification.

Use Examples

Example A

Tetranychus test (OP-resistant/dip treatment)
  Solvent: 7 parts by weight of dimethylformamide
  Emulsifier: 1 part by weight of alkylaryl polyglycol ether
  To produce a suitable preparation of active compound, 1 part by weight of active compound is mixed with the stated amounts of solvent and the stated amount of emulsifier, and the concentrate is diluted with emulsifier-containing water to the desired concentration.
  Bean plants (*Phaseolus vulgaris*) which are heavily infested by all development stages of the greenhouse red spider mite Tetranychus urticae are dipped into a preparation of active compound of the desired concentration.
  After the desired period of time, the effect in % is determined. 100% means that all spider mites have been killed; 0% means that none of the spider mites has been killed.
  In this test, for example, the compounds of Preparation Examples I-7 and I-148 effected, at an exemplary active compound concentration of 0.1%, a kill of at least 95% after 7 days.

Example B

*Spodoptera frugiperda* test
  Solvent: 7 parts by weight of dimethylformamide
  Emulsifier: 1 part by weight of alkylaryl polyglycol ether
  To produce a suitable preparation of active compound, 1 part by weight of active compound is mixed with the stated :amounts of solvent and emulsifier, and the concentrate is diluted with emulsifier-containing water to the desired concentration.
  Cabbage leaves (*Brassica oleracea*) are treated by being dipped into the preparation of active compound of the desired concentration and are populated with caterpillars of the armyworm (*Spodoptera frugiperda*) while the leaves are still moist.
  After the desired period of time, the kill in % is determined. 100% means that all caterpillars have been killed; 0% means that none of the caterpillars has been killed.
  In this test, for example, the compounds of Preparation Examples I-774, I-336, I-477, I-289, I-821 and I-195 exhibit, at an exemplary active compound concentration of 0.1%, a kill of at least 85% after 7 days.

Example C

Tetranychus test
  Solvent: 7 parts by weight of dimethylformamide
  Emulsifier: 1 part by weight of alkylaryl polyglycol ether
  To produce a suitable preparation of active compound, 1 part by weight of active compound is mixed with the stated amounts of solvent and emulsifier, and the concentrate is diluted with emulsifier-containing water to the desired concentration.
  Bean plants (*Phaseolus vulgaris*) which are heavily infested by all stages of the greenhouse red spider mite (*Tetranychus urticae*) are dipped into a preparation of active compound of the desired concentration.
  After the desired period of time, the effect in % is determined. 100% means that all spider mites have been killed; 0% means none of the spider mites has been killed.
  In this test, for example, the compounds of the Preparation Examples I-383, I-289, I-618, I-195, I-727, I-708 and I-709 exhibit, at an exemplary active compound concentration of 0.1%, a kill of at least 90% after 7 days.

Example D

*Phaedon larvae* test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae has been killed.

In this test, for example, the compounds of Preparation Examples I-524, I-383, I-774, I477, I-289 and I-821 exhibit, at an exemplary active compound concentration of 0.1%, a kill of at least 98% after 7 days.

What is claimed is:

1. A 2-hetaryl-3,4dihydro-2H-pyrrole of the formula (I)

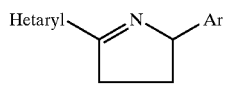

(I)

wherein

Hetaryl represents an unsaturated 6-membered heterocycle having one or more nitrogen atoms and which is unsubstituted or mono- or polysubstituted by radicals $H^1$, wherein $H^1$ represents hydrogen, halogen, cyano, formyl, nitro, alkyl, trialkylsilyl, alkoxy, halogenoalkyl, halogenoalkoxy, alkylcarbonyl, alkoxycarbonyl, pentafluorothio, carbamoyl, thiocarbamoyl, alkoximino or $S(O)_o R^3$, Ar represents the radical

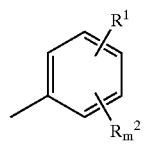

wherein m represents 0, 1, 2, 3 or 4, $R^1$ represents halogen or one of the groupings below
(l) —X—A
(m) —B—Z—D
(n) —Y—E $R^2$ represents hydrogen, halogen, cyano, nitro, alkyl, alkoxy, halogenoalkyl, halogenoalkoxy, alkoxyalkyl or —$S(O)_o R^3$, o represents 0, 1 or 2, $R^3$ represents alkyl or halogenoalkyl, X represents a direct bond, oxygen, sulphur, carbonyl, carbonyloxy, oxycarbonyl, alkylene, alkenylene, alkynylene, alkyleneoxy, oxyalkylene, thioalkylene, alkylenedioxy or dialkylsilylene, A represents phenyl, naphthyl or tetrahydronaphthyl, each of which is unsubstituted or mono- or polysubstituted by radicals $W^1$, or represents a 5- to 10-membered heterocyclyl containing one or two aromatic rings and having one or more heteroatoms selected from the group consisting of nitrogen, oxygen and sulphur and which is unsubstituted or mono- or polysubstituted by radicals $W^2$, B represents p-phenylene which is unsubstituted or mono- or disubstituted by radicals $W^1$, Z represents oxygen or sulphur, D represents hydrogen, alkyl, alkenyl, alkynyl, halogenoalkyl, halogenoalkenyl, unsubstituted or halogen-, alkyl-, alkenyl-, halogenoalkenyl-, phenyl-, styryl-, halogenophenyl- or halogenostyryl-substituted cycloalkyl or cycloalkylalkyl, represents unsubstituted or halogen- or alkyl-substituted cycloalkenyl or cycloalkenylalkyl, represents unsubstituted or nitro-, halogen-, alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms selected from the group consisting of nitrogen, oxygen and sulphur, represents —CO—$R^4$, —CO—$NR^5R^6$ or represents the grouping —$(CH_2)_p$—$(CR^7R^8)_q$—$(CH_2)_r$—G, Z and D also together represent unsubstituted or nitro, halogen-, alkyl-, alkoxy-, halogenoalkyl- or halogenoalkoxy-substituted phenoxyalkyl, Y represents a direct bond, oxygen, sulphur, carbonyl, carbonyloxy, oxycarbonyl, alkylene, alkenylene, alkynylene, alkyleneoxy, oxyalkylene, thioalkylene, alkylenedioxy or represents p-phenylene which is unsubstituted or mono or disubstituted by radicals $W^1$, E represents hydrogen, alkyl, alkenyl, alkynyl, halogenoalkyl, halogenoalkenyl, represents unsubstituted or halogen-, alkyl-, alkenyl-, halogenoalkenyl-, phenyl-, styryl-, halogenophenyl- or halogenostyryl-substituted cycloalkyl, represents unsubstituted or halogen- or alkyl-substituted cycloalkenyl, represents phenyl which is unsubstituted or mono- to tetrasubstituted by radicals $W^1$ or represents 5- to 6-membered hetaryl having one or two heteroatoms selected from the group consisting of nitrogen, oxygen and sulphur and which is unsubstituted or mono- to tetrasubstituted by radicals $W^2$ or represents the grouping —$(CH_2)_p$—$(CR^7R^8)_q$—$(CH_2)_r$—G, $R^4$ represents alkyl, alkoxy, alkenyl, alkenyloxy, represents unsubstituted or halogen-, alkyl-, alkenyl-, halogenoalkyl- or halogenoalkenyl-substituted cycloalkyl, cycloalkyloxy or cycloalkylalkyloxy or represents unsubstituted or nitro-, halogen-, alkyl-, alkoxy-, halogenoalkyl- or halogenoalkoxy-substituted phenyl or naphthyl, $R^5$ represents hydrogen or alkyl, $R^6$ represents alkyl, halogenoalkyl, unsubstituted or halogen-, alkyl-, alkenyl-, halogenoalkyl- or halogenoalkenyl-substituted cycloalkyl or cycloalkylalkyl or represents unsubstituted or halogen-, alkyl-, alkoxy-, halogenoalkyl- or halogenoalkoxy-substituted phenyl or phenylalkyl, p, q and r independently represent 0, 1, 2 or 3, such that the sum of p, q and r is less than 6, $R^7$ and $R^8$ independently represent hydrogen or alkyl, G represents cyano, represents an unsubstituted or halogen-, alkyl- or halogenoalkyl- and, at the point of linkage, unsubstituted or $R^9$-substituted 5- or 6-membered heterocycle having 1 to 3 heteroatoms selected from the group consisting of nitrogen, groupings:

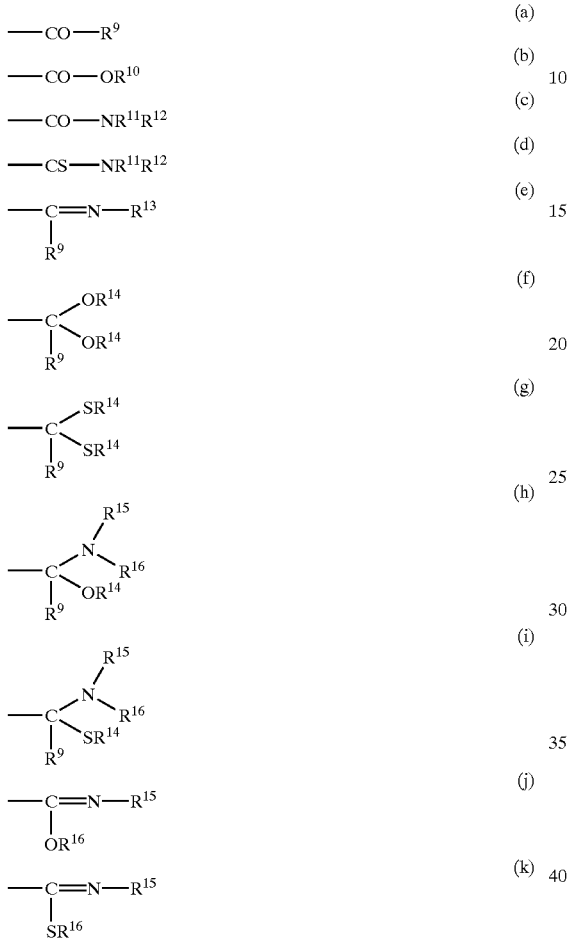

$R^9$ represents hydrogen, alkyl, alkenyl, halogenoalkyl, halogenoalkenyl, unsubstituted or halogen-, alkyl- or halogenoalkyl-substituted cycloalkyl or represents phenyl which is unsubstituted or mono- to pentasubstituted by alkylcarbonylamino, alkylcarbonylalkylamino and/or radicals $W^3$, $R^{10}$ represents hydrogen, alkyl, alkenyl, halogenoalkyl, halogenoalkenyl, unsubstituted or halogen-, alkyl- or halogenoalkyl-substituted cycloalkyl or cycloalkylalkyl or represents arylalkyl which is unsubstituted or mono- to pentasubstituted by radicals $W^3$, $R^{11}$ and $R^{12}$ independently represent hydrogen, alkyl, alkenyl, halogenoalkyl, halogenoalkenyl, alkoxy, unsubstituted or halogen-, alkyl- or halogenoalkyl-substituted cycloalkyl or cycloalkylalkyl, represent aryl or arylalkyl, each of which is unsubstituted or mono- to pentasubstituted by radicals $W^3$, or represent —$OR^{10}$ or —$NR^9R^{10}$ or together represent an alkylene chain having 2 to 6 members in which unsubstituted or one methylene group is replaced by oxygen, $R^{13}$ represents —$OR^{10}$, —$NR^9R^{10}$ or —$N(R^9)$—$COOR^{10}$, $R^{14}$, $R^{15}$ and $R^{16}$ independently represent alkyl, $W^1$ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio or —$S(O)_oR^3$, $W^2$ represents halogen, cyano, formyl, nitro, alkyl, trialkylsilyl, alkoxy, halogenoalkyl, halogenoalkoxy, alkylcarbonyl, alkoxycarbonyl, pentafluorothio, —$S(O)_oR^3$ or —$C(R^9)$=$N$—$R^{13}$, $W^3$ represents halogen, cyano, nitro, alkyl, alkoxy, halogenoalkyl, halogenoalkoxy, dialkylamino, —$S(O)_oR^3$, —$COOR^{17}$ or —$CONR^{18}R^{19}$, $R^{17}$ represents hydrogen, alkyl, halogenoalkyl, unsubstituted or halogen-, alkyl- or halogenoalkyl-substituted cycloalkyl or represents phenyl which is unsubstituted or mono- to pentasubstituted by radicals $W^4$, $R^{18}$ and $R^{19}$ independently represent hydrogen, alkyl, alkenyl, halogenoalkyl, halogenoalkenyl, alkoxy, unsubstituted or halogen-, alkyl- or halogenoalkyl-substituted cycloalkyl or cycloalkylalkyl or represent aryl or arylalkyl, each of which is unsubstituted or mono- to pentasubstituted by radicals $W^4$, represent —$OR^{14}$ or —$NR^{15}R^{16}$ or together represent an alkylene chain having 2 to 6 members in which optionally one methylene group is replaced by oxygen, and $W^4$ represents halogen, cyano, nitro, alkyl, alkoxy, halogenoalkyl, halogenoalkoxy, dialkylamino, alkoxycarbonyl, dialkylaminocarbonyl or —$S(O)_oR^3$.

2. The 2-hetaryl-3,4-dihydro-2H-pyrrole of the formula (I) according to claim 1, wherein Hetaryl represents an unsaturated 6-membered heterocycle having one or more nitrogen atoms and which is unsubstituted or mono- or poly-substituted by radicals selected from the group consisting of alkyl, alkoxy, halogen, cyano, halogenoalkyl, halogenoalkoxy, $S(O)_oR^3$, carbamoyl, thiocarbamoyl, alkoximino and halogenoalkylthio, Ar represents the radical

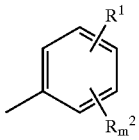

wherein m represents 0, 1, 2, 3, $R^1$ represents a substituent in the meta- or para-position selected from the group consisting of hydrogen, halogen and one of the groupings below (l) —X—A (m) —B—Z—D (n) —Y—E $R^2$ represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —$S(O)_oR^3$, o represents 0, 1 or 2, $R^3$ represents unsubstituted or fluorine- or chlorine-substituted $C_1$–$C_6$-alkyl, X represents a direct bond, oxygen, sulphur, carbonyl, carbonyloxy, oxycarbonyl, $C_1$–$C_4$-alkylene, $C_2$–$C_4$- alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene, A represents phenyl, naphthyl or tetrahydronaphthyl, each of which is unsubstituted or mono- to tetrasubstituted by radicals $W^1$, or represents a 5- to 10-membered heterocycle which contains 1 or 2 aromatic rings, is unsubstituted or mono- to tetrasubstituted by radicals $W^2$ and has 1 to 4 heteroatoms, which consists of 0 to 4 nitrogen atoms, 0 to 2 oxygen atoms and 0 to 2 sulphur atoms, B represents p-phenylene which is unsubstituted or mono- or disubstituted by radicals $W^1$, Z represents oxygen or sulphur, D represents hydrogen, $C_1$–$C_{16}$-alkyl, $C_2$–$C_{16}$-alkenyl, $C_2$–$C_6$-alkynyl, $C_1$–$C_{16}$-halogenoalkyl, $C_2$–$C_{16}$-halogenoalkenyl, or represents unsubstituted or halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, or represents unsubstituted or halogen- or $C_1$–$C_4$-alkylsubstituted $C_5$–$C_8$-cycloalkenyl or $C_5$–$C_8$cycloalkenyl-$C_1$–$C_4$-alkyl, or represents in unsubstituted or nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or a 5- to 6-ring-membered hetaryl-$C_1$–$C_6$-alkyl having 1 or 2 heteroatoms selected from the group consisting of nitrogen, oxygen and sulphur, or represents —CO—$R^4$, —CO—$NR^5R^6$ or represents the grouping

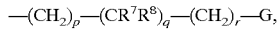

Z and D also together represent unsubstituted or nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is unsubstituted or mono- or disubstituted by radicals $W^1$, E represents hydrogen, $C_1$–$C_{16}$-alkyl, $C_2$–$C_{16}$-alkeny, $C_2$–$C_6$-alkynyl, $C_1$–$C_{16}$-halogenoalkyl, $C_2$–$C_{16}$-hatogenoalkenyl, or represents unsubstituted or halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, or represents unsubstituted or halogen- or $C_1$–$C_4$-alkyl-substituted $C_5$–$C_8$-cycloalkenyl, or represents phenyl which is unsubstituted or mono- to tetrasubstituted by radicals $W^1$ or represents 5- to 6-membered hetaryl which is unsubstituted or mono- to tetrasubstituted by radicals $W^2$ and has 1 or 2 heteroatoms from the group consisting of nitrogen, oxygen and sulphur or represents the grouping

$R^4$ represents $C_1$–C12-alkyl, $C_1$–$C_{12}$-alkoxy, $C_2$–$C_{12}$-alkenyl, $C_2$–$C_{12}$-alkenyloxy, or represents unsubstituted or halogen-, $C_1$–$C_4$-alkyl-, $C_2$–$C_4$-alkenyl-, $C_1$–$C_4$-halogenoalkyl- or $C_2$–$C_4$-halogenoalkenyl-substitute $C_3$–$C_8$cycloalkyl, $C_3$–$C_8$-cycloalkyloxy or $C_3$–$C_8$-cycloalkyl-$C_1$–$C_6$-alkyloxy or represents phenyl or naphthyl, each of which is unsubstituted or mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, $R^5$ represents hydrogen or $C_1$–$C_{12}$-alkyl, $R^6$ represents $C_1$–$C_{12}$-alkyl, $C_1$–$C_{12}$-halogenoalkyl, or represents unsubstituted or halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl or represents phenyl or phenyl-$C_1$–$C_6$-alkyl, each of which is unsubstituted or mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, p, q and r independently represent 0, 1, 2 or 3, such that the sum of p, q and r is less than 6, $R^7$ and $R^8$ independently represent hydrogen or $C_1$–$C_4$-alkyl, G represents cyano, represents a 5- or 6-membered heterocycle which is unsubstituted or mono- to trisubstituted by halogen, $C_1$–$C_4$-alkyl or $C_1$–$C_4$-halogenoalkyl and unsubstituted or substituted at the point of linkage by the radical $R^9$ and has 1 to 3 identical or different heteroatoms selected from the group consisting of nitrogen, oxygen and sulphur or represents one of the following groupings:

 (a)

 (b)

 (c)

 (d)

 (e)

 (f)

 (g)

 (h)

 (i)

 (j)

 (k)

$R^9$ represents hydrogen, $C_1$–$C_6$-alkyl, $C_2$–$C_6$-alkenyl, $C_1$–$C_4$-halogenoalkyl, $C_2$–$C_6$-halogenoalkenyl, unsubstituted or halogen-,

159

$C_1$–$C_4$-alkyl- or $C_1$–$C_4$-halogenoalkyl-substituted $C_3$–$C_6$-cycloalkyl or represents phenyl which is unsubstituted or mono- to pentasubstituted by $C_1$–$C_4$-alkylcarbonylamino, $C_1$–$C_4$-alkylcarbonyl-$C_1$–$C_4$-alkylamino and/or by radicals $W^3$, $R^{10}$ represents hydrogen, $C_1$–$C_4$-alkyl, $C_2$–$C_6$-alkenyl, $C_1$–$C_4$-halogenoalkyl, $C_2$–$C_6$-halogenoalkenyl, represents unsubstituted or halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represents $C_6$–$C_{10}$-aryl-$C_1$–$C_4$-alkyl which is unsubstituted or mono- to tetrasubstituted by radicals $W^3$, $R^{11}$ and $R^{12}$ independently represent hydrogen, $C_1$–$C_4$alkyl, $C_3$–$C_6$-alkenyl, $C_1$–$C_4$-halogenoalkyl, $C_3$–$C_6$-halogenoalkenyl, $C_1$–$C_4$-alkoxy, or represent unsubstituted or halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl, or represent phenyl or phenyl-$C_1$–$C_4$-alkyl, each of which is unsubstituted or mono- to pentasubstituted by radicals $W^3$, or represent —$OR^{10}$ or —$NR^9R^{10}$ or together represent an alkylene chain having 4 to 6 members in which unsubstituted or one methylene group is replaced by oxygen, $R^{13}$ represents —$OR^{10}$, —$NR^9R^{10}$ or —$N(R^9)$—$COOR^{10}$, $R^{14}$, $R^{15}$ and $R^{16}$ independently represent $C_1$–$C_6$-alkyl, $W^1$ represents hydrogen, halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_2$–$C_6$-halogenoalkenyloxy, $C_1$–$C_6$-alkylcarbonyl, $C_1$–$C_{16}$-alkoxycarbonyl, pentafluorothio or —$S(O)_oR^3$, $W^2$ represents halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_1$–$C_6$-alkylcarbonyl, $C_1$–$C_{16}$-alkoxycarbonyl, pentafluorothio, —$S(O)_oR^3$ or —$C(R^9)$=$N$—$R^{13}$, $W^3$ represents halogen, cyano, nitro, $C_1$–$C_4$-alkyl, $C_1$–$C_4$-alkoxy, $C_1$–$C_4$-halogenoalkyl, $C_1$–$C_4$-halogenoalkoxy, di-$C_1$–$C_4$-alkylamino, —$S(O)_oR^3$, —$COOR^{17}$ or —$CONR^{18}R^{19}$, $R^{17}$ represents hydrogen, $C_1$–$C_4$-alkyl, $C_1$–$C_4$-halogenoalkyl, unsubstituted or halogen-, $C_1$–$C_4$-alkyl- or $C_1$–$C_4$-halogenoalkyl-substituted $C_3$–$C_7$-cycloalkyl or represents phenyl which is unsubstituted or mono- to pentasubstituted by radicals $W^4$, $R^{18}$ and $R^{19}$ independently represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, or represent unsubstituted or halogen-, $C_1$–$C_4$-alkyl- or $C_1$–$C_4$-halogenoalkyl-substituted $C_3$–$C_6$cycloalkyl or $C_3$–$C_6$-cycloalkyl-$C_1$–$C_4$-alkyl or represent phenyl or phenyl-$C_1$–$C_4$-alkyl, each of which is unsubstituted or mono- to pentasubstituted by radicals $W^4$, or represent —$OR^{14}$ or —$NR^{15}R^{16}$ or together represent an alkylene chain having 4 to 6 members in which optionally one methylene group is replaced by oxygen, $W^4$ represents halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, di-$C_1$–$C_4$-alkylamino, $C_1$–$C_6$-alkoxycarbonyl, di-$C_1$–$C_6$-alkylaminocarbonyl or —$S(O)_oR^3$.

160

3. The 2-hetaryl-3,4-dihydro-2H-pyrrole of the formula (I) of claim 2, wherein Hetaryl represents pyridyl, which is unsubstituted or mono- to polysubstituted by alkyl, alkoxy, halogen, cyano, halogenoalkyl, halogenoalkoxy, $S(O)_oR^3$, carbamoyl, thiocarbamoyl, alkoximino or halogenoalkylthio.

4. The 2-hetaryl-3,4dihydro-2H-pyrrole of the formula (I) according to claim 1, wherein Hetaryl represents an unsaturated 6-membered heterocycle having one to three nitrogen atoms and which is unsubstituted or substituted by one to three substituents selected from the group consisting of alkyl, alkoxy, fluorine, chlorine, bromine halogenoalkyl, halogenoalkoxy, halogenoalkylthio, $S(O)_oR^3$, —$CONH_2$, $CSNH_2$, —$CH$=$N$—$O(alkyl)$ and cyano, Ar represents the radical

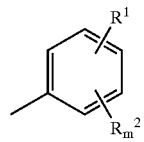

wherein m represents 0, 1 or 2, $R^1$ represents a substituent in the meta- or para-position selected from the group consisting of hydrogen, fluorine, chlorine, bromine, iodine and one of the groupings below (l) —X—A (m) —B—Z—D (n) —Y—E, $R^2$ represents hydrogen, fluorine, chlorine, bromine, iodine, cyano, nitro, $C_1$–$C_{16}$-alkyl, $C_1$–$C_{16}$-alkoxy, or represents fluorine- or chlorine-substituted $C_1$–$C_6$-alkyl or $C_1$–$C_6$-alkoxy, represents $C_1$–$C_8$-alkoxy-$C_1$–$C_8$-alkoxy, or —$S(O)_oR^3$, o represents 0, 1 or 2, $R^3$ represents $C_1$–$C_4$-alkyl or represents fluorine- or chlorine-substituted methyl or ethyl, X represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene, A represents phenyl, naphthyl or tetrahydronaphthyl, each of which is unsubstituted or mono- to trisubstituted by radicals $W^1$, or represents a 5- to 10-membered heterocyclyl which contains 1 or 2 aromatic rings, and is in each case unsubstituted or mono- to trisubstituted by radicals $W^2$ and has 1 to 4 heteroatoms consisting of 0 to 4 nitrogen atoms, 0 to 2 oxygen atoms and 0 to 2 sulphur atoms, B represents phenylene which is unsubstituted or mono- or disubstituted by radicals $W^1$, Z represents oxygen or sulphur, D represents hydrogen, $C_1$–$C_{16}$-alkyl, $C_2$–$C_{16}$-alkenyl, $C_2$–$C_6$-alkynyl, or represents fluorine- or chlorine-substituted $C_1$–$C_4$-alkyl or $C_2$–$C_4$-alkenyl, or represents $C_3$–$C_6$-cycloalkyl or $C_{3-C6}$-cycloalkyl-$C_1$–$C_4$-alkyl, each of which is unsubstituted or substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl, fluorine-, chlorine- or bromine-substituted phenyl or styryl, or represents unsubstituted or fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, or represents phenyl-$C_1$–$C_4$-alkyl, naphthyl-$C_1$–$C_4$-alkyl, tetrahydronaphthyl-$C_1$–$C_6$-alkyl or a 5- or 6-ring-membered heterocyclyl-$C_1$–$C_4$-alkyl having 1 or 2 heteroatoms from the group consisting of nitrogen, oxygen and sulphur, each of which is unsubstituted or substituted by nitro, fluorine, chlorine, bromine, $C_1$–$C_6$-alkyl, $C_1$–$C_6$-alkoxy, fluorine or chlorine-substituted $C_1$–$C_4$-alkyl or $C_1$–$C_4$-alkoxy, or represents —CO—$R^4$, —CO—$NR^5R^6$, or the grouping —$(CH_2)_p$—$(CR^7R^8)_q$—$(CH_2)_r$—G, Z and D also together represent phenoxy-$C_1$–$C_3$-alkyl which is unsubstituted or substituted by nitro, fluorine, chlorine, bromine, $C_1$–$C_4$-alkyl, $C_1$–$C_4$-alkoxy, fluorine- or chlorine-substituted $C_1$–$C_4$-alkyl or $C_1$–$C_4$-alkoxy, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is unsubstituted or mono- or disubstituted by radicals $W^1$, E represents hydrogen, $C_1$–$C_{16}$-alkyl, $C_2$–$C_{16}$-alkenyl, $C_2$–$C_6$-alkynyl, or represents fluorine- or chlorine-substituted $C_1$–$C_4$-alkyl or $C_2$–$C_4$-alkenyl, or represents $C_3$–$C_6$-cycloalkyl which is unsubstituted or substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl, fluorine-, chlorine- or bromine-substituted phenyl or styryl, or represents unsubstituted or fluorine-, chlorine-, bromine- or $C_1$–$C_4$-alkyl-substituted $C_5$–$C_6$-cycloalkenyl, or represents phenyl which is unsubstituted or mono- to trisubstituted by radicals $W^1$ or represents a 5 or 6-membered heterocyclyl which is in each case mono- or disubstituted by radicals $W^2$ and have 1 or 2 heteroatoms from the group consisting of nitrogen, oxygen and sulphur or represent the grouping —$(CH_2)_p$—$(CR^7R^8)_q$—$(CH_2)_r$—G, $R^4$ represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is unsubstituted or substituted by fluorine, chlorine, $C_1$–$C_3$-alkyl fluorinen or chlorine-substituted $C_1$–$C_2$-alkyl or $C_2$–$C_3$-alkenyl, or represents phenyl which is unsubstituted or mono- or disubstituted by fluorine, chlorine, bromine, iodine, $C_1$–$C_4$-alkyl, $C_1$–$C_4$-alkoxy, fluorine- or chlorine-substituted $C_1$–$C_3$-alkyl or $C_1$–$C_4$-alkoxy, $R^5$ represents hydrogen or $C_1$–$C_4$-alkyl, $R^6$ represents $C_1$–$C_4$-alkyl or represents phenyl or benzyl, each of which is unsubstituted or mono- or disubstituted by fluorine, chlorine, bromine, $C_1$–$C_4$-alkyl, fluorine- or chlorine-substituted $C_1$–$C_4$-alkyl or $C_1$–$C_4$-alkoxy, p, q and r independently represent 0, 1, 2 or 3, such that the sum of p, q and r is less than 6, $R^7$ and $R^8$ independently represent hydrogen or $C_1$–$C_4$-alkyl, G represents cyano, or represents a 5 or 6-membered heterocyclyl which is unsubstituted or mono- to trisubstituted by fluorine, chlorine, bromine, $C_1$–$C_4$-alkyl or by fluorine- or chlorine-substituted $C_1$–$C_4$-alkyl and optionally substituted at the point of linkage by the radical $R^9$ and has 1 to 3 identical or different heteroatoms selected from the group consisting of nitrogen, oxygen and sulphur or represents one of the following groupings:

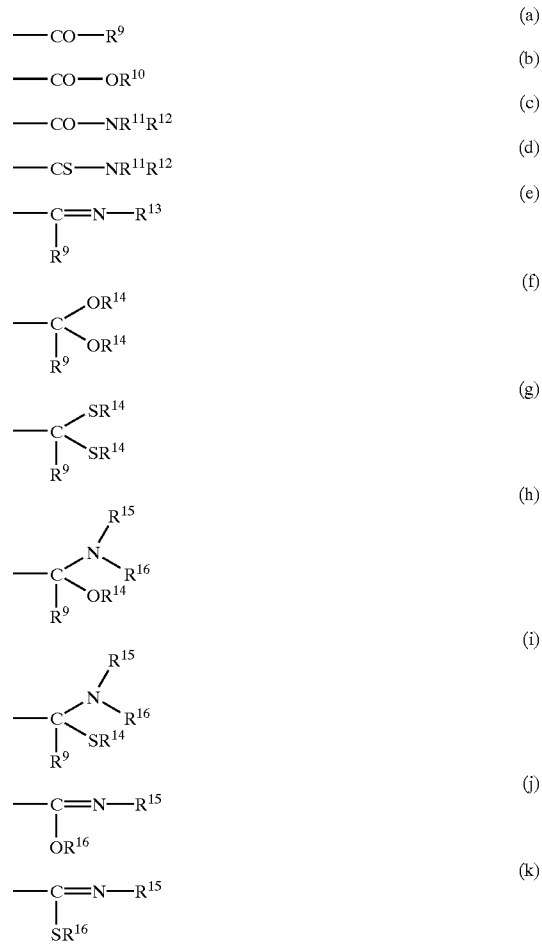

$R^9$ represents hydrogen, $C_1$–$C_6$-alkyl, $C_2$–$C_6$-alkenyl, or represents fluorine- or chlorine-substituted $C_1$–$C_4$-alkyl or $C_2$–$C_6$-alkenyl, or represents $C_3$–$C_6$cycloalkyl which is unsubstituted or substituted by fluorine, chlorine, $C_1$–$C_4$-alkyl, fluorine- or chlorine-substituted $C_1$–$C_4$-alkyl or represents phenyl which is unsubstituted or mono- to trisubstituted by $C_1$–$C_4$-alkylcarbonylamino, $C_1$–$C_4$-alkylcarbonyl-$C_1$–$C_4$-alkylamino and/or radicals $W^3$, $R^{10}$ represents hydrogen, $C_1$–$C_4$-alkyl, $C_3$–$C_6$-alkenyl, or represents fluorine- or chlorine-substituted $C_1$–$C_4$-alkyl or $C_3$–$C_6$-alkenyl, or represents $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl, fluorine- or chlorine-substituted $C_1$–$C_4$-alkyl, or represents phenyl-$C_1$–$C_4$-alkyl or naphthyl-$C_1$–$C_4$-alkyl, each of which is unsubstituted or mono- to trisubstituted by radicals $W^3$, $R^{11}$ and $R^{12}$ independently represent hydrogen, $C_1$–$C_4$-alkyl, $C_3$–$C_6$-alkenyl, or represent fluorine- or chlorine-substituted $C_1$–$C_4$-alkyl or $C_3$–$C_6$-alkenyl, or represent $C_1$–$C_4$-alkoxy, or represent $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl, fluorine- or chlorine-substituted $C_1$–$C_4$-alkyl, or represent phenyl or phenyl-$C_1$–$C_4$-alkyl, each of which is unsubstituted or mono to trisubstituted by radicals $W^3$, or represent —$OR^{10}$ or —$NR^9R^{10}$ or together —$(CH_2)_5$—, —$(CH_2)_6$— or —$(CH_2)_2$—O—$(CH_2)_2$—, $R^{13}$ represents —$OR^{10}$, —$NR^9R^{10}$ or —$N(R^9)$—$COOR^{10}$, $R^{14}$, $R^{15}$ and $R^{16}$ independently represent $C_1$–$C_4$-alkyl, $W^1$ represents hydrogen, fluorine, chlorine, bromine, iodine, cyano, formyl, nitro, $C_1$–$C_4$-alkyl, $C_1$–$C_4$-alkoxy, or represents fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_oR^3$, $W^2$ represents fluorine, chlorine, bromine, cyano, formyl, nitro, $C_1$–$C_4$-alkyl, $C_1$–$C_4$-alkoxy, or represents fluorine or chlorine-substituted $C_1$–$C_4$-alkyl or $C_1$–$C_4$-alkoxy, or represents $C_1$–$C_4$-alkylcarbonyl, $C_1$–$C_4$-alkoxycarbonyl, —$S(O)_oR^3$ or —$C(R^9)$=N—$R^{13}$, $W^3$ represents fluorine, chlorine, bromine, cyano, nitro, $C_1$–$C_4$-alkyl, $C_1$–$C_4$-alkoxy, or represents fluorine- or chlorine-substituted $C_1$–$C_4$-alkyl or $C_1$–$C_4$-alkoxy, or represents di-$C_1$–$C_4$-alkylamino, —$S(O)_oR^3$, —$COOR^{17}$ or —$CONR^{18}R^{19}$, $R^{17}$ represents hydrogen, $C_1$–$C_4$-alkyl, fluorine- or chlorine-substituted $C_1$–$C_4$-alkyl, or represents $C_3$–$C_6$–Cycloalkyl which is unsubstituted or substituted by fluorine, chlorine, $C_1$–$C_4$-alkyl, fluorine- or chlorine-substituted $C_1$–$C_4$-alkyl or represents phenyl which is unsubstituted or mono- to trisubstituted by radicals $W^4$, $R^{18}$ and $R^{19}$ independently represent hydrogen, $C_1$–$C_4$-alkyl, $C_3$–$C_6$-alkenyl, or represent fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$cycloalkyl-$C_1$–$C_4$-alkyl, each of which is unsubstituted or substituted by fluorine, chlorine, $C_1$–$C_4$-alkyl, fluorine- or chlorine-substituted $C_1$–$C_4$-alkyl, or represent phenyl or phenyl-$C_1$–$C_4$-alkyl, each of which is unsubstituted or mono- to trisubstituted by radicals $W^4$, represent —$OR^{14}$ or —$NR^{15}R^{16}$ or together represent —$(CH_2)_5$—, —$(CH_2)_6$— or —$(CH_2)_2$—O—$(CH_2)_2$—, $W^4$ represents fluorine, chlorine, bromine, cyano, nitro, $C_1$–$C_4$-alkyl, $C_1$–$C_4$-alkoxy, or represents fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_oR^3$.

5. The 2-hetaryl-3,4-dihydro-2H-pyrrole of the formula (I) of claim 4, wherein Hetaryl represents pyridyl, which is unsubstituted or mono- to trisubstituted by alkyl, alkoxy, fluorine, chlorine, bromine halogenoalkyl, halogenoalkoxy, halogenoalkylthio, $S(O)_oR^3$, —$CONH_2$, $CSNH_2$, —CH=N—O(alkyl) and cyano.

6. The 2-hetaryl-3,4dihydro-2H-pyrrole of the formula (I) according to claim 1, wherein Hetaryl represents pyridyl which is unsubstituted or mono- or disubstituted by substituents selected from the group consisting of fluorine, chlorine, bromine cyano, methyl, methoxy, trifluoromethoxy, trifluoromethylthio, $S(O)_oR^3$ and trifluoromethyl, Ar represents the radical

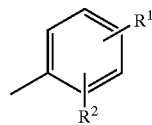

wherein $R^1$ represents a substituent in the meta- or para-position selected from the group consisting of hydrogen, fluorine, chlorine, bromine, iodine and one of the groupings below

—X—A  (I)

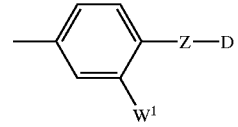  (m-a)

—Y—E,  (n)

$R^2$ represents hydrogen, fluorine, chlorine, bromine, methyl, ethyl, methoxy, ethoxy, methylthio, ethylthio, trifluoromethyl, difluoromethoxy, trifluoromethoxy or trifluoromethylthio, o represents 0, 1 or 2, $R^3$ represents methyl, ethyl, n-propyl, isopropyl, difluoromethyl or trifluoromethyl, X represents a direct bond, oxygen, sulphur, carbonyl, —$CH_2$—, —$(CH_2)_2$—, —CH=CH—(E or Z), —C≡C—, —$CH_2O$—, —$(CH_2)_2O$—, —$CH(CH_3)$O—, —$OCH_2$—, —$O(CH_2)_2$—, —$SCH_2$—, —$S(CH_2)_2$—, —$SCH(CH_3)$—, $C_1$–$C_4$-alkylenedioxy, A represents phenyl which is unsubstituted or mono- or disubstituted by radicals $W^1$ or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is unsubstituted or mono- or disubstituted by radicals $W^2$, Z represents oxygen or sulphur, D represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butynyl, pentynyl, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, represents cyclopropyl, cyclobutyl, cyclopentyl, cyclohexyl, cyclopropylmethyl, cyclobutylmethyl, cyclopentylmethyl or cyclohexylmethyl, each of which is unsubstituted or mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl$_2$, phenyl, styryl, fluorine-, chlorine- or bromine-substituted phenyl or 4-chlorostyryl, represents cyclopentenyl, cyclohexenyl, cyclohexenylmethyl or cyclopentenylmethyl, each of which is unsubstituted or substituted by fluorine, chlorine, methyl, ethyl, n-propyl, isopropyl, n-butyl, isobutyl, sec-butyl or tert-butyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is unsubstituted or mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—R$^4$, —CO—NR$^5$R$^6$ or the grouping —(CH$_2$)$_p$—(CR$^7$R$^8$)$_q$—(CH$_2$)$_r$—G, Z and D also together represent phenoxymethyl which is unsubstituted or mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy, Y represents a direct bond, oxygen, sulphur, carbonyl, —CH$_2$—, —(CH$_2$)$_2$—, —CH=CH—(E or Z), —C≡C—, —CH$_2$O—, —(CH$_2$)$_2$O—, —CH(CH$_3$)O—, —OCH$_2$—, —O(CH$_2$)$_2$—, —SCH$_2$—, —S(CH$_2$)$_2$—, —SCH(CH$_3$)—, C$_1$-C$_4$-alkylenedioxy, or represents p-phenylene which is unsubstituted or monosubstituted by a radical W$^1$, E represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butynyl, pentynyl, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, or represents cyclopropyl, cyclobutyl, cyclopentyl or cyclohexyl, each of which is unsubstituted or mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl$_2$, phenyl, styryl, in each case fluorine-, chlorine- or bromine-substituted phenyl or by 4-chlorostyryl, represents cyclopentenyl or cyclohexenyl, each of which is unsubstituted or substituted by fluorine, chlorine, methyl, ethyl, n-propyl, isopropyl, n-butyl, isobutyl, sec-butyl or tert-butyl, or represents phenyl which is unsubstituted or mono- or disubstituted by radicals W$^1$, or represents furyl, thienyl, pyrrolyl, oxazolyl, isoxazolyl, thiazolyl or pyridyl, each of which is unsubstituted or mono- or disubstituted by radicals W$^2$, or represents the grouping —(CH$_2$)$_p$—(CR$^7$R$^8$)$_q$—(CH$_2$)$_r$—G, R$^4$ represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl, R$^5$ represents hydrogen, R$^6$ represents methyl, ethyl, or phenyl which is unsubstituted or monosubstituted by chlorine, p, q and r independently represent 0, 1, 2 or 3, such that the sum of p, q and r is less than 4, R$^7$ and R$^8$ independently represent hydrogen, methyl, ethyl, n-propyl, isopropyl, n-butyl, isobutyl, sec-butyl, tert-butyl, G represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2dithiolanyl, 1,3-dithian-2-yl or 1,3-thioxan-2-yl, each of which is unsubstituted or mono- to trisubstituted by fluorine, chlorine, bromine, methyl, ethyl, n-propyl, isopropyl or trifluoromethyl and optionally substituted at the point of linkage by the radical R$^9$ or represents one of the following groupings.

—CO—R$^9$          (a)

—CO—OR$^{10}$          (b)

—CO—NR$^{11}$R$^{12}$          (c)

—CS—NR$^{11}$R$^{12}$          (d)

$$-\underset{\underset{R^9}{|}}{C}=N-R^{13} \quad (e)$$

$$-\underset{\underset{R^9}{|}}{C}\underset{OR^{14}}{\overset{OR^{14}}{<}} \quad (f)$$

$$-\underset{\underset{R^9}{|}}{C}\underset{SR^{14}}{\overset{SR^{14}}{<}} \quad (g)$$

$$-\underset{\underset{R^9}{|}}{C}\underset{OR^{14}}{\overset{N\underset{R^{16}}{\overset{R^{15}}{<}}}{<}} \quad (h)$$

$$-\underset{\underset{R^9}{|}}{C}\underset{SR^{14}}{\overset{N\underset{R^{16}}{\overset{R^{15}}{<}}}{<}} \quad (i)$$

R$^9$ represents hydrogen, methyl, ethyl, n-propyl, isopropyl, n-butyl, isobutyl, sec-butyl, tert-butyl, the isomeric pentyls, the isomeric hexyls, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, C$_3$-C$_6$-alkenyl, C$_3$-C$_6$-alkenyl which is mono- to trisubstituted by fluorine or chlorine, or represents cyclopropyl, cyclopentyl or cyclohexyl, each of which is unsubstituted or mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents phenyl which is unsubstituted or mono- or disubstituted by methylcarbonylamino, ethylcarbonylamino, methylcarbonyl-methylamino and/or radicals $W^3$, $R^{10}$ represents hydrogen, methyl, ethyl, n-propyl, isopropyl, n-butyl, isobutyl, sec-butyl, tert-butyl, —$CH_2CF_3$, allyl, or represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is unsubstituted or mono- or disubstituted by fluorine, chlorine, methyl, ethyl, n-propyl, isopropyl, —$CF_3$, $CHF_2$, —$CClF_2$, —$CF_2CHFCl$, —$CF_2CH_2F$, —$CF_2CHF_2$, —$CF_2CCl_3$ or —$CH_2CF_3$, or represents benzyl or phenethyl, each of which is unsubstituted or mono- or disubstituted by radicals $W^3$, $R^{11}$ and $R^{12}$ independentby represent hydrogen, methyl, ethyl, n-propyl, isopropyl, n-butyl, isobutyl, sec-butyl, tert-butyl, —$CH_2CF_3$, methoxy, ethoxy, allyl, represent cyclopropyl, cyclopentyl, cyclohexyl, cyclopropylmethyl, cyclopentylmethyl or cyclohexylmethyl, each of which is unsubstituted or mono- or disubsttuted by fluorine, chlorine, methyl, ethyl, n-propyl, isopropyl or trifluoromethyl, represent phenyl, benzyl or phenethyl, each of which is unsubstituted or mono- or disubstituted by radicals $W^3$, represent —$OR^{10}$ or —$NR^9R^{10}$, $R^{13}$ represents —$OR^{10}$, —$NR^9R^{10}$ or —$N(R^9)$—$COOR^{10}$, $R^{14}$, $R^{15}$ and $R^{16}$ independently represent methyl, ethyl, n-propyl or isopropyl, $W^1$ represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, tri-fluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbonyl, iso-butoxycarbonyl, sec-butoxycarbonyl, tert-butoxycarbonyl or —$S(O)_oR^3$, $W^2$ represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —$CH=N$—$OCH_3$, —$CH=N$—$OC_2H_5$, —$CH=N$—$OC_3H_7$, —$C(CH_3)=N$—$OCH_3$, —$C(CH_3)=N$—$OC_2H_5$, —$C(CH_3)=N$—$OC_3H_7$, —$C(C_2H_5)=N$—$OCH_3$, —$C(C_2H_5)=N$—$OC_2H_5$ or —$C(C_2H_5)=N$—$OC_3H_7$, $W^3$ represents fluorine, chlorine, cyano, nitro, methyl, ethyl, methoxy, ethoxy, methylthio, trifluoromethyl, trifluoromethoxy, trifluoromethylthio, diethylamino, diethylamino, —$COOR^{17}$ or —$CONR^{18}R^{19}$, $R^{17}$ represents hydrogen, methyl, ethyl, n-propyl, isopropyl, tert-butyl, —$CH_2CF_3$, represents cyclopropyl, cyclopentyl or cyclohexyl, each of which is unsubstituted or mono- or disubstituted by fluorine, chlorine, methyl, ethyl, n-propyl, isopropyl or —$CF_3$, or represents phenyl which is unsubstituted or mono- or disubstituted by radicals $W^4$, $R^{18}$ and $R^{19}$ independently represent hydrogen, methyl, ethyl, n-propyl, isopropyl, n-butyl, isobutyl, sec-butyl, tert-butyl, —$CH_2CF_3$, methoxy, ethoxy, allyl, represent cyclopropyl, cyclopentyl, cyclohexyl, cyclopropylmethyl, cyclopentylmethyl or cyclohexylmethyl, each of which is unsubstituted or mono- or disubstituted by fluorine or chlorine, represent phenyl, benzyl or phenethyl, each of which is unsubstituted or mono- or disubstituted by radicals $W^4$, represent —$OR^{14}$ or —$NR^{15}R^{16}$, $W^4$ represents fluorine, chlorine, bromine, cyano, nitro, methyl, ethyl, tert-butyl, methoxy, ethoxy, methylthio, trifluoromethyl, trifluoromethoxy or trifluoromethylthio.

7. The 2-hetaryl-3,4-dihydro-2H-pyrrole of the formula (I) according to claim 1, wherein Ar represents the radical

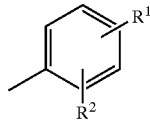

wherein $R^1$ represents hydrogen or phenyl which is mono- to disubstituted by radicals $W^1$, or represents one of the groupings (m-b) —B—O—D (n) —Y—E, B represents p-phenylene which is unsubstituted or monosubstituted by a radical selected from the list $W^1$, Y represents a direct bond, or represents p-phenylene which is unsubstituted or mono- or disubstituted by radicals $W^1$, and D and E are as defined in claim 6, wherein G represents cyano or one of the following groupings

 (a)

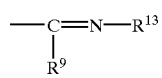 (e)

and Hetaryl, $R^2$, $W^1$, $R^9$ and $R^{13}$ are as defined in claim 6.

8. The 2-hetaryl-3,4-dihydro-2H-pyrrole of the formula (I) according to claim 1, wherein Hetaryl represents a pyridyl group which is unsubstituted or mono- or disubstituted by substituents selected from the group consisting of fluorine, chlorine, cyano, trifluoromethoxy, methoxy, trifluoromethylthio, methyl, $S(O)_oR^3$ and trifluoromethyl, and Ar represents the radical

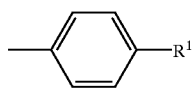

o represents 0, 1 or 2, and

R¹ represents hydrogen or
a) benzyloxy,, phenoxy or phenyl, each of which mono- or disubstituted by radicals W² and/or W¹,
b) furyl, thienyl, pyrrolyl, oxazolyl, isoxazolyl, thiazolyl or pyridyl, specifically thienyl, each of which is mono- or disubstituted by radicals W²,
c) alkyloxy, alkenyloxy,
wherein W¹ and W² are as defined in claim 1 and R³ represents methyl, difluoromethyl or trifluoromethyl.

9. The 2-hetaryl-3,4-dihydro-2H-pyrrole of the formula (I) according to claim 1, wherein Hetaryl represents a pyridyl group which is unsubstituted or mono- or disubstituted by substituents selected from the group consisting of fluorine, chlorine, cyano, trifluoromethoxy, trifluoromethylthio, methyl, methoxy and trifluoromethyl and Ar represents the radical

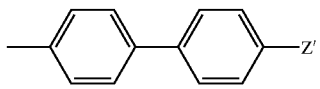

Z' represents hydrogen, fluorine, bromine, chlorine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH₃, —CH=N—OC₂H₅, —CH=N—OC₃H₇, —C(CH₃)=N—OCH₃, —C(CH₃)=N—OC₂H₅, —C(CH₃)=N—OCt₃H₇, —C(C₂H₅)=N—OCH₃, —C(C₂H₅)=N—OC₃H₇, trifluoromethylsulfinyl, trifluoromethylsulfonyl, difluoromethylsulfinyl, difluoromethylsulfonyl, difluoromethylthio.

10. A pesticide composition comprising one or more 2-hetaryl-3,4-dihydro-2H-pyrroles of the formula (I) according to claim 1 and pesticidally acceptable extenders and/or surfactants.

11. A method for controlling a pest comprising applying an effective amount of one or more 2-hetaryl-3,4dihydro-2H-pyrroles of the formula (I) according to claim 1 to the pest and/or its habitat.

12. A process for preparing a pesticide comprising mixing one or more 2-hetaryl-3,4-dihydro-2H-pyrroles of the formula (I) according to claim 1 with at least one of extenders and surfactants.

13. The 2-hetaryl-3,4-dihydro-2H-pyrrole of the formula

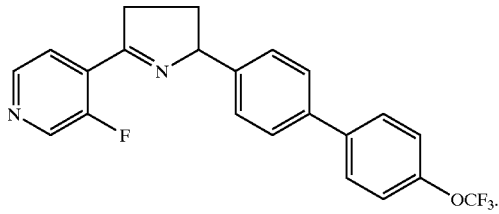

* * * * *